US011707496B2

(12) United States Patent
Cheng et al.

(10) Patent No.: US 11,707,496 B2
(45) Date of Patent: Jul. 25, 2023

(54) ECHOVIRUS FOR TREATMENT OF TUMORS

(71) Applicants: XIAMEN UNIVERSITY, Xiamen (CN); YANG SHENG TANG COMPANY, LTD., Hangzhou (CN)

(72) Inventors: Tong Cheng, Xiamen (CN); Wei Wang, Xiamen (CN); Junkai Wan, Xiamen (CN); Longfa Xu, Xiamen (CN); Xiangzhong Ye, Beijing (CN); Jun Zhang, Xiamen (CN); Ningshao Xia, Xiamen (CN)

(73) Assignees: XIAMEN UNIVERSITY, Xiamen (CN); YANG SHENG TANG COMPANY, LTD., Hangzhou (CN)

( * ) Notice: Subject to any disclaimer, the term of this patent is extended or adjusted under 35 U.S.C. 154(b) by 549 days.

(21) Appl. No.: 16/641,117

(22) PCT Filed: Aug. 15, 2018

(86) PCT No.: PCT/CN2018/100708

§ 371 (c)(1),
(2) Date: Feb. 21, 2020

(87) PCT Pub. No.: WO2019/037642

PCT Pub. Date: Feb. 28, 2019

(65) Prior Publication Data

US 2020/0323933 A1 Oct. 15, 2020

(30) Foreign Application Priority Data

Aug. 24, 2017 (CN) ........................ 201710734483.1

(51) Int. Cl.

| | |
|---|---|
| ***A61K 35/768*** | (2015.01) |
| ***A61P 35/00*** | (2006.01) |
| ***A61K 31/711*** | (2006.01) |
| ***A61K 48/00*** | (2006.01) |
| ***A61K 35/66*** | (2015.01) |
| ***C07K 14/00*** | (2006.01) |
| ***C12N 15/86*** | (2006.01) |
| ***C07K 14/005*** | (2006.01) |
| ***C12N 15/79*** | (2006.01) |
| ***A61K 45/00*** | (2006.01) |
| ***C12N 15/63*** | (2006.01) |
| ***C12N 15/09*** | (2006.01) |
| ***A61K 38/00*** | (2006.01) |
| ***A61K 35/00*** | (2006.01) |
| ***A61K 38/16*** | (2006.01) |
| *A61K 45/06* | (2006.01) |

(52) U.S. Cl.

CPC .......... *A61K 35/768* (2013.01); *A61K 31/711* (2013.01); *A61K 35/00* (2013.01); *A61K 35/66* (2013.01); *A61K 38/00* (2013.01); *A61K 38/16* (2013.01); *A61K 45/00* (2013.01); *A61K 48/00* (2013.01); *A61K 48/0008* (2013.01); *A61P 35/00* (2018.01); *C07K 14/00* (2013.01); *C07K 14/005* (2013.01); *C12N 15/09* (2013.01); *C12N 15/63* (2013.01); *C12N 15/79* (2013.01); *C12N 15/86* (2013.01); *A61K 45/06* (2013.01)

(58) Field of Classification Search

CPC ....... A61P 35/00; A61K 35/768; C12N 15/86; C12N 15/79; C12N 15/63

See application file for complete search history.

(56) References Cited

U.S. PATENT DOCUMENTS

| | | | |
|---|---|---|---|
| 2008/0160031 | A1 | 7/2008 | Shafren |
| 2010/0104578 | A1 | 4/2010 | Shafren |
| 2016/0376562 | A1 | 12/2016 | Venskus et al. |

FOREIGN PATENT DOCUMENTS

| | | | | |
|---|---|---|---|---|
| CN | 102166218 | A | 8/2011 | |
| CN | 105518128 | A | 4/2016 | |
| CN | 107669707 | A | 2/2018 | |
| JP | 2014-502970 | A | 2/2014 | |
| RU | 2 436 873 | C1 | 10/2013 | |
| WO | WO 2606/074526 | A1 | 7/2006 | |
| WO | WO-2006074526 | A1 * | 7/2006 | ......... A61K 31/7105 |
| WO | WO 2015/007788 | A1 | 1/2015 | |

OTHER PUBLICATIONS

Hou et al. 2015 (Construction and characterization of an infectious cDNA clone of Echovirus 25; Virus Research 205:41-44) (Year: 2015).*

Stanway et al. 2000 (Human parachoviruses—biologyand clinical significance; Review in Medical training 10:57-69) (Year: 2000).*

Gromeier et al. 2000 (Intergeneric poliovirus recombinants for the treatment of malignant glioma; PNAS 97(12):6803-6808). (Year: 2000).*

Extended European Search Report dated May 11, 2021 in European Patent Application No. 18849336.5, 7 pages Japanese Office Action dated Aug. 2, 2022 in Japanese Patent Application No. 2020-531804, citing documents 15 and 24-27 therein, 5 pages.

Victor A. Svyatchenko, et al., "Bioselection of coxsackievirus B6 strain variants with altered tropism to human cancer cell lines," Arch Virol, Aug. 1, 2017, 8 pages.

Jeronimo Cello, et al., "Growth Phenotypes and Biosafety Profiles in Poliovirus-Receptor Transgenic Mice of Recombinant Oncolytic Polio/Human Rhinoviruses," Journal of Medical Virology, vol. 80, 2008, pp. 352-359.

(Continued)

*Primary Examiner* — Mary Maille Lyons

(74) *Attorney, Agent, or Firm* — Oblon, McClelland, Maier & Neustadt, L.L.P.

(57) ABSTRACT

Provided are use of an Echovirus 25 (ECHO25) or a modified form thereof, or a nucleic acid molecule comprising a genomic sequence or cDNA sequence of the ECHO25 or a modified form thereof, or a complementary sequence of the genomic sequence or cDNA sequence, in treatment of a tumor in a subject, and in the manufacture of a medicament for treatment a tumor in a subject.

18 Claims, 6 Drawing Sheets

Specification includes a Sequence Listing.

(56) References Cited

OTHER PUBLICATIONS

Patricia Kleinpeter, et al., "Vectorization in an oncolytic vaccinia virus of an antibody, a Fab and a scFv against programmed cell death-1 (PD-1) allows their intratumoral delivery and an improved tumor-growth inhibition," Oncoimmunology, vol. 5, No. 10, e1220467, 2016, 14 pages.
Elizabeth J Kelly, et al., "MicroRNAs and the Regulation of Vector Tropism," Molecular Therapy, vol. 17, No. 3, Mar. 2009, pp. 409-416.
International Search Report dated Nov. 22, 2018 in PCT/CN2018/100708 (submitting English translation only), 5 pages.
Chao, L., et al., "Genetic Characterization of Echovirus 25 Isolaled from Henan", Chinese Journal of Virology, vol. 26 No. 6, Nov. 30, 2020, pp. 443-446 (with English abstract).

* cited by examiner

ECHOVIRUS FOR TREATMENT OF TUMORS

TECHNICAL FIELD

The present invention relates to the field of viruses and the field of tumor treatment. Specifically, the present invention relates to use of an Echovirus 25 (ECHO25) or a modified form thereof, or a nucleic acid molecule comprising a genomic sequence or cDNA sequence of the ECHO25 or a modified form thereof, or a complementary sequence of the genomic sequence or cDNA sequence, in treatment of a tumor in a subject (e.g., a human), and in the manufacture of a medicament for treatment of a tumor in a subject (e.g., a human). The present invention also relates to a method for treating a tumor, which comprises a step of administering to a subject in need thereof an ECHO25 or a modified form thereof, or a nucleic acid molecule comprising a genomic sequence or cDNA sequence of the ECHO25 or a modified form thereof, or a complementary sequence of the genomic sequence or cDNA sequence.

BACKGROUND ART

The current methods for treatment of malignant tumors mainly include surgery, chemotherapy and radiotherapy. These traditional therapies are not satisfactory for the treatment of metastatic tumors, and they may also cause great harm to health of patients. In contrast, as a new type of treatment, using oncolytic virus in tumor treatment method has high specificity, good effect, and small side effects, and thus is currently considered as a promising tumor treatment method.

Oncolytic virus is a virus that can self-replicate in tumor cells, thereby killing, lysing tumor cells, or arresting tumor cell growth. When used for treatment in vivo, oncolytic viruses show specificity for tumor cells, and can directly induce tumor cell death with little or no effect on normal cells. Meanwhile, oncolytic viruses can also indirectly kill tumor cells by inducing cytotoxic T lymphocyte response in the immune system.

Enteroviruses belong to the Picornaviridae family, and their genomes are single-stranded positive-sense RNA. There are following advantages for using enteroviruses as oncolytic viruses: firstly, as single-stranded RNA viruses, their genomes won't undergo any stages of DNA in the host, so that there won't be genotoxicity caused by the insertion of the viral genome into the host's DNA, and thus enteroviruses may have better safety; secondly, the genomes of enteroviruses are relatively small, so that a large number of viruses can be replicated in a short period of time to further infect other tumor cells, thereby causing a strong cytopathic effect; furthermore, the enteroviruses do not contain oncogenes, so that they won't induce tumors; and finally, the genomes of enteroviruses can be modified by reverse genetics technology to achieve the attenuation of viruses and reduce their side effects.

The currently reported enteroviruses with oncolytic activity include chimeric polioviruses for treatment of human solid tumors such as malignant gliomas (Dobrikova et al., Mol Ther 2008, 16 (11): 1865-1872); Coxsackie viruses A13, A15, A18 and A21 that kill human melanoma cells (Au et al., Virol J 2011, 8: 22), and so on. However, it is still necessary to obtain a virus with both tumor-specific and tumor-killing activity.

Echovirus (ECHO) has a full name of enteric cytopathogenic human orphan virus. In the early 1950s, the virus was isolated from feces of healthy children and children with aseptic meningitis and identified by tissue culture. Echovirus 25 belongs to the species human enterovirus B, and its infection mostly occurs in children under 5 years old and shows clinical symptoms mainly including maculopapular rash, diarrhea, and respiratory diseases, and aseptic meningitis, neonatal sepsis, myocarditis etc. may occur in a severe case. At present, oncolytic activity has not been reported for Echovirus 25 in the art.

Contents of the Invention

After intensive experiments and repeated explorations, the inventors of the present application unexpectedly found that Echovirus 25 has significant tumor cell killing ability for specific tumors. Based on this finding, the inventors have developed a new oncolytic virus for treating tumors and a tumor treatment method based on the virus.

Medical Use

Therefore, in a first aspect, the present invention provides use of an Echovirus 25 (ECHO25) or a modified form thereof or an isolated nucleic acid molecule in treatment of a tumor in a subject, or in the manufacture of a medicament for treatment of a tumor in a subject; wherein the isolated nucleic acid molecule comprises a sequence selected from the following:

(1) a genomic sequence or cDNA sequence of ECHO25 or a modified form thereof, and (2) a complementary sequence of the genomic sequence or cDNA sequence.

In certain preferred embodiments, the ECHO25 is a wild-type ECHO25. In certain preferred embodiments, the ECHO25 can be a clinical isolate isolated from an individual infected with Echovirus 25.

In certain preferred embodiments, the genomic sequence of ECHO25 or a modified form thereof has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence as shown in SEQ ID NO: 12. In certain preferred embodiments, the genomic sequence of ECHO25 or a modified form thereof is a nucleotide sequence as shown in SEQ ID NO: 12.

In certain preferred embodiments, the cDNA sequence of ECHO25 or a modified form thereof has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence as shown in SEQ ID NO: 1. In certain preferred embodiments, the cDNA sequence of ECHO25 or a modified form thereof is a nucleotide sequence as shown in SEQ ID NO: 1.

In certain preferred embodiments, the modified form is a modified ECHO25, which has a substitution, insertion, or deletion of one or more nucleotides in the genome as compared to a wild-type ECHO25.

In certain preferred embodiments, as compared to the wild-type ECHO25, the modified ECHO25 has one or more modifications selected from the following:

(1) one or more mutations in an untranslated region (e.g., 5'UTR or 3'UTR);

(2) an insertion of one or more exogenous nucleic acids;

(3) a deletion or mutation of one or more endogenous genes; and (4) any combination of the above three items.

In certain preferred embodiments, the modified ECHO25 comprises one or more mutations in the 5' untranslated region (5'UTR).

In certain preferred embodiments, the modified ECHO25 has a substitution of all or part of the 5'UTR sequence. In certain preferred embodiments, the modified ECHO25 has a substitution of the internal ribosome entry site (IRES) sequence in the 5'UTR with an exogenous IRES sequence, such as an internal ribosome entry site sequence of human rhinovirus 2 (HRV2). In certain preferred embodiments, the internal ribosome entry site sequence of human rhinovirus 2 (HRV2) is shown in SEQ ID NO: 2.

The use of the internal ribosome entry site sequence of human rhinovirus 2 (HRV2) is advantageous in some cases, for example, to improve the tumor specificity of oncolytic viruses. It has been previously reported that in normal human nerve cells, the internal ribosome entry site sequence of human rhinovirus 2 is specifically bound by host RNA-binding proteins (DRBP76 and NF45), thereby preventing the recruitment of factors such as elF4G (Merrill et al. J Virol 2006, 80 (7): 3147-3156; Merrill and Gromeier, J Virol 2006, 80 (14): 6936-6942; Neplioueva et al. PLoS One 2010, 5(7): e11710); in the meantime, without the support of Raf/Erk1/2/MAPK and other signaling pathways, ribosomes can hardly be bound to the internal ribosome entry site sequence of human rhinovirus 2 and therefore translation of viral protein cannot be initiated (Dobrikov et al., Mol Cell Biol 2011, 31 (14): 2947-2959; Dobrikov et al., Mol Cell Biol 2013, 33 (5): 937-946). In human glioma tumor cells, the internal ribosome entry site of human rhinovirus 2 is not affected by the above two factors, and thus can normally initiate transcription and translation of viral protein. Therefore, in some cases, replacing the internal ribosome entry site sequence of ECHO25 with the internal ribosome entry site sequence of human rhinovirus 2 is beneficial to avoid or reduce the toxic and side effects of the virus of the present invention on normal human nerve cells without affecting the use of the virus in the treatment of human gliomas.

In certain preferred embodiments, the modified ECHO25 comprises an exogenous nucleic acid.

In certain preferred embodiments, the exogenous nucleic acid encodes a cytokine (e.g., GM-CSF, preferably human GM-CSF), or an antitumor protein or polypeptide (e.g., a scFv against PD-1 or PD-L1, preferably a scFv against human PD-1 or PD-L1). In certain preferred embodiments, the exogenous nucleic acid is inserted between the 5'UTR and the VP4 gene, or between the VP1 gene and the 2A gene of the genome of the modified ECHO25.

In certain preferred embodiments, the exogenous nucleic acid comprises a target sequence of microRNA (miRNA) (e.g., miR-133 or miR-206). In certain preferred embodiments, the target sequence of microRNA is inserted in the 3' untranslated region (3'UTR) of the genome of the modified ECHO25.

It has been previously reported that the expression level of certain microRNAs in tumor cells is significantly lower than that in normal cells and/or has obvious tissue specificity. Thus, in some cases, it is advantageous that the modified ECHO25 of the present invention comprises a target sequence of such microRNAs, because such microRNAs that are highly expressed in normal cells or tissues can reduce or even block the replication of the modified ECHO25 in the normal cells or tissues via the corresponding target sequence, thereby reducing or even avoiding the toxic and side effects of the modified ECHO25 on non-tumor cells. Such microRNAs include, but are not limited to, miR-133, miR-206, miR-1, miR-143, miR-145, miR-217, let-7, miR-15, miR-16, etc. (see, for example, PCT International Application WO2008103755A1, US patent application US20160143969A1, or Baohong Zhang et al., Developmental Biology, Volume 302, Issue 1, 1 Feb. 2007, Pages 1-12; all of which are incorporated herein in their entirety by reference).

In certain preferred embodiments, the exogenous nucleic acid comprises a target sequence of one or more (e.g., two, three, or four) microRNA as described above. In certain preferred embodiments, the exogenous nucleic acid comprises a target sequence of miR-133 and/or miR-206. In certain preferred embodiments, the target sequence of miR-133 is shown in SEQ ID NO: 3. In certain preferred embodiments, the target sequence of miR-206 is shown in SEQ ID NO: 4. In some cases, the insertion of the target sequence of miR-133 and/or miR-206 is advantageous. This is because miR-133 and miR-206 are specifically expressed in muscle tissue, so that the insertion of the target sequence of miR-133 and/or miR-206 into the modified ECHO25 may change the tissue tropism of the oncolytic virus, thereby reducing or avoiding damage to normal muscle tissue.

In certain preferred embodiments, the modified ECHO25 comprises at least one insertion of the exogenous nucleic acid as described above and/or at least one mutation in the untranslated region as described above.

In certain preferred embodiments, the genomic sequence of the modified ECHO25 has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence selected from: nucleotide sequences as shown in SEQ ID NOs: 13-16. In certain preferred embodiments, the genomic sequence of the modified ECHO25 is a nucleotide sequence as shown in any one of SEQ ID NOs: 13-16.

In certain preferred embodiments, the cDNA sequence of the modified ECHO25 has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence selected from: nucleotide sequences as shown in SEQ ID NOs: 8-11. In certain preferred embodiments, the cDNA sequence of the modified ECHO25 is a nucleotide sequence as shown in any one of SEQ ID NOs: 8-11.

In the present invention, the modified ECHO25 as described above can be obtained by reverse genetics technology, which is known in the art, for example, see Yang L S, Li S X, Liu Y J, et al., Virus Res, 2015, 210: 165-168; Hou W H, Yang L S, Li S X, et al., Virus Res, 2015, 205: 41-44; all of which are incorporated herein in their entirety by reference. In such embodiments, the cDNA of wild-type ECHO25 is typically modified (e.g., by insertion of an exogenous nucleic acid, deletion or mutation of an endogenous gene, or mutation in a non-translated region) to obtain the modified ECHO25.

In the present invention, the ECHO25 or a modified form thereof as described above may be subjected to a pretreatment to reduce or eliminate an immune response against the virus in a subject, wherein the pretreatment may comprise: packaging the ECHO25 in a liposome or micelle, and/or using a protease (e.g., chymotrypsin or trypsin) to remove a capsid protein of the virus to reduce a humoral and/or cellular immunity against the virus in the host.

In the present invention, the ECHO25 or a modified form thereof as described above can be serially passaged for adaptation in tumor cells. In certain preferred embodiments, the tumor cells may be tumor cell lines or tumor cell strains known in the art, or tumor cells obtained by in vivo surgical resection or clinical isolation from an individual (e.g., a subject) having a tumor. In certain preferred embodiments, the ECHO25 or a modified form thereof is serially passaged for adaptation in tumor cells obtained from an individual (e.g., a subject) having a tumor. In certain preferred embodiments, the tumor cells are obtained by surgical resection or clinical isolation from an individual (e.g., a subject) having a tumor. In certain preferred embodiments, the method of serial passaging for adaptation comprises a plurality of (e.g., at least 5, at least 10, at least 15, at least 20) cycles that consists of the following processes: 1) infecting a target tumor cell with the virus; 2) harvesting the virus in the supernatant; and 3) reinfecting a fresh target tumor cell with the obtained virus.

In certain preferred embodiments, the ECHO25 and modified forms thereof as described above can be used in combination. Thus, the medicament may comprise one or more of the ECHO25 and modified forms thereof.

In certain preferred embodiments, the isolated nucleic acid molecule consists of a genomic sequence or cDNA sequence of the ECHO25 or a modified form thereof as described above, or a complementary sequence of the genomic sequence or cDNA sequence. In certain preferred embodiments, the isolated nucleic acid molecule has a genomic sequence of the ECHO25 or a modified form thereof as described above. In certain preferred embodiments, the isolated nucleic acid molecule is RNA. In certain preferred embodiments, the isolated nucleic acid molecule has a nucleotide sequence as shown in any one of SEQ ID NOs: 12-16.

In certain preferred embodiments, the isolated nucleic acid molecule is a vector (e.g., a cloning vector or an expression vector) comprising a genomic sequence or cDNA sequence of the ECHO25 or a modified form thereof as described above, or a complementary sequence of the genomic sequence or cDNA sequence. In certain preferred embodiments, the isolated nucleic acid molecule is a vector (e.g., a cloning vector or an expression vector) comprising a cDNA sequence of the ECHO25 or a modified form thereof as described above, or a complementary sequence of the cDNA sequence.

In certain preferred embodiments, the isolated nucleic acid molecule comprises a complementary sequence of a genomic sequence of the ECHO25 or a modified form thereof as described above. In certain preferred embodiments, the complementary sequence is complementary to a nucleotide sequence selected from the group consisting of:

(1) a nucleotide sequence as shown in SEQ ID NO: 12;

(2) a nucleotide sequence having a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence as shown in SEQ ID NO: 12;

(3) a nucleotide sequence as shown in any one of SEQ ID NOs: 13-16; and (4) a nucleotide sequence having a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence as shown in any of SEQ ID NOs: 13-16.

In certain preferred embodiments, the isolated nucleic acid molecule comprises a complementary sequence of a cDNA sequence of the ECHO25 or a modified form thereof as described above. In certain preferred embodiments, the complementary sequence is complementary to a nucleotide sequence selected from the group consisting of:

(1) a nucleotide sequence as shown in SEQ ID NO: 1;

(2) a nucleotide sequence having a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence as shown in SEQ ID NO: 1;

(3) a nucleotide sequence as shown in any one of SEQ ID NOs: 8-11; and (4) a nucleotide sequence having a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence as shown in any one of SEQ ID NOs: 8-11.

In the present invention, the isolated nucleic acid molecule can be delivered by any means known in the art, for example, a naked nucleic acid molecule (e.g., a naked RNA) can be directly injected, or a non-viral delivery system can be used. The non-viral delivery system can be obtained from a variety of materials well known in the art, including, but not limited to, the materials described in detail in "Yin H, et al. Nat Rev Genet. 2014 August; 15(8): 541-55." and "Riley M K, Vermerris W. Nanomaterials (Basel). 2017 Apr. 28; 7(5). Pii: E94.", which are incorporated herein by reference in their entirety, such as liposomes, inorganic nanoparticles (such as gold nanoparticles), polymers (such as PEG), and so on.

In certain preferred embodiments, the medicament comprises a therapeutically effective amount of the ECHO25 and/or a modified form thereof as described above, or a therapeutically effective amount of the isolated nucleic acid molecule as described above. In certain preferred embodiments, the medicament may be in any form known in the medical arts. For example, the medicament may be in the form of a tablet, a pill, a suspension, an emulsion, a solution, a gel, a capsule, a powder, a granule, an elixir, a lozenge, a suppository, or an injection (including injection solution, lyophilized powder) and so on. In some embodiments, the medicament is an injection solution or a lyophilized powder.

In certain preferred embodiments, the medicament further comprises a pharmaceutically acceptable carrier or excipient. In certain preferred embodiments, the medicament comprises a stabilizer.

In certain preferred embodiments, the medicament optionally further comprises an additional pharmaceutically active agent. In a preferred embodiment, the additional pharmaceutically active agent is a medicament having antitumor activity, such as an additional oncolytic virus, a chemotherapeutic agent or an immunotherapeutic agent.

In the present invention, the additional oncolytic virus includes, but is not limited to, herpesvirus, adenovirus, parvovirus, reovirus, Newcastle disease virus, vesicular stomatitis virus, measles virus, or any combination thereof. The chemotherapeutic agent includes but is not limited to 5-fluorouracil, mitomycin, methotrexate, hydroxyurea, cyclophosphamide, dacarbazine, mitoxantrone, anthracyclines (e.g., epirubicin or doxorubicin), etoposide, platinum compounds (e.g., carboplatin or cisplatin), taxanes (e.g., paclitaxel or taxotere), or any combination thereof. The immunotherapeutic agent includes, but is not limited to, immune checkpoint inhibitors (e.g., anti-PD-1 antibody, anti-PD-L1 antibody or anti-CTLA-4 antibody), tumor-specific targeting antibodies (e.g., rituximab or Herceptin) or any combination thereof.

In certain preferred embodiments, the medicament comprises a unit dose of the ECHO25 and/or a modified form thereof as described above, for example comprising at least $1\times10^2$ pfu, at least $1\times10^3$ pfu, at least $1\times10^4$ pfu, $1\times10^5$ pfu, $1\times10^6$ pfu, at least $1\times10^7$ pfu, at least $1\times10^8$ pfu, at least $1\times10^9$ pfu, at least $1\times10^{10}$ pfu, at least $1\times10^{11}$ pfu, at least $1\times10^{12}$ pfu, at least $1\times10^{13}$ pfu, at least $1\times10^{14}$ pfu, or at least $1\times10^{16}$ pfu of the ECHO25 and/or a modified form thereof. In certain preferred embodiments, the medicament comprises $1\times10^2$ pfu to $1\times10^{17}$ pfu of the ECHO25 and/or a modified form thereof as described above.

In certain preferred embodiments, the medicament contains a unit dose of an isolated nucleic acid molecule as described above, such as the nucleic acid molecule containing $3\times10^{10}$ to $3\times10^{14}$ virus genome copies.

In certain preferred embodiments, the medicament may be administered in combination with an additional therapy. This additional therapy may be any therapy known for tumors, such as surgery, chemotherapy, radiation therapy, immunotherapy, hormone therapy or gene therapy. This additional therapy may be administered before, concurrently with, or after the administration of the medicament.

In certain preferred embodiments, the tumor is selected from the group consisting of gastric cancer, liver cancer, ovarian cancer (e.g., ovarian non-clear cell carcinoma), endometrial cancer, melanoma, prostate cancer, glioma, esophageal cancer, bladder cancer, lymphoma (e.g., histiocytic lymphoma), leukemia (e.g., chronic myeloid leukemia), rhabdomyosarcoma, colorectal cancer, non-small cell lung cancer (e.g., non-small cell lung adenocarcinoma), cervical cancer (e.g., HPV-negative cervical cancer), breast cancer (e.g., breast medullary carcinoma), kidney cancer (e.g., clear cell renal carcinoma), and pancreatic cancer.

In certain preferred embodiments, the tumor is gastric cancer, liver cancer, ovarian cancer (e.g., ovarian non-clear cell carcinoma), endometrial cancer, cervical cancer (e.g., HPV-negative cervical cancer), melanoma, breast cancer (e.g., breast medullary carcinoma), prostate cancer, glioma, esophageal cancer, bladder cancer, lymphoma (e.g., histiocytic lymphoma), or leukemia (e.g., chronic myeloid leukemia).

In certain preferred embodiments, the subject is a mammal, such as a human.

Treatment Method

In a second aspect, the present invention provides a method for treating a tumor, comprising a step of administering to a subject in need thereof an effective amount of an ECHO25 or a modified form thereof, or an effective amount of an isolated nucleic acid molecule; wherein the isolated nucleic acid molecule comprises a sequence selected from the group consisting of:

(1) a genomic sequence or cDNA sequence of the ECHO25 or a modified form thereof, and (2) a complementary sequence of the genomic sequence or cDNA sequence.

In certain preferred embodiments, ECHO25 is administered to the subject. In certain preferred embodiments, the ECHO25 is wild-type ECHO25. In certain preferred embodiments, the ECHO25 may be a clinical isolate that is isolated from an individual infected with Echovirus 25.

In certain preferred embodiments, the genomic sequence of the ECHO25 or a modified form thereof has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence as shown in SEQ ID NO: 12. In certain preferred embodiments, the genomic sequence of the ECHO25 or a modified form thereof is a nucleotide sequence as shown in SEQ ID NO: 12.

In certain preferred embodiments, the cDNA sequence of the ECHO25 or a modified form thereof has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence as shown in SEQ ID NO: 1. In certain preferred embodiments, the cDNA sequence of the ECHO25 or a modified form thereof is a nucleotide sequence as shown in SEQ ID NO: 1.

In certain preferred embodiments, a modified form of ECHO25 is administered to the subject. In certain preferred embodiments, as compared to the wild-type ECHO25, the modified form is a modified ECHO25, which has a substitution, insertion, or deletion of one or more nucleotides in the genome.

In certain preferred embodiments, as compared to the wild-type ECHO25, the modified ECHO25 has one or more modifications selected from the following:

(1) one or more mutations in an untranslated region (e.g., 5'UTR or 3'UTR);

(2) an insertion of one or more exogenous nucleic acids;

(3) a deletion or mutation of one or more endogenous genes; and (4) any combination of the above three items.

In certain preferred embodiments, the modified ECHO25 comprises one or more mutations in the 5' untranslated region (5'UTR).

In certain preferred embodiments, the modified ECHO25 has a substitution of all or part of the 5'UTR sequence. In certain preferred embodiments, the modified ECHO25 has a substitution of the internal ribosome entry site (IRES) sequence in the 5'UTR with an exogenous IRES sequence, such as an internal ribosome entry site sequence of human rhinovirus 2 (HRV2). In certain preferred embodiments, the internal ribosome entry site sequence of human rhinovirus 2 (HRV2) is shown in SEQ ID NO: 2.

In certain preferred embodiments, the modified ECHO25 comprises an exogenous nucleic acid.

In certain preferred embodiments, the exogenous nucleic acid encodes a cytokine (e.g., a GM-CSF, preferably a human GM-CSF), or an antitumor protein or polypeptide (e.g., a scFv against PD-1 or PD-L1, preferably a scFv against human PD-1 or PD-L1). In certain preferred embodiments, the exogenous nucleic acid is inserted between the 5'UTR and the VP4 gene, or between the VP1 gene and the 2A gene of the genome of the modified ECHO25.

In certain preferred embodiments, the exogenous nucleic acid comprises a target sequence of microRNA (miRNA) (e.g., miR-133 or miR-206). In certain preferred embodiments, the target sequence of microRNA is inserted in the 3' untranslated region (3'UTR) of the genome of the modified ECHO25.

In certain preferred embodiments, the exogenous nucleic acid comprises a target sequence of one or more (e.g., 2, 3, or 4) microRNA as described above. In certain preferred embodiments, the exogenous nucleic acid comprises a target sequence of miR-133 and/or miR-206. In certain preferred embodiments, the target sequence of miR-133 is shown in SEQ ID NO: 3. In certain preferred embodiments, the target sequence of miR-206 is shown in SEQ ID NO: 4.

In certain preferred embodiments, the modified ECHO25 comprises at least one insertion of the exogenous nucleic acid as described above and/or at least one mutation in the untranslated region as described above.

In certain preferred embodiments, the genomic sequence of the modified ECHO25 has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence selected from: nucleotide sequences as shown in SEQ ID NOs: 13-16. In certain preferred embodiments, the genomic sequence of the modified ECHO25 is a nucleotide sequence as shown in any one of SEQ ID NOs: 13-16.

In certain preferred embodiments, the cDNA sequence of the modified ECHO25 has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence selected from: nucleotide sequences as shown in SEQ ID NOs: 8-11. In certain preferred embodiments, the cDNA sequence of the modified ECHO25 is a nucleotide sequence as shown in any one of SEQ ID NOs: 8-11.

In certain preferred embodiments, the ECHO25 and modified forms thereof as described above can be used in combination. Thus, one or more of the ECHO25 and modified forms thereof can be administered to a subject.

In certain preferred embodiments, the isolated nucleic acid molecule as described above is administered to the subject.

In certain preferred embodiments, the isolated nucleic acid molecule consists of a genomic sequence or cDNA sequence of the ECHO25 or a modified form thereof, or a complementary sequence of the genomic sequence or cDNA sequence, as described above. In certain preferred embodiments, the isolated nucleic acid molecule has a genomic sequence of the ECHO25 or a modified form thereof as described above. In certain preferred embodiments, the isolated nucleic acid molecule is RNA. In certain preferred embodiments, the isolated nucleic acid molecule has a nucleotide sequence as shown in any one of SEQ ID NOs: 12-16.

In certain preferred embodiments, the isolated nucleic acid molecule is a vector (e.g. a cloning vector or an expression vector) comprising a genomic sequence or cDNA sequence of the ECHO25 or a modified form thereof as described above, or a complementary sequence of the genomic sequence or cDNA sequence. In certain preferred embodiments, the isolated nucleic acid molecule is a vector (e.g., a cloning vector or an expression vector) comprising a cDNA sequence of the ECHO25 or a modified form thereof as described above, or a complementary sequence of the cDNA sequence.

In certain preferred embodiments, the isolated nucleic acid molecule comprises a complementary sequence of a genomic sequence of the ECHO25 or a modified form thereof as described above. In certain preferred embodiments, the complementary sequence is complementary to a nucleotide sequence selected from:

(1) a nucleotide sequence as shown in SEQ ID NO: 12;

(2) a nucleotide sequence having a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence as shown in SEQ ID NO: 12;

(3) a nucleotide sequence as shown in any one of SEQ ID NOs: 13-16; and (4) a nucleotide sequence having a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence shown in any of SEQ ID NOs: 13-16.

In certain preferred embodiments, the isolated nucleic acid molecule comprises a complementary sequence of a cDNA sequence of the ECHO25 or a modified form thereof as described above. In certain preferred embodiments, the complementary sequence is complementary to a nucleotide sequence selected from:

(1) a nucleotide sequence as shown in SEQ ID NO: 1;

(2) a nucleotide sequence having a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence as shown in SEQ ID NO: 1;

(3) a nucleotide sequence as shown in any one of SEQ ID NOs: 8-11; and (4) a nucleotide sequence having a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence as shown in any one of SEQ ID NOs: 8-11.

In the present invention, the isolated nucleic acid molecule can be delivered by any means known in the art, for example, a naked nucleic acid molecule (e.g., naked RNA) can be directly injected, or a non-viral delivery system can be used. The non-viral delivery system can be obtained from a variety of materials well known in the art, including, but not limited to, the materials described in detail in "Yin H, et al. Nat Rev Genet. 2014 August; 15(8): 541-55." and "Riley M K, Vermerris W. Nanomaterials (Basel). 2017 Apr. 28; 7(5). Pii: E94.", which are incorporated herein by reference in their entirety, such as liposomes, inorganic nanoparticles (such as gold nanoparticles), polymers (such as PEG), and so on.

In certain preferred embodiments, the ECHO25 and/or a modified form thereof as described above, or the isolated nucleic acid molecule as described above, can be formulated and administered as a pharmaceutical composition. Such a pharmaceutical composition may comprise a therapeutically effective amount of the ECHO25 and/or a modified form thereof as described above, or a therapeutically effective amount of the isolated nucleic acid molecule as described above. In certain preferred embodiments, the pharmaceutical composition may be in any form known in the medical arts. For example, the pharmaceutical composition may be in the form of a tablet, a pill, a suspension, an emulsion, a solution, a gel, a capsule, a powder, a granule, an elixir, a lozenge, a suppository, or an injection (including injection solution, lyophilized powder) and so on. In some embodiments, the medicament is an injection solution or a lyophilized powder.

In certain preferred embodiments, the pharmaceutical composition further comprises a pharmaceutically acceptable carrier or excipient. In certain preferred embodiments, the pharmaceutical composition comprises a stabilizer.

In the present invention, the ECHO25 and/or a modified form thereof, or the isolated nucleic acid molecule as described above can be administered to a subject by any suitable administration route. In some cases, the route of administration of the ECHO25 and/or a modified form thereof, or the isolated nucleic acid molecules as described above, depends on the location and type of tumor. For example, for a solid tumor that is easily accessible, the virus or nucleic acid molecule is optionally administered by injection directly into the tumor (e.g., intratumoral injection); for a tumor of hematopoietic system, the virus or nucleic acid molecule can be administered by intravenous or other intravascular routes; for a tumor that is not easily accessible in the body (e.g., metastases), the virus or nucleic acid molecule can be administered systematically so that it can run over the whole body and thereby reaching the tumor (e.g., intravenous or intramuscular injection). Optionally, the virus or nucleic acid molecule of the present invention can be administrated via subcutaneous, intraperitoneal, intrathecal (e.g., for brain tumors), topical (e.g., for melanoma), oral (e.g., for oral or esophageal cancer), intranasal or inhalation spray (e.g., for lung cancer) routes and so on. In certain preferred embodiments, the ECHO25 and/or a modified form thereof as described above, or the isolated nucleic acid as described above, can be administered via intradermal, subcutaneous, intramuscular, intravenous, oral routes etc.

In certain preferred embodiments, the method further comprises administering an additional pharmaceutically active agent having antitumor activity. This additional pharmaceutically active agent may be administered before, concurrently with or after the administration of the ECHO25 and/or a modified form thereof, or an isolated nucleic acid molecule as described above.

In certain preferred embodiments, the additional pharmaceutically active agent includes an additional oncolytic virus, a chemotherapeutic agent, or an immunotherapeutic agent.

In the present invention, the additional oncolytic virus includes, but is not limited to, herpesvirus, adenovirus, parvovirus, reovirus, Newcastle disease virus, vesicular stomatitis virus, measles virus, or any combination thereof. The chemotherapeutic agent includes but is not limited to 5-fluorouracil, mitomycin, methotrexate, hydroxyurea, cyclophosphamide, dacarbazine, mitoxantrone, anthracyclines (such as epirubicin or doxorubicin), etoposide, platinum compounds (such as carboplatin or cisplatin), taxanes (such as paclitaxel or taxotere), or any combination thereof. The immunotherapeutic agents include, but are not limited to, immune check point inhibitors (such as anti-PD-1 antibody, anti-PD-L1 antibody or anti-CTLA-4 antibody), tumor-specific targeting antibodies (such as rituximab or Herceptin) or any combination thereof.

In certain preferred embodiments, the ECHO25 and/or a modified form thereof can be administered in any amount from 1 to $1\times10^{15}$ pfu/kg of the subject's body weight, for example, the ECHO25 and/or a modified form thereof is administered in an amount of at least $1\times10^{3}$ pfu/kg, at least $1\times10^{4}$ pfu/kg, $1\times10^{5}$ pfu/kg, $1\times10^{6}$ pfu/kg, at least $1\times10^{7}$ pfu/kg, at least $1\times10^{8}$ pfu/kg, at least $1\times10^{9}$ pfu/kg, at least $1\times10^{10}$ pfu/kg, at least $1\times10^{11}$ pfu/kg, or at least $1\times10^{12}$ pfu/kg of the subject's body weight. In certain preferred embodiments, the isolated nucleic acid molecule as described above can be administered in any amount of $3\times10^{10}$ to $3\times10^{11}$ virus genome copies per kg of the subject's body weight. In certain preferred embodiments, the ECHO25 and/or a modified form thereof or the isolated nucleic acid molecule as described above can be administered 3 times per day, 2 times per day, 1 time per day, once every 2 days or once per week, optionally the above dosage regimen can be repeated weekly or monthly as appropriate.

In certain preferred embodiments, the method further comprises administering an additional therapy. This additional therapy may be any therapy known for tumors, such as surgery, chemotherapy, radiation therapy, immunotherapy, hormone therapy or gene therapy. This additional therapy may be administered before, concurrently with, or after the administration of the method described above.

In certain preferred embodiments, the subject is a mammal, such as a human.

In certain preferred embodiments, the tumor is selected from the group consisting of gastric cancer, liver cancer, ovarian cancer (e.g., ovarian non-clear cell carcinoma), endometrial cancer, melanoma, prostate cancer, glioma, esophageal cancer, bladder cancer, lymphoma (e.g., histiocytic lymphoma), leukemia (e.g., chronic myeloid leukemia), rhabdomyosarcoma, colorectal cancer, non-small cell lung cancer (e.g., non-small cell lung adenocarcinoma), cervical cancer (e.g., HPV-negative cervical cancer), breast cancer (e.g., breast medullary carcinoma), kidney cancer (e.g., clear cell renal carcinoma), and pancreatic cancer.

In certain preferred embodiments, the tumor is gastric cancer, liver cancer, ovarian cancer (e.g., ovarian non-clear cell carcinoma), endometrial cancer, cervical cancer (e.g., HPV-negative cervical cancer), melanoma, breast cancer (e.g., breast medullary carcinoma), prostate cancer, glioma, esophageal cancer, bladder cancer, lymphoma (e.g., histiocytic lymphoma), or leukemia (e.g., chronic myeloid leukemia).

Pharmaceutical Composition

In a third aspect, the present invention provides a pharmaceutical composition comprising the ECHO25 and/or a modified form thereof as defined in the first or second aspect, or the isolated nucleic acid molecule as defined in the first or second aspect.

In certain preferred embodiments, the pharmaceutical composition may be in any form known in the medical arts. For example, the pharmaceutical composition may be in the form of a tablet, a pill, a suspension, an emulsion, a solution, a gel, a capsule, a powder, a granule, an elixir, a lozenge, a suppository, or an injection (including injection solution, lyophilized powder) and so on. In some embodiments, the medicament is an injection solution or a lyophilized powder.

In certain preferred embodiments, the pharmaceutical composition further comprises a pharmaceutically acceptable carrier or excipient. In certain preferred embodiments, the pharmaceutical composition comprises a stabilizer.

In certain preferred embodiments, the pharmaceutical composition optionally further comprises an additional pharmaceutically active agent. In a preferred embodiment, the additional pharmaceutically active agent is a medicament having antitumor activity, such as an additional oncolytic virus, a chemotherapeutic agent or an immunotherapeutic agent.

In certain preferred embodiments, the pharmaceutical composition is used in treatment of a tumor in a subject.

In certain preferred embodiments, the subject is a mammal, such as a human.

In certain preferred embodiments, the tumor is selected from the group consisting of gastric cancer, liver cancer, ovarian cancer (e.g., ovarian non-clear cell carcinoma), endometrial cancer, melanoma, prostate cancer, glioma, esophageal cancer, bladder cancer, lymphoma (e.g., histiocytic lymphoma), leukemia (e.g., chronic myeloid leukemia), rhabdomyosarcoma, colorectal cancer, non-small cell lung cancer (e.g., non-small cell lung adenocarcinoma), cervical cancer (e.g., HPV-negative cervical cancer), breast cancer (e.g., breast medullary carcinoma), kidney cancer (e.g., clear cell renal carcinoma), and pancreatic cancer.

In certain preferred embodiments, the tumor is gastric cancer, liver cancer, ovarian cancer (e.g., ovarian non-clear cell carcinoma), endometrial cancer, cervical cancer (e.g., HPV-negative cervical cancer), melanoma, breast cancer (e.g., breast medullary carcinoma), prostate cancer, glioma, esophageal cancer, bladder cancer, lymphoma (e.g., histiocytic lymphoma), or leukemia (e.g., chronic myeloid leukemia).

Modified ECHO25

In a fourth aspect, the present invention provides a modified ECHO25, which has a substitution of the internal ribosome entry site (IRES) sequence in the 5'UTR with an internal ribosome entry site sequence of human rhinovirus 2 (HRV2) as compared to a wild-type ECHO25.

In certain preferred embodiments, the internal ribosome entry site sequence of human rhinovirus 2 (HRV2) is shown in SEQ ID NO: 2.

In certain preferred embodiments, the genomic sequence of the wild-type ECHO25 has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence as shown in SEQ ID NO: 12. In certain preferred embodiments, the genomic sequence of the wild-type ECHO25 is a nucleotide sequence as shown in SEQ ID NO: 12.

In certain preferred embodiments, the cDNA sequence of the wild-type ECHO25 has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence as shown in SEQ ID NO: 1. In certain preferred embodiments, the cDNA sequence of the wild-type ECHO25 is a nucleotide sequence as shown in SEQ ID NO: 1.

In certain preferred embodiments, the modified ECHO25 comprises an exogenous nucleic acid.

In certain preferred embodiments, the exogenous nucleic acid encodes a cytokine (e.g., a GM-CSF, preferably a human GM-CSF), or an antitumor protein or polypeptide (e.g., a scFv against PD-1 or PD-L1, preferably a scFv against human PD-1 or PD-L1). In certain preferred embodiments, the exogenous nucleic acid is inserted between the 5'UTR and the VP4 gene, or between the VP1 gene and the 2A gene of the genome of the modified ECHO25.

In certain preferred embodiments, the exogenous nucleic acid comprises a target sequence of microRNA (miRNA) (e.g., miR-133 or miR-206). In certain preferred embodiments, the target sequence of microRNA is inserted in the 3' untranslated region (3'UTR) of the genome of the modified ECHO25.

In certain preferred embodiments, the exogenous nucleic acid comprises a target sequence of one or more (e.g., 2, 3, or 4) microRNA as described above. In certain preferred embodiments, the exogenous nucleic acid comprises a target sequence of miR-133 and/or miR-206. In certain preferred embodiments, the target sequence of miR-133 is shown in SEQ ID NO: 3. In certain preferred embodiments, the target sequence of miR-206 is shown in SEQ ID NO: 4.

In certain preferred embodiments, the modified ECHO25 comprises an insertion of at least one exogenous nucleic acid as described above.

In certain preferred embodiments, the genomic sequence of the modified ECHO25 has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence as shown in SEQ ID NO: 13. In certain preferred embodiments, the genomic sequence of the modified ECHO25 is a nucleotide sequence as shown in SEQ ID NO: 13.

In certain preferred embodiments, the cDNA sequence of the modified ECHO25 has a sequence identity of at least 70%, at least 80%, at least 85%, at least 90%, at least 80% 91%, at least 92%, at least 93%, at least 94%, at least 95%, at least 96%, at least 97%, at least 98%, at least 99%, or 100% to a nucleotide sequence as shown in SEQ ID NO: 8. In certain preferred embodiments, the cDNA sequence of the modified ECHO25 is a nucleotide sequence as shown in SEQ ID NO: 8.

In the present invention, the modified ECHO25 can be obtained by reverse genetics technology, and the reverse genetics technology is known in the art, for example, see Yang L S, Li S X, Liu Y J, et al Virus Res, 2015, 210: 165-168; Hou W H, Yang L S, Li S X, et al. Virus Res, 2015, 205: 41-44; which are incorporated herein by reference in their entirety. In such embodiments, the modified ECHO25 is typically obtained by modifying the cDNA of wild-type ECHO25 (e.g., by insertion of an exogenous nucleic acid, deletion or mutation of an endogenous gene, or mutation in a non-translated region).

In the present invention, the modified ECHO25 may be subjected to a pretreatment to reduce or eliminate an immune response against the virus in a subject, wherein the pretreatment may comprise: packaging the ECHO25 in a liposome or micelle, and/or using a protease (e.g., chymotrypsin or trypsin) to remove a capsid protein of the virus to reduce a humoral and/or cellular immunity against the virus in the host.

In the present invention, the modified ECHO25 can be serially passaged for adaptation in tumor cells. In certain preferred embodiments, the tumor cells may be tumor cell lines or tumor cell strains known in the art, or tumor cells obtained by surgical resection or clinical isolation from an individual (e.g., a subject) having a tumor. In certain preferred embodiments, the modified ECHO25 is serially passaged for adaptation in tumor cells obtained from an individual (e.g., a subject) having a tumor. In certain preferred embodiments, the tumor cells are obtained by surgical resection or clinical isolation from an individual (e.g., a subject) having a tumor. In certain preferred embodiments, the method for serial passaging for adaptation comprises a plurality of (e.g., at least 5, at least 10, at least 15, at least 20) cycles consisting of the following processes: 1) infecting a target tumor cell with a virus; 2) harvesting the virus in a supernatant; and 3) reinfecting a fresh target tumor cell with the obtained virus.

In certain preferred embodiments, the modified ECHO25 is used in treatment of a tumor in a subject, or in the manufacture of a medicament for treating a tumor in a subject.

In certain preferred embodiments, the tumor is selected from the group consisting of gastric cancer, liver cancer, ovarian cancer (e.g., ovarian non-clear cell carcinoma), endometrial cancer, melanoma, prostate cancer, glioma, esophageal cancer, bladder cancer, lymphoma (e.g., histiocytic lymphoma), leukemia (e.g., chronic myeloid leukemia), pharyngeal squamous cell carcinoma, thyroid cancer, rhabdomyosarcoma, colorectal cancer, non-small cell lung cancer (e.g., non-small cell lung adenocarcinoma), cervical cancer (e.g., HPV-negative cervical cancer), breast cancer (e.g., breast medullary carcinoma), kidney cancer (e.g., clear cell renal carcinoma), and pancreatic cancer.

In certain preferred embodiments, the tumor is gastric cancer, liver cancer, ovarian cancer (e.g., ovarian non-clear cell carcinoma), endometrial cancer, cervical cancer (e.g., HPV-negative cervical cancer), melanoma, breast cancer (e.g., breast medullary carcinoma), prostate cancer, glioma, esophageal cancer, bladder cancer, lymphoma (e.g., histiocytic lymphoma), leukemia (e.g., chronic myeloid leukemia), pharyngeal squamous cell carcinoma or thyroid cancer.

In certain preferred embodiments, the modified ECHO25 is used in treatment of a tumor in a subject, or in manufacture of a medicament for treating a tumor in a subject, wherein the tumor is pharyngeal squamous cell carcinoma or thyroid cancer.

In certain preferred embodiments, the subject is a mammal, such as a human.

In a fifth aspect, the invention provides an isolated nucleic acid molecule comprising a sequence selected from:

(1) a genomic sequence or cDNA sequence of the modified ECHO25 according to the fourth aspect; and (2) a complementary sequence of the genomic sequence or cDNA sequence.

In certain preferred embodiments, the isolated nucleic acid molecule consists of a genomic sequence or cDNA sequence of the modified ECHO25 as described above, or a complementary sequence of the genomic sequence or cDNA sequence.

In certain preferred embodiments, the isolated nucleic acid molecule has the genomic sequence of the modified ECHO25 as described above. In certain preferred embodiments, the isolated nucleic acid molecule is RNA. In certain preferred embodiments, the isolated nucleic acid molecule has a nucleotide sequence as shown in SEQ ID NO: 13.

In certain preferred embodiments, the isolated nucleic acid molecule is a vector (e.g. a cloning vector or an expression vector) comprising a genomic sequence or cDNA sequence of the ECHO25 or a modified form thereof as described above, or a complementary sequence of the genomic sequence or cDNA sequence. In certain preferred embodiments, the isolated nucleic acid molecule is a vector (e.g., a cloning vector or an expression vector) comprising a cDNA sequence of the ECHO25 or a modified form thereof as described above, or a complementary sequence of the cDNA sequence.

In certain preferred embodiments, the isolated nucleic acid molecule comprises a complementary sequence of a genomic sequence of the modified ECHO25 as described above.

In certain preferred embodiments, the complementary sequence is complementary to a nucleotide sequence selected from:

(1) a nucleotide sequence as shown in SEQ ID NO: 13; and (2) a nucleotide sequence having a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence as shown in SEQ ID NO: 13.

In certain preferred embodiments, the isolated nucleic acid molecule comprises a complementary sequence of a cDNA sequence of the modified ECHO25 as described above. In certain preferred embodiments, the complementary sequence is complementary to a nucleotide sequence selected from:

(1) a nucleotide sequence as shown in SEQ ID NO: 8; and (2) a nucleotide sequence having a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to a nucleotide sequence as shown in SEQ ID NO: 8.

In certain preferred embodiments, the isolated nucleic acid molecule has a nucleotide sequence as shown in SEQ ID NO: 13, or the isolated nucleic acid molecule is a vector (e.g., a cloning vector or an expression vector) comprising a nucleotide sequence as shown in SEQ ID NO: 8 or a complementary sequence thereof.

In the present invention, the isolated nucleic acid molecule can be delivered by any means known in the art, for example, a naked nucleic acid molecule (e.g., naked RNA) can be directly injected, or a non-viral delivery system can be used. The non-viral delivery system can be obtained from a variety of materials well known in the art, including, but not limited to, the materials described in detail in "Yin H, et al. Nat Rev Genet. 2014 August; 15 (8): 541-55." and "Riley M K, Vermerris W. Nanomaterials (Basel). 2017 Apr. 28; 7(5). Pii: E94.", which are incorporated herein by reference in their entirety, such as liposomes, inorganic nanoparticles (such as gold nanoparticles), polymers (such as PEG), and so on.

In certain preferred embodiments, the isolated nucleic acid molecule is used in treatment of a tumor in a subject, or in the manufacture of a medicament for treating a tumor in a subject.

In certain preferred embodiments, the tumor is selected from the group consisting of gastric cancer, liver cancer, ovarian cancer (e.g., ovarian non-clear cell carcinoma), endometrial cancer, melanoma, prostate cancer, glioma, esophageal cancer, bladder cancer, lymphoma (e.g., histiocytic lymphoma), leukemia (e.g., chronic myeloid leukemia), pharyngeal squamous cell carcinoma, thyroid cancer, rhabdomyosarcoma, colorectal cancer, non-small cell lung cancer (e.g., non-small cell lung adenocarcinoma), cervical cancer (e.g., HPV-negative cervical cancer), breast cancer (e.g., breast medullary carcinoma), kidney cancer (e.g., clear cell renal carcinoma), and pancreatic cancer.

In certain preferred embodiments, the tumor is gastric cancer, liver cancer, ovarian cancer (e.g., ovarian non-clear cell carcinoma), endometrial cancer, cervical cancer (e.g., HPV-negative cervical cancer), melanoma, breast cancer (e.g., breast medullary carcinoma), prostate cancer, glioma, esophageal cancer, bladder cancer, lymphoma (e.g., histiocytic lymphoma), leukemia (e.g., chronic myeloid leukemia), pharyngeal squamous cell carcinoma or thyroid cancer.

In certain preferred embodiments, the isolated nucleic acid molecule is used in treatment of a tumor in a subject, or in the manufacture of a medicament for treating a tumor in a subject, wherein the tumor is pharyngeal squamous cell carcinoma or thyroid cancer.

In certain preferred embodiments, the subject is a mammal, such as a human.

In another aspect, the present invention also relates to a pharmaceutical composition comprising the modified ECHO25 according to the fourth aspect, or the isolated nucleic acid molecule according to the fifth aspect.

In certain preferred embodiments, the pharmaceutical composition may be in any form known in the medical arts. For example, the pharmaceutical composition may be a tablet, a pill, a suspension, an emulsion, a solution, a gel, a capsule, a powder, a granule, an elixir, a lozenge, a suppository, or an injection (including injection solution, lyophilized powder) and so on. In some embodiments, the medicament is an injection solution or a lyophilized powder.

In certain preferred embodiments, the pharmaceutical composition further comprises a pharmaceutically acceptable carrier or excipient. In certain preferred embodiments, the pharmaceutical composition comprises a stabilizer.

In certain preferred embodiments, the pharmaceutical composition optionally further comprises an additional pharmaceutically active agent. In a preferred embodiment, the additional pharmaceutically active agent is a medicament having antitumor activity, such as an additional oncolytic virus, a chemotherapeutic agent or an immunotherapeutic agent.

In another aspect, the present invention also relates to use of the modified ECHO25 according to the fourth aspect, or the isolated nucleic acid molecule according to the fifth aspect, in treatment of a tumor in a subject, or in the manufacture of a medicament for treating a tumor in a subject.

In certain preferred embodiments, the tumor is selected from the group consisting of gastric cancer, liver cancer, ovarian cancer (e.g., ovarian non-clear cell carcinoma), endometrial cancer, melanoma, prostate cancer, glioma, esophageal cancer, bladder cancer, lymphoma (e.g., histiocytic lymphoma), leukemia (e.g., chronic myeloid leukemia), pharyngeal squamous cell carcinoma, thyroid cancer, rhabdomyosarcoma, colorectal cancer, non-small cell lung cancer (e.g., non-small cell lung adenocarcinoma), cervical cancer (e.g., HPV-negative cervical cancer), breast cancer (e.g., breast medullary carcinoma), kidney cancer (e.g., clear cell renal carcinoma), and pancreatic cancer.

In certain preferred embodiments, the tumor is gastric cancer, liver cancer, ovarian cancer (e.g., ovarian non-clear cell carcinoma), endometrial cancer, cervical cancer (e.g., HPV-negative cervical cancer), melanoma, breast cancer (e.g., breast medullary carcinoma), prostate cancer, glioma, esophageal cancer, bladder cancer, lymphoma (e.g., histiocytic lymphoma), leukemia (e.g., chronic myeloid leukemia), pharyngeal squamous cell carcinoma or thyroid cancer.

In certain preferred embodiments, the isolated nucleotide sequence molecule is used in treatment of a tumor in a subject, or in the manufacture of a medicament for treating a tumor in a subject, wherein the tumor is pharyngeal squamous cell carcinoma or thyroid cancer.

In certain preferred embodiments, the subject is a mammal, such as a human.

In another aspect, the invention also relates to a method for treating a tumor, comprising a step of administering to a subject in need thereof an effective amount of the modified ECHO25 as described in the fourth aspect, or the isolated nucleic acid molecule according to the fifth aspect.

In certain preferred embodiments, the tumor is selected from the group consisting of gastric cancer, liver cancer, ovarian cancer (e.g., ovarian non-clear cell carcinoma), endometrial cancer, melanoma, prostate cancer, glioma, esophageal cancer, bladder cancer, lymphoma (e.g., histiocytic lymphoma), leukemia (e.g., chronic myeloid leukemia), pharyngeal squamous cell carcinoma, thyroid cancer, rhabdomyosarcoma, colorectal cancer, non-small cell lung cancer (e.g., non-small cell lung adenocarcinoma), cervical cancer (e.g., HPV-negative cervical cancer), breast cancer (e.g., breast medullary carcinoma), kidney cancer (e.g., clear cell renal carcinoma), and pancreatic cancer.

In certain preferred embodiments, the tumor is gastric cancer, liver cancer, ovarian cancer (e.g., ovarian non-clear cell carcinoma), endometrial cancer, cervical cancer (e.g., HPV-negative cervical cancer), melanoma, breast cancer (e.g., breast medullary carcinoma), prostate cancer, glioma, esophageal cancer, bladder cancer, lymphoma (e.g., histiocytic lymphoma), leukemia (e.g., chronic myeloid leukemia), pharyngeal squamous cell carcinoma or thyroid cancer.

In certain preferred embodiments, the tumor is pharyngeal squamous cell carcinoma or thyroid cancer.

In certain preferred embodiments, the subject is a mammal, such as a human.

DEFINITION OF TERMS

In the present invention, unless otherwise stated, scientific and technical terms used herein have meanings commonly understood by those skilled in the art. In addition, the laboratory procedures of cell culture, biochemistry, cell biology, nucleic acid chemistry and the like used herein are all routine steps widely used in the corresponding fields. Meanwhile, in order to better understand the present invention, definitions and explanations of related terms are provided below.

As used herein, the term "echovirus 25 (ECHO25)" refers to one kind of the species Enterovirus B of the genus Enteroviruses of the family Picornaviridae, the genome of which is a single-stranded positive-sense RNA, consisting of a 5' non-coding region (5'UTR), an open reading frame (ORF), a 3' non-coding region (3'UTR), and a poly(A) tail; wherein the ORF encodes a precursor polyprotein, which can be hydrolyzed and cleaved by its protease to produce structural proteins VP1 to VP4 and non-structural proteins 2A, 2B, 2C, 3A, 3B, 3C and 3D. In order to more clearly describe the present invention, the nucleic acid sequences in the ECHO25 genome corresponding to the above proteins are called VP1 gene, VP2 gene, VP3 gene, VP4 gene, 2A gene, 2B gene, 2C gene, 3A gene, 3B gene, 3C gene, and 3D gene, respectively. In the present invention, the expression "echovirus 25 (ECHO25)" refers to a wild-type ECHO25, which can be isolated from sources in nature and has not been intentionally and artificially modified, examples of which include, but are not limited to, prototype strain AY302549(JV-4), and various clinical isolates (for example, the clinical isolate described in Example 1 of the present invention). The genomic sequence or cDNA sequence of the wild-type ECHO25 is well known in the art and can be found in various public databases (for example, GenBank accession number KP099941.1).

As used herein, the term "modified form" of a virus refers to a modified virus obtained by modifying a wild-type virus, which retains the desired activity (e.g., oncolytic activity) of the wild-type virus. In the present invention, a "modified form" of ECHO25 includes, but is not limited to, a modified ECHO25 virus, the genome sequence of which has a substitution, insertion, or deletion of one or more nucleotides as compared to that of the wild-type ECHO25, and at least retains the oncolytic activity of ECHO25.

As used herein, the term "oncolytic virus" refers to a virus capable of infecting a tumor cell, replicating in the tumor cell, causing the tumor cell death, lysis, or blocking tumor cell growth. Preferably, the virus has minimal toxic effects on a non-tumor cell.

As used herein, the term "tumor-specific" refers to selectively exhibiting a biological function or activity within a tumor cell. For example, in the present invention, when the term "tumor specificity" is used to describe the killing selectivity of a virus, it means that the virus is capable of selectively killing a tumor cell without killing or substantially killing a non-tumor cell, or the virus is more effective in killing a tumor cell than killing a non-tumor cell.

As used herein, the term "oncolytic activity" primarily includes tumor killing activity. When describing the oncolytic activity of a virus, the oncolytic activity of the virus can typically be measured by indicators such as the virus' ability to infect a tumor cell, ability to replicate in a tumor cell, and/or ability to kill a tumor cell. The oncolytic activity of a virus can be measured using any method known in the art. For example, the ability of a virus to infect a tumor cell can be evaluated by measuring the viral dose required to infect a given percentage of tumor cells (for example, 50% of the cells); the ability to replicate in a tumor cell can be evaluated by measuring the growth of the virus in the tumor cell; the ability to kill a tumor cell can be evaluated by monitoring cytopathic effect (CPE) or measuring tumor cell activity.

As used herein, the expression "cDNA sequence of ECHO25" means the DNA form of the viral genomic RNA sequence, which differs from the RNA sequence only in that the ribonucleotides in the RNA sequence are replaced by corresponding deoxyribonucleotides, for example, uracil ribonucleotides (UMP) are replaced by thymine deoxyribonucleotides (dTMP).

As used herein, the term "exogenous nucleic acid" refers to an artificially introduced nucleotide sequence that is foreign to the original sequence. Exogenous nucleic acid includes, but is not limited to, any gene or nucleotide sequence not found in the viral genome. However, in the present invention, it is particularly preferred that the exogenous nucleic acid is composed of at most 1500, such as at most 1200, and at most 1000 nucleotides. In some cases, preferably, the exogenous nucleic acid encodes a protein or polypeptide having antitumor killing activity, such as a cytokine, or an antitumor protein or polypeptide; or, the exogenous nucleic acid comprises a target sequence of microRNA (miRNA). In the present invention, the microRNA is preferably a microRNA having an expression level in a tumor cell significantly lower than that in a normal cell and/or having obvious tissue specificity. Examples of the microRNA include, but are not limited to, miR-122, miR-192, miR-483, etc., which are specifically expressed in liver tissue; miR-1, miR-133a/b, miR-208, etc., which are specifically expressed in heart; miR-192, miR-196a/b, miR-204, miR-215, etc., which are specifically expressed in kidney tissue; miR-133a/b, miR-206, etc., which are specifically expressed in muscle tissue; miR-124a, miR-125a/b, miR-128a/b, miR-138, etc., which are specifically expressed in brain tissue; and miR-34, miR-122a, miR-26a, which are under-expressed in liver tumor tissue; miR-34, which is under-expressed in kidney tumor tissue; miR-143, miR-133a/b, which are under-expressed in bladder tumor tissue; miR-Let-7, miR-29, which are under-expressed in lung tumor tissue; and so on (see, for example, Ruiz A J and Russell S J. MicroRNAs and oncolytic viruses. [J]. Curr Opin Virol, 2015, 13: 40-48; which is incorporated herein by reference in its entirety).

In the present invention, when the modified ECHO25 comprises the target sequence of microRNA described above, it is regulated by the microRNA in a cell/tissue in which the microRNA is highly expressed or specifically expressed, so that replication of the oncolytic virus is attenuated and even its killing activity is lost, while in a tumor cell/tissue in which the microRNA is under-expressed or even not expressed, the oncolytic virus can normally replicate and thus kill the tumor cell.

As used herein, the term "cytokine" has a meaning well known to those skilled in the art. However, in the present invention, when the oncolytic virus of the present invention is used to treat a tumor, it is particularly preferred that the cytokine is a cytokine that can be used for tumor treatment. Examples of "cytokines" include, but are not limited to, interleukins (e.g., IL-2, IL-12, and IL-15), interferons (e.g., IFNα, IFNβ, IFNγ), tumor necrosis factors (e.g., TNFα), and colony-stimulating factors (e.g., GM-CSF), and any combination thereof (see, for example, Ardolino M, Hsu J, Raulet D H. Cytokine treatment in cancer immunotherapy [J]. Oncotarget, 2015, 6 (23): 19346-19347).

As used herein, the term "antitumor protein or polypeptide" refers to a protein or polypeptide having antineoplastic activity, including but not limited to: (1) proteins or polypeptides having toxicity to cells, capable of inhibiting cell proliferation, or inducing apoptosis, examples thereof include, but are not limited to, thymidine kinase TK (TK/GCV), TRAIL, and FasL (see, for example, Candolfi M, King G D, Muhammad A G, et al. Evaluation of proapototic transgenes to use in combination with Flt3L in an immune-stimulatory gene therapy approach for Glioblastoma multiforme (GBM) [J]. FASEB J, 2008, 22: 1077.13); (2) proteins or polypeptides having immunotherapeutic effects, examples thereof include, but are not limited to, single chain antibody (scFv) against cytotoxic T lymphocyte-associated antigen 4 (anti-CTLA-4), against programmed death receptor 1 (anti-PD-1), and against programmed death ligand 1 (anti-PDL-1) (see, for example, Nolan E, Savas P, Policheni A N, et al. Combined immune checkpoint blockade as a therapeutic strategy for BRCA1-mutated breast cancer [J]. Science Trans Med, 2017, 9: eaal 4922; which is incorporated herein by reference in its entirety); (3) proteins or polypeptides that inhibit tumor angiogenesis, examples thereof include, but are not limited to, single-chain antibody (scFv) against vascular endothelial growth factor (anti-VEGF), VEGF-derived polypeptides (e.g., $_D$(LPR), KSVRGKGKGQKRKRKKSRYK, etc.) and ATN-161 (see, for example, Rosca E V, Koskimaki J E, Rivera C G, et al. Anti-angiogenic peptides for cancer therapeutics [J]. Curr Pharm Biotechnol, 2011, 12 (8): 1101-1116; which is incorporated herein by reference in its entirety).

As used herein, the term "scFv" refers to a single polypeptide chain comprising a heavy chain variable region (VH) and a light chain variable region (VL), wherein the VL and VH are linked by a linker (see, for example, Bird et al., Science 242: 423-426 (1988); Huston et al., Proc. Natl. Acad. Sci. USA 85: 5879-5883 (1988); and Pluckthun, The Pharmacology of Monoclonal Antibodies, No. Volume 113, edited by Roseburg and Moore, Springer-Verlag, New York, pp. 269-315 (1994)). Such scFv molecule may have a general structure: $NH_2$-VL-linker-VH-COOH or $NH_2$-VH-linker-VL-COOH.

As used herein, the term "identity" refers to the match degree between two polypeptides or between two nucleic acids. When two sequences for comparison have the same monomer sub-unit of base or amino acid at a certain site (e.g., each of two DNA molecules has an adenine at a certain site, or each of two proteins/polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by for example using a computer program such as Align program (DNAstar, Inc.) which is based on the method of Needleman, et al. (J. Mol. Biol. 48:443-453, 1970). The percentage of identity between two amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, and with a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and with a gap weight of 16, 14, 12, 10, 8, 6, or 4 and a length weight of 1, 2, 3, 4, 5, or 6.

As used herein, the term "vector" refers to a nucleic acid vehicle into which a polynucleotide can be inserted. When a vector enables expression of a protein encoded by an inserted polynucleotide, the vector is referred to as an expression vector. A vector can be introduced into a host cell by transformation, transduction, or transfection, so that the genetic material elements carried by the vector can be expressed in the host cell. The vector is well known to those skilled in the art and includes, but is not limited to: plasmids; phagemids; cosmids; artificial chromosomes, such as yeast artificial chromosomes (YAC), bacterial artificial chromosomes (BAC) or P1-derived artificial chromosomes (PAC); bacteriophages such as λphage or M13 phage and animal viruses. Animal viruses that can be used as vectors include, but are not limited to, retroviruses (including lentiviruses), adenoviruses, adeno-associated viruses, herpesviruses (such as herpes simplex virus), poxviruses, baculoviruses, papillomaviruses, and papovaviruses (such as SV40). A vector may contain a variety of elements that control expression, including, but not limited to, promoter sequences, transcription initiation sequences, enhancer sequences, elements for selection, and reporter genes. In addition, the vector may contain a replication initiation site.

As used herein, the term "internal ribosome entry site (IRES)" refers to a nucleotide sequence located in a messenger RNA (mRNA) sequence that is capable of initiating translation without the need for the 5' cap structure. IRES is usually located in the 5' untranslated region (5'UTR), but may also be located elsewhere in the mRNA.

As used herein, the term "human rhinovirus 2 (HRV2)" refers to a virus of picornaviridae family, the genomic or cDNA sequence of which is well known in the art and can be found in various public databases (e.g., GenBank accession number X02316.1).

As used herein, the expression "a nucleic acid molecule comprising a genomic sequence of ECHO25 or a modified form thereof" or "a nucleic acid molecule comprises a genomic sequence of ECHO25 or a modified form thereof" has the meaning commonly understood by those skilled in the art, that is, when the nucleic acid molecule is DNA, the nucleic acid molecule comprises a genomic sequence of ECHO25 or a modified form thereof in form of DNA; when the nucleic acid molecule is RNA, the nucleic acid molecule comprises a genomic sequence of ECHO25 or a modified form thereof.

As used herein, the term "pharmaceutically acceptable carrier and/or excipient" refers to a carrier and/or excipient that is pharmacologically and/or physiologically compatible with the subject and the active ingredient, which is well known in the art (see, for example, Remington's Pharmaceutical Sciences. Edited by Gennaro A R, 19th ed. Pennsylvania: Mack Publishing Company, 1995), and includes, but is not limited to: pH adjusting agents, surfactants, ionic strength enhancers, agents to maintain osmotic pressure, agents to delay absorption, diluents, adjuvants, preservatives, stabilizers, etc. For example, pH adjusting agents include, but are not limited to, phosphate buffered saline. Surfactants include, but are not limited to, cationic, anionic or non-ionic surfactants, such as Tween-80. Ionic strength enhancers include, but are not limited to, sodium chloride. Agents that maintain osmotic pressure include, but are not limited to, sugar, NaCl, and the like. Agents that delay absorption include, but are not limited to, monostearate and gelatin. Diluents include, but are not limited to, water, aqueous buffers (such as buffered saline), alcohols and polyols (such as glycerol), and the like. Adjuvants include, but are not limited to, aluminum adjuvants (such as aluminum hydroxide), Freund's adjuvants (such as complete Freund's adjuvant), and the like. Preservatives include, but are not limited to, various antibacterial and antifungal agents, such as thimerosal, 2-phenoxyethanol, parabens, trichloro-t-butanol, phenol, sorbic acid, and the like. Stabilizers have the meaning commonly understood by those skilled in the art, which can stabilize the desired activity (such as oncolytic activity) of the active ingredients in the drug, including but not limited to sodium glutamate, gelatin, SPGA, sugars (e.g., sorbitol, mannitol, starch, sucrose, lactose, dextran, or glucose), amino acids (e.g., glutamic acid, glycine), proteins (e.g., dried whey, albumin, or casein) or their degradation products (e.g., lactalbumin hydrolysates).

As used herein, the term "treating" refers to treating or curing a disease (e.g., a tumor), delaying the onset of symptoms of a disease (e.g., a tumor), and/or delaying the development of a disease (e.g., a tumor).

As used herein, the term "effective amount" refers to an amount that can effectively achieve the intended purpose. For example, a therapeutically effective amount can be an amount effective or sufficient to treat or cure a disease (e.g., a tumor), delay the onset of symptoms of a disease (e.g., a tumor), and/or delay the development of a disease (e.g., a tumor). Such an effective amount can be easily determined by a person skilled in the art or a doctor, and can be related to the intended purpose (such as treatment), the general health condition, age, gender, weight of the subject, severity, complications, administration route of the disease to be treated. The determination of such an effective amount is well within the capabilities of those skilled in the art.

As used herein, the term "subject" refers to a mammal, such as a primate mammal, such as a human. In certain embodiments, the subject (e.g., a human) has a tumor, or is at risk for having a tumor.

The Beneficial Effects of the Present Invention

Compared with the prior art, the technical solution of the present invention has at least the following beneficial effects:

The inventors of the present application have found for the first time that echovirus 25 (ECHO25) has good killing activity against specific tumors. Based on this finding, the present invention further provides an ECHO25-based oncolytic virus, which has better tumor-killing activity and higher tumor specificity, thus can be used alone for the treatment of tumors, and can also be used as a supplementary method for traditional tumor treatment, or as a therapy when other treatments were absent.

The ECHO25 or a modified form thereof of the present invention has little or no effect on normal cells, and does not induce an immunogenic response against the virus in a subject (for example, a human), and thus can be safely administered to a subject (for example, a human). Therefore, the ECHO25 or a modified form thereof of the present invention has great clinical value.

The embodiments of the present invention will be described in detail below with reference to the drawings and examples, but those skilled in the art will understand that the following drawings and examples are only used to illustrate the present invention, rather than limiting the scope of the present invention. Various objects and advantageous aspects of the present invention will become apparent to those skilled in the art from the following detailed description of drawings and the preferred embodiments.

SEQUENCE INFORMATION

Figure 1:
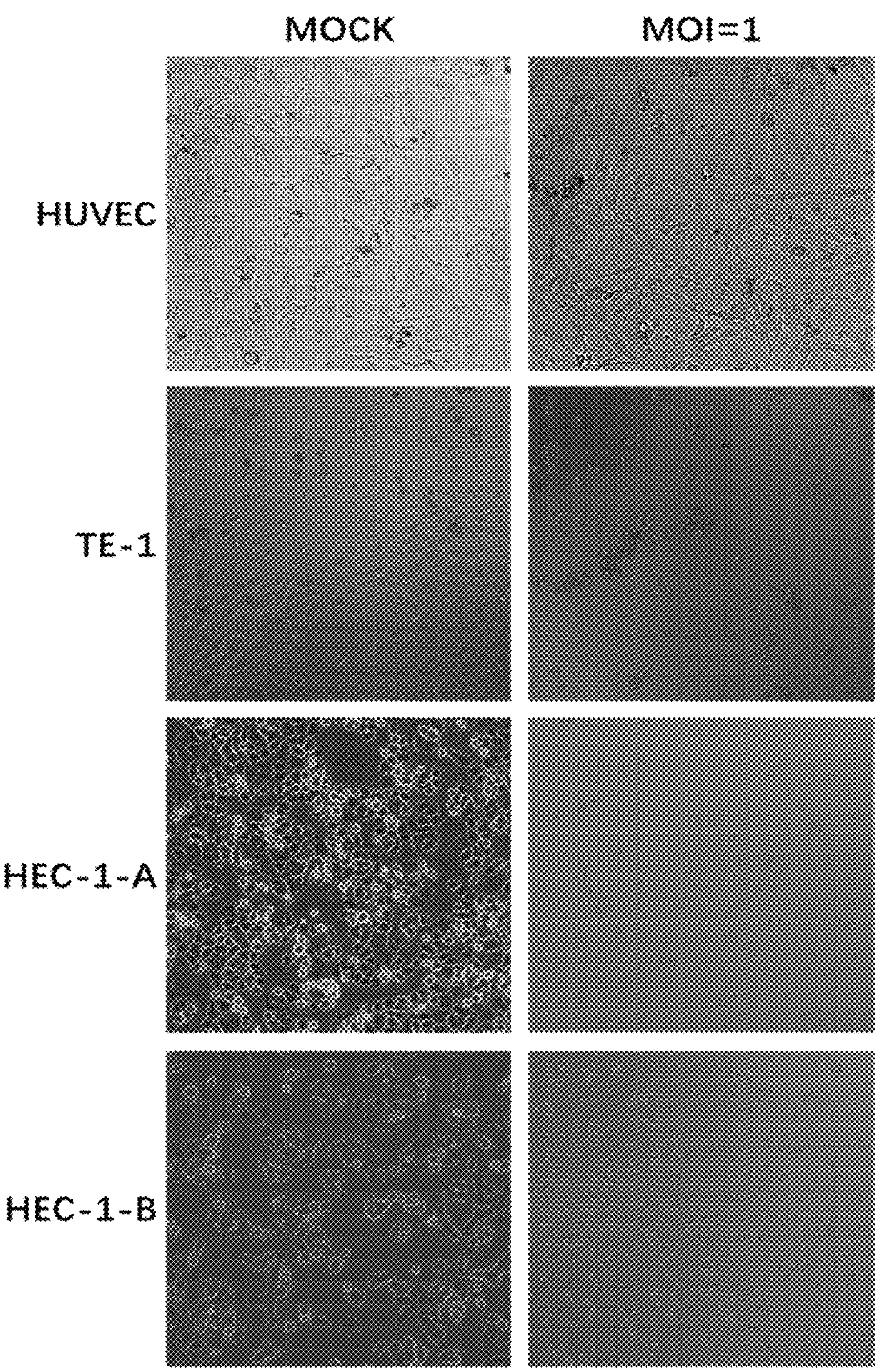
FIG. 1 shows photomicrographs of the in vitro killing tests of the wild-type ECHO25 on human umbilical vein endothelial cell line HUVEC, human esophageal cancer cell line TE-1, human endometrial cancer cell lines HEC-1-A and HEC-1-B in Example 2, in which MOCK represents cells that are not infected with the virus. The results showed that the ECHO25 had significant oncolytic effects on human tumor cell lines TE-1, HEC-1-A, and HEC-1-B after 72 hours of infection at a multiplicity of infection (MOI) of 1, but had no effect on HUVEC as human non-tumor cells.

Information of a part of sequences involved in the present invention is provided in Table 1 as below.

TABLE 1

Sequence description

| SEQ ID NO: | Description |
|---|---|
| 1 | cDNA sequence of wild type ECHO25 (ECHO25-WT) |
| 2 | RNA sequence of the internal ribosome entry site of human rhinovirus 2 (HRV2) |
| 3 | RNA sequence of miR-133 target sequence |
| 4 | RNA sequence of miR-206 target sequence |
| 5 | RNA sequence of tandem sequence of miR-133 target sequence and miR-206 target sequence |
| 6 | DNA sequence of human granulocyte-macrophage colony-stimulating factor (GM-CSF) gene |
| 7 | DNA sequence of single chain antibody against human programmed death receptor 1 (Anti-PD-1 scFv) |
| 8 | cDNA sequence of one modified form of ECHO25 (ECHO25-HRV2) |
| 9 | cDNA sequence of one modified form of ECHO25 (ECHO25-miR133&206T) |
| 10 | cDNA sequence of one modified form of ECHO25 (ECHO25-GM-CSF) |
| 11 | cDNA sequence of one modified form of ECHO25 (ECHO25-Anti-PD1) |
| 12 | Genomic sequence of wild-type ECHO25 (ECHO25-WT) |
| 13 | Genomic sequence of one modified form of ECHO25 (ECHO25-HRV2) |
| 14 | Genomic sequence of one modified form of ECHO25 (ECHO25-miR133 & 206T) |
| 15 | Genomic sequence of one modified form of ECHO25 (ECHO25-GM-CSF) |
| 16 | Genomic sequence of one modified form of ECHO25 (ECHO25-Anti-PD1) |
| 17 | DNA sequence of miR-133 target sequence |
| 18 | DNA sequence of miR-206 target sequence |
| 19 | DNA sequence of tandem sequence of miR-133 target sequence and miR-206 target sequence |
| 20 | DNA sequence of the internal ribosome entry site sequence of human rhinovirus 2 (HRV2) |

Specific Models for Carrying Out the Invention

The present invention is now described with reference to the following examples which are intended to illustrate the present invention (rather than to limit the present invention).

Unless otherwise specified, the molecular biology experimental methods and immunoassays used in the present invention were carried out substantially by referring to the methods of J. Sambrooket al., Molecular Cloning: A Laboratory Manual, 2nd Edition, Cold Spring Harbor Laboratory Press, 1989, and F. M. Ausubelet a., Short Protocols in Molecular Biology, 3rd Edition, John Wiley & Sons, Inc., 1995; restriction enzymes were used under conditions recommended by the product manufacturer. If the specific conditions were not indicated in the examples, the conventional conditions or the conditions recommended by the manufacturer were used. If the reagents or instruments used were not specified by the manufacturer, they were all conventional products that were commercially available. Those skilled in the art will understand that the examples describe the present invention by way of example, and are not intended to limit the scope of protection claimed by the present invention. All publications and other references mentioned herein are incorporated by reference in their entirety.

Example 1: Obtainment and Preparation of ECHO25 and Modified Forms Thereof 1.1 Isolation of ECHO025 from Patient Clinical Samples (1) A throat swab and anal swab of patient were gained from the Center for Disease Control and Prevention of Xiamen City, China; African green monkey kidney cells (Vero cells; ATCC® Number: CCL-81™) were was kept by the National Institute of Diagnostics and Vaccine Development in Infectious Diseases, Xiamen University, China, and cultured in MEM medium containing 10% fetal bovine serum, glutamine, penicillin and streptomycin.

(2) Sample processing: the throat swab and anal swab of patient were sufficiently agitated in a sample preservation solution to wash off the virus and virus-containing cells adhering to the swabs, and then the sample preservation solution was subjected to a high speed centrifugation at 4000 rpm and 4° C. for 30 min;

(3) Inoculation and observation:

A) The Vero cells were plated in a 24-well plate with $1\times10^5$ cells/well. The growth medium (MEM medium, containing 10% fetal bovine serum, as well as glutamine, penicillin and streptomycin) was aspirated, and 1 mL of maintenance medium (MEM medium, containing 2% fetal calf serum, as well as glutamine, penicillin and streptomycin) was added in each well. Then, except the negative control wells, each well was inoculated with 50 μL of the sample supernatant, and cultured in an incubator at 37° C., 5% $CO_2$.

B) The cells were observed under a microscope every day for one week, and the occurrence of specific cytopathic effect (CPE) in the inoculated wells was recorded.

C) If the enterovirus-specific cytopathic effect appeared in the cells in the inoculated wells within 7 days, the cells and supernatant were collected and frozen at −80° C.; if no CPE appeared after 7 days, the cells were subjected to blind passage.

D) If CPE appeared within 6 blind passages, the cells and supernatant were collected and frozen at −80° C.; If CPE did not appear after 6 blind passages, the cells were determined as negative.

(4) Isolation and Cloning of Viruses:

RT-PCR (Hou et al., Virus Res 2015, 205: 41-44) and enzyme-linked immunospot method (ELISPOT) based on specific antibody (Li Shuxuan et al., Biotechnology News (2016) 27 (1): 52-57) were used to identify the viruses isolated from the clinical samples, and echovirus 25-positive culture was selected and subjected to at least 3 cloning experiments. The virus clones obtained by the limiting dilution method in each experiment were also identified by RT-PCR and ELISPOT, and the ECHO25-positive clones were selected for the next round of cloning. A single ECHO25 strain with strong growth viability was selected as a candidate oncolytic virus strain.

1.2 Obtainment of Rescued Strain of ECHO25 and Modified Forms Thereof by Infectious Cloning and Reverse Genetics Technology In this example, wild-type ECHO25 (SEQ ID NO: 1) was used as an example to show how to obtain ECHO25 and its modified form for the present invention through reverse genetics technology. The specific method was as follows.

(1) Construction of viral infectious clone: the cDNA sequence of wild-type ECHO25 (named ECHO25-WT) was shown in SEQ ID NO: 1, and its genomic RNA sequence was SEQ ID NO: 12; or gene insertion or replacement based on the cDNA (SEQ ID NO: 1) of ECHO25 was performed, comprising:

Modified form 1: the internal ribosome entry site sequence of wild-type ECHO25 was replaced with the internal ribosome entry site sequence of human rhinovirus 2 (which has a DNA sequence shown in SEQ ID NO: 20) to obtain the cDNA (SEQ ID NO: 8) of the recombinant virus (named as ECHO25-HRV2), which has a genomic RNA sequence shown as SEQ ID NO: 13;

Modified form 2: the tandem sequence (which has a DNA sequence shown in SEQ ID NO: 19) of miR-133 target sequence (which has a DNA sequence shown in SEQ ID NO: 17) and miR-206 target sequence (which has a DNA sequence shown in SEQ ID NO: 18) was inserted between 7337-7338 bp of the 3' untranslated region of the cDNA (SEQ ID NO: 1) of the wild-type ECHO25, to obtain the cDNA (SEQ D NO: 9) of the recombinant virus (named ECHO25-miR133 & 206T), which has a genomic RNA sequence shown as SEQ ID NO: 14;

Modified form 3: the human granulocyte-macrophage colony-stimulating factor (GM-CSF) gene (SEQ ID NO: 6) was inserted between the VP1 gene and 2A gene of the cDNA (SEQ ID NO: 1) of wild-type ECHO25 to obtain the cDNA (SEQ ID NO: 10) of the recombinant virus (named ECHO25-GM-CSF), which has a genomic RNA sequence shown as SEQ ID NO: 15;

Modified form 4: the sequence (SEQ ID NO: 7) encoding the single chain antibody against human programmed death receptor 1 (Anti-PD-1 scFv) was inserted between the VP1 gene and 2A gene of the cDNA (SEQ ID NO: 1) of wild-type ECHO25 to obtain the cDNA (SEQ ID NO: 11) of the recombinant virus (named ECHO25-Anti-PD-1), which has a genomic RNA sequence shown as SEQ ID NO: 16.

Then, the cDNA sequences (SEQ ID NO: 1, 8-11) of the above five oncolytic viruses were sent to the gene synthesis company (Shanghai Biotech Engineering Co., Ltd.) for full gene synthesis, and ligated into the pSVA plasmids (Hou et al. Virus Res 2015, 205: 41-44) to obtain the infectious cloning plasmids of ECHO25 or modified forms thereof (i.e., ECHO25-WT, ECHO25-HRV2, ECHO25-miR133&206T, ECHO25-GM-CSF and ECHO25-Anti-PD-1).

(2) Plasmid mini-kit and *E. coli*. DH5a competent cells were purchased from Beijing Tiangen Biochemical Technology Co., Ltd.; 293T cells (ATCC® Number: CRL-3216™) and human rhabdomyosarcoma cells (RD cells; ATCC® Number: CCL-136™) were kept by National Institute of Diagnostics and Vaccine Development in Infectious Diseases, Xiamen University, China, and were cultured with DMEM and MEM media respectively, in which 10% fetal bovine serum as well as glutamine, penicillin and streptomycin were added; transfection reagents Lipofactamine2000 and Opti-MEM were purchased from Thermo Fisher Scientific Company.

(3) The infectious cloning plasmids containing the cDNA sequences of the above five oncolytic viruses were transformed into *E. coli* DH5a competent cells, the monoclonal strains were picked out and shaken after the outgrowth of clones, and the plasmids were extracted using the plasmid mini-kit, and then sent to the company (Shanghai Biotech Engineering Co., Ltd.) for sequencing analysis.

(4) The infectious cloning plasmids with correct sequence and the helper plasmid pAR3126 were co-transfected into the cells to rescue virus (Hou et al. Virus Res 2015, 205: 41-44). 293T cells were first transfected according to the instructions of the transfection reagent; then observed under a microscope. When CPE appeared in 293T cells, the cells and culture supernatant were harvested, and inoculated with RD cells followed by passaging and culturing, thereby obtaining the candidate strain of oncolytic virus.

Example 2: In Vitro Antitumor Experiment of ECHO25 and Modified Forms Thereof

2.1 Viruses and Cell Lines as Used (1) Viruses: this example used ECHO25-WT (SEQ ID NO: 12), ECHO25-HRV2 (SEQ ID NO: 13), ECHO25-miR133&206T (SEQ ID NO: 14), ECHO25-GM-CSF (SEQ ID NO: 15) and ECHO25-Anti-PD-1 (SEQ ID NO: 16) as provided in Example 1.

(2) Cell lines: human rhabdomyosarcoma cell RD (ATCC® Number: CCL-136™); human colorectal cancer cell lines SW480 (ATCC® Number: CCL-228™) and HT-29 (ATCC® Number: HTB-38™); humans gastric cancer cell lines AGS (ATCC® Number: CRL-1739™), SGC7901 (CCTCC deposit number: GDC150), BGC823 (CCTCC deposit number: GDC151), and NCI-N87 (ATCC® Number: CRL-5822™); human small cell lung cancer cell line NCI-H1417 (ATCC® Number: CRL-5869™); human non-small cell lung cancer cell lines SPC-A-1 (CCTCC Deposit Number: GDC050), NCT-H1299 (ATCC® Number: CRL-5803™), NCI-H1975 (ATCC® Number: CRL-5908™), A549 (ATCC® Number: CCL-185™), NCI-H661 (ATCC Number: HTB-183™), EBC-1 (Thermo Fisher Scientific, Catalog #: 11875101) and NCI-H1703 (ATCC® Number: CRL-5889™); human liver cancer cell lines C3A (ATCC® Number: CRL-10741™), Hep3B (ATCC® Number: HB-8064™), Huh7 (CCTCC Deposit Number: GDC134) and PLC/PRF/5 (ATCC® Number: CRL-8024™); human ovarian cancer cell lines ES-2 (ATCC® Number: CRL-1978™) and Caov3 (ATCC® Number: HTB-75™); human endometrial cancer cell lines Hec-1-A (ATCC Number: HTB-112™), Hec-1-B (ATCC® Number: HTB-113™) and Ishikawa (ECACC No. 99040201); human cervical cancer cell lines Hela (ATCC® Number: CCL-2™), Caski (ATCC® Number: CRL-1550™), and C-33A (ATCC® Number: HTB-31™); human melanoma cell lines A-375 (ATCC® Number: CRL-1619™) and SK-MEL-1 (ATCC® Number: HTB-67™); human breast cancer cell lines BT-474 (ATCC® Number: HTB-20™), MDA-MB-231 (ATCC® Number: HTB-26™), MDA-MB-453 (ATCC® Number: HTB-131™), MCF-7 (ATCC® Number: HTB-22™), ZR-75-30 (ATCC® Number: CRL-1504™), SK-BR-3 (ATCC® Number: HTB-30™) and BcaP37 (CCTCC deposit number: GDC206); human kidney cancer cell lines A-498 (ATCC® Number: HTB-44™), 786-O (ATCC® Number: CRL-1932™) and Caki-1 (ATCC® Number: HTB-46™); human pancreatic cancer cell line HPAF-2 (ATCC® Number: CRL-1997™); human prostate cancer cells lines PC-3 (ATCC® Number: CRL-1435™) and DU145 (ATCC® Number: HTB-81™); human glioma cell lines GBM (primary tumor cell line isolated from patient tumor tissue) and U118-MG (ATCC® Number: HTB-15™); human pharyngeal squamous carcinoma cell line FaDu (ATCC® Number: HTB-43™); human tongue squamous cell carcinoma cell line CAL 27 (ATCC® Number: CRL-2095™); human nasopharyngeal carcinoma cell line CNE (purchased from the Cell Center of Basic Medicine, Institute of Basic Medical Sciences, Chinese Academy of Medical Sciences, No. 3131C0001000700013); human nasal septum squamous carcinoma cell line RPMI 2650 (ATCC® Number: CCL-30™); human laryngeal carcinoma cell line HEp-2 (ATCC® Number: CCL-23™); metastatic cells from pleural effusion of human pharyngeal carcinoma Detroit 562 (ATCC® Number: CCL-138™); human submandibular adenocarcinoma cell line A-235 (preserved by National Institute of Diagnostics and Vaccine Development in Infectious Diseases); human thyroid cancer cell lines SW579 (preserved by National Institute of Diagnostics and Vaccine Development in Infectious Diseases) and TT (ATCC® Number: CRL-1803™); human esophageal cancer cell line TE-1 (purchased from the Cell Resource Center, Shanghai Institutes for Biological Sciences, Chinese Academy of Sciences, No. 3131C0001000700089); human bladder cancer cell lines J82 (ATCC® Number: HTB-1™) and 5637 (ATCC® Number: HTB-9™); human leukemia cell lines Jurkat (ATCC® Number: T1B-152™), THP-1 (ATCC® Number: TIB-202™), CCRF-CEM (ATCC® Number: CCL-119™), MOLT-4 (ATCC® Number: CRL-1582™), K562 (ATCC® Number: CCL-243™); human lymphoma cell lines Daudi (ATCC® Number: CCL-213™), Raji (ATCC® Number: CCL-86™) and U937 (ATCC® Number: CRL-1593.2™); human normal cell lines including: human foreskin fibroblast cell line HFF-1 (ATCC® Number: SCRC-1041™), human skin keratinocyte cell line HaCat (CCTCC deposit number: GDC106), human prostate stromal cell line WPMY-1 (ATCC® Number: CRL-2854™) and human umbilical vein endothelial cell line HUVEC (Thermo Fisher Scientific, Catalog #: C01510C). The above cells were all preserved by National Institute of Diagnostics and Vaccine Development in Infectious Diseases, China, Xiamen University. AGS and TT were cultured with F-12K medium; RD, C-33A, SK-MEL-1, J82, FaDu, EBC-1, RPMI2650, Detroit 562 and DU145 were cultured with MEM medium; NCI-H1417, NCI-H1703, Caski, BT-474, ZR-75-30, SK-BR-3, 786-0, Jurkat, THP-1, CCRF-CEM, MOLT-4, Daudi, Raji, K562, U937, 5637, TE-1, Caski, NCI-H1975, NCI-H661, SGC7901 and BGC823 were cultured with RPMI-1640 medium; ES-2, A-235 were cultured with McCoy's 5A medium; MDA-MB-231 and MDA-MB-453 were cultured with Leibovitz's L-15 medium; other cells were cultured with DMEM medium. All of these mediums were supplemented with 10% fetal bovine serum, glutamine and penicillin-streptomycin. All the above cells were cultured under the standard conditions of 37° C. and 5% $CO_2$.

2.2 Culture of Viruses

RD cells were evenly plated on 10 cm cell culture plates, and the culture conditions included MEM medium containing 10% fetal bovine serum and glutamine, penicillin and streptomycin, 37° C., 5% $CO_2$, and saturated humidity. When the cell confluence reached 90% or more, the cell culture medium was replaced with serum-free MEM medium, and each plate was inoculated with $10^7$ TCID50 of ECHO25-WT, ECHO25-HRV2, ECHO25-miR133&206T, ECHO25-GM-CSF or ECHO25-Anti-PD-1. After continuous culture for 24 hours, the ECHO25 or its modified form proliferated in RD cells and caused CPE in cells. When more than 90% of the cells turned contracted and rounded, showed increased graininess, and became detached and lysed, the cells and culture supernatant thereof were harvested. After freeze-thawing for three cycles, the culture supernatant was collected and centrifuged to remove cell debris, wherein the centrifuge conditions were 4000 rpm, 10 min, 4° C. Finally, the supernatant was filtered with a 0.22 μm disposable filter (Millipore Company) to remove impurities such as cell debris.

2.3 Determination of Virus Titer

The RD cells were plated in a 96-well plate with a cell density of $10^4$ cells/well. After the cells adhered, the virus solution obtained in Example 2.2 was diluted 10-fold with serum-free MEM medium from the first 10-fold dilution. 50 μl of the dilution of virus was added to the wells with cells. After 7 days, the wells where CPE appeared were monitored and recorded, followed by calculation using Karber method, in which the calculation formula was $1g^{TCID50}$=L−D (S−0.5), L: logarithm of the highest dilution, D: difference between the logarithms of dilutions, S: sum of proportions of positive wells. The unit of TCID50 thus calculated was TCID50/50 μl, which should be converted to TCID50/ml.

2.4 In Vitro Antitumor Experiments of Viruses

Human tumor cells and normal cells were inoculated into 96-well plates at $10^4$ cells/well. After the cells adhered, the medium in each well was replaced with the corresponding cell culture medium without serum, and viruses were inoculated at an MOI of 0.1, 1, 10 or 100. Subsequently, CPE of the cells were monitored daily by a microscope.

FIG. 1 shows micrographs of the human umbilical vein endothelial cell line HUVEC, the human esophageal cancer cell line TE-1, the human endometrial cancer cell lines HEC-1-A and HEC-1-B, which were not infected with viruses (negative control groups, Mock) or treated with ECHO25-WT at MOI=1 for 72 hours. The results showed that after 72 hours of infection at a multiplicity of infection (MOI) of 1, a significant reduction in the number of the tumor cells, marked shrinking and lysis and the like, were detected in the virus-infected groups; while as compared to the non-tumor cells in the Mock groups, the non-tumor cells infected with the viruses showed almost no change in cell morphology. The above results demonstrated that ECHO25 had significant oncolytic effects on human esophageal cancer cell line TE-1, the human endometrial cancer cell lines HEC-1-A and HEC-1-B, but did not have any effect on non-tumor cells HUVEC.

After 72 hours of virus infection and culture, the cell survival rate was detected using Cell Counting Kit-8 (CCK-8 kit; Shanghai Biyuntian Biotechnology Co., Ltd.) and crystal violet staining method (only for adherent cells), and the specific method was as follows:

(1) Cell Survival Rate Detected by CCK8 Method

For adherent cells, the original medium in a 96-well cell culture plate was directly discarded; for suspension cells, the original medium in a 96-well cell culture plate was carefully discarded after centrifugation; and then 100 p of fresh serum-free medium was added per well. 10 μl of CCK-8 solution was added to each of the wells inoculated with cells, and an equal amount of CCK-8 solution was also added to the blank culture medium as a negative control, followed by incubation at 37° C. in a cell culture incubator for 0.5-3 hours. The absorbance was detected at 450 nm using a microplate reader at 0.5, 1, 2, 3 hours, respectively, and the time point where the absorbance was within a suitable range was selected as a reference for cell survival rate. The CCK-8 test results of ECHO25-WT for each kind of cells were shown in Table 2, where "−" indicated that the cell survival rate after virus treatment was not significantly different from that of the MOCK group; "+" indicated that after virus treatment, the cell number was reduced, the survival rate was still greater than 50% but was significantly different from that of the MOCK group; "++" indicated that the cell survival rate after virus treatment was less than 50%, and was significantly different from that of the MOCK group.

The calculation of cell survival rate was:

$$\text{Cell\_survival\_rate (\%)} = \frac{(\text{reading\_of\_test\_group} - \text{reading\_of\_negative\_group})}{(\text{reading\_of\_positive\_group} - \text{reading\_of\_negative\_group})} \times 100\%.$$

(2) Cell Survival Rate Detected by Crystal Violet Staining Method (Only for Adherent Cells)

Figure 2:
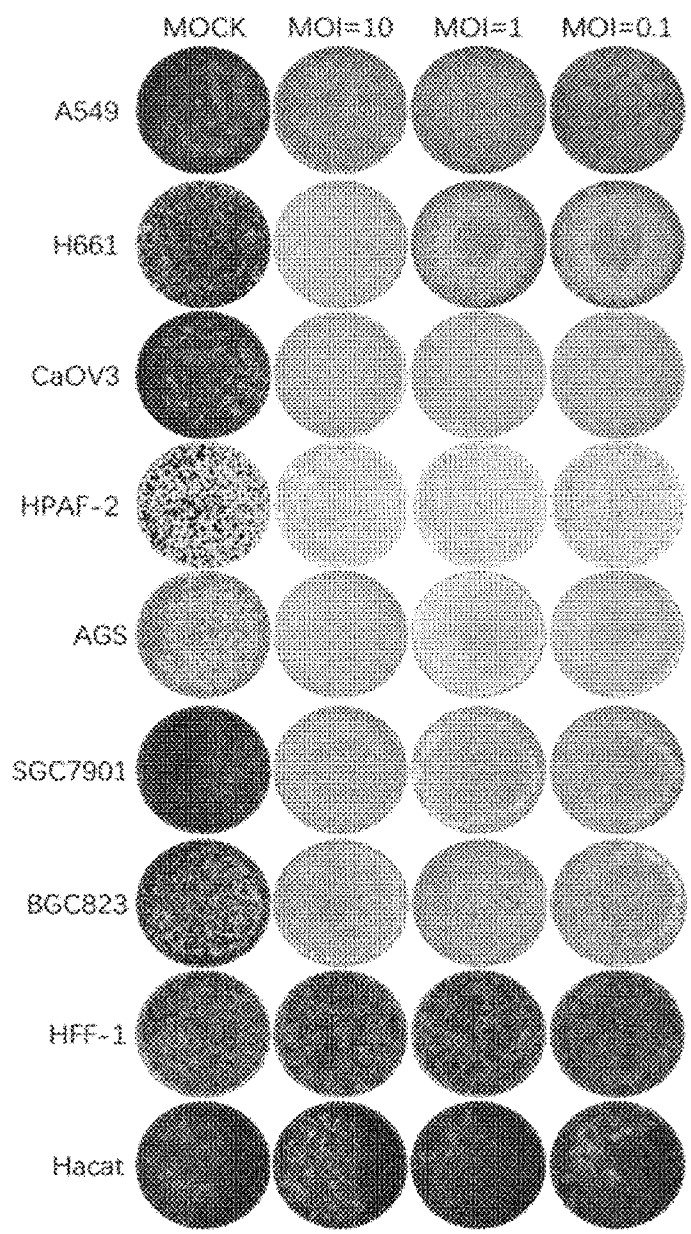
FIG. 2 shows the photos of crystal violet staining of the in vitro killing tests of the wild-type ECHO25 on human non-small cell lung cancer cell lines A549 and NCI-H661, human ovarian cancer cell line Caov3, human pancreatic cancer cell line HPAF-2, human gastric cancer cell lines AGS, SGC7901 and BGC823, human foreskin fibroblast cell line HFF-1 and human skin keratinocyte cell line HaCat in Example 2, wherein MOCK represents cells that are not infected with the virus. The results showed that the ECHO25 had significant oncolytic effects on A549, NCI-H661, Caov3, HPAF-2, AGS, SGC7901 and BGC823, after 72 hours of infection at MOIs of 10, 1, and 0.1, but had no effect on HFF-1 and HaCat of human non-tumor cells.

After the cells were infected with viruses for 3 days, the culture supernatant in the 96-well cell culture plate was discarded, 100 s of methanol was added to each well, followed by fixation in the dark for 15 min. Crystal violet powder (Shanghai Biotech Biotechnology Co., Ltd.) was weighed, and formulated as 2% (w/v) crystal violet methanol solution, which was stored at 4° C. An appropriate amount of 2% crystal violet methanol solution was taken and formulated with PBS solution to prepare 0.2% crystal violet working solution. After fixation for 15 minutes, the methanol fixation solution in the 96-well cell culture plate was discarded, and 100 μl of the crystal violet working solution was added to the plate and staining was performed for 30 min. After the crystal violet staining solution was discarded, PBS solution was used for washing for 3 to 5 times, until the excess staining solution was washed off, and air-drying was performed. ImmunSpot @ S5 UV Analyzer (Cellular Technology Limited, USA) was used for photographing. FIG. 2 showed the crystal violet staining results of the human non-small cell lung cancer cell lines A549 and NCI-H661, human ovarian cancer cell line Caov3, human pancreatic cancer cell line HPAF-2, human gastric cancer cell lines AGS, SGC7901, and BGC823, human foreskin fibroblast cell line HFF-1 and human skin keratinocyte line HaCat of human normal cell lines in the control groups (MOCK) and in the experimental groups (infected for 72 hours with ECHO25-WT at MOIs of 0.1, 1, and 10, respectively). As shown in the results, after 72 hours of infection at MOIs of 10, 1, and 0.1, the tumor cells in the experimental groups were significantly reduced as compared to the control group (MOCK) without addition of virus; while the number of non-tumor cells showed no significant change. The above results indicated that the ECHO025-WT had significant oncolytic effects on human tumor cell lines A549. NCI-H661. Caov3. HPAF-2. AGS. SGC7901 and BGC823, but had no significant effect on non-tumor cell lines HFF-1 and HaCat.

TABLE 2

Results of in vitro antitumor experiments of wild-type enterovirus ECHO25

| Cell line | MOI | | | |
|---|---|---|---|---|
| | 0.1 | 1 | 10 | 100 |
| RD | ++ | ++ | ++ | ++ |
| SW480 | ++ | ++ | ++ | ++ |
| HT-29 | ++ | ++ | ++ | ++ |
| AGS | ++ | ++ | ++ | ++ |
| SGC7901 | ++ | ++ | ++ | ++ |
| BGC823 | ++ | ++ | ++ | ++ |
| NCI-N87 | + | + | ++ | ++ |
| SPC-A-1 | ++ | ++ | ++ | ++ |
| NCI-H1299 | ++ | ++ | ++ | ++ |
| NCI-H1975 | – | + | ++ | ++ |
| A549 | ++ | ++ | ++ | ++ |
| C3A | + | ++ | ++ | ++ |
| Hep3B | – | + | ++ | ++ |
| Huh7 | – | + | ++ | ++ |
| PLC/PRF/5 | – | – | ++ | ++ |
| Caov3 | ++ | ++ | ++ | ++ |
| Hcc-1-A | ++ | ++ | ++ | ++ |
| Hec-1-B | ++ | ++ | ++ | ++ |
| Ishikawa | ++ | ++ | ++ | ++ |
| C-33A | ++ | ++ | ++ | ++ |
| A-375 | – | – | + | ++ |
| SK-MEL-1 | + | + | ++ | ++ |
| BcaP37 | ++ | ++ | ++ | ++ |
| Caki-1 | ++ | ++ | ++ | ++ |
| HPAF-2 | ++ | ++ | ++ | ++ |
| PC-3 | ++ | ++ | ++ | ++ |
| DU145 | – | ++ | ++ | ++ |
| GBM | ++ | ++ | ++ | ++ |
| U118-MG | ++ | ++ | ++ | ++ |
| FaDu | – | – | + | + |
| CAL27 | – | – | + | + |
| CNE | – | – | + | + |
| Hep2 | – | – | + | + |
| TE-1 | – | ++ | ++ | ++ |
| J82 | – | + | + | ++ |
| 5637 | – | ++ | ++ | ++ |
| K562 | + | + | ++ | ++ |
| U937 | – | + | ++ | ++ |
| EBC-1 | – | – | – | – |
| NCI-H1417 | – | – | + | + |
| NCI-H1703 | – | – | – | – |
| ES-2 | – | – | – | – |
| HeLa | – | – | – | – |
| CaSki | – | – | – | – |
| MCF-7 | – | – | – | – |
| BT-474 | – | – | – | – |
| MDA-MB-231 | – | – | – | – |
| MDA-MB-453 | – | – | – | – |
| ZR-75-30 | – | – | – | – |
| SK-BR-3 | – | – | – | – |
| A498 | – | – | – | – |
| 786-O | – | – | – | – |
| Jurkat | – | – | – | – |
| Daudi | – | – | – | – |
| Raji | – | – | – | – |
| THP-1 | – | – | – | – |
| MOLT-4 | – | – | – | – |
| CCRF-CEM | – | – | – | – |
| RPMI2650 | – | – | – | – |
| Detroit 562 | – | – | – | – |
| A-235 | – | – | – | – |
| TT | – | – | – | – |
| HFF-1 | – | – | – | – |
| HaCat | – | – | – | – |
| WPMY-1 | – | – | – | – |
| HUVEC | – | – | – | + |

Note:
"–" indicated that there was no significant difference in cell survival rate between virus treatment group and MOCK group; "+" indicated that after virus treatment, the number of cells was reduced, the survival rate was greater than 50% but was significantly different from that of MOCK group; "++" indicated that the cell survival rate after virus treatment was less than 50%, and was significantly different from that of the MOCK group.

As could be seen from Table 2, ECHO25-WT had good killing effects on specific tumor cell types. In particular, the virus had significant killing effects on colorectal cancer cell lines, gastric cancer cell lines, non-small cell lung adenocarcinoma cell lines, ovarian cancer cell lines, clear cell renal carcinoma cell lines, endometrial cancer cell lines, HPV-negative cervical cancer cell lines, breast medullary carcinoma cell lines, prostate cancer cell lines, glioma cell lines, esophageal cancer cell lines, etc., and had good killing effects on liver cancer cell lines, pancreatic cancer cell lines, bladder cancer cell lines, histiocytic lymphoma cell lines, and chronic myeloid leukemia cell lines; while, ECHO25-WT showed no significant killing activity to non-small cell lung squamous carcinoma cell lines, small cell lung carcinoma cell lines, HPV-positive cervical cancer cell lines, breast non-medullary cancer cell lines, renal adenocarcinoma cell lines, B cell lymphoma cell lines, T cell leukemia cell lines, nasal septum squamous carcinoma cell lines, submandibular adenocarcinoma cell lines, thyroid cancer cell lines, etc. In addition, the virus had substantially no toxicity to non-tumor cell lines including human foreskin fibroblast cell line HFF-1, human skin keratinocyte cell line HaCat and human prostate stromal cell line WPMY-1, except that it showed certain toxicity to human umbilical vein endothelial cell line HUVEC at MOI=100.

In addition, the in vitro antitumor experiments of ECHO25-HRV2, ECHO25-miR133&206T, ECHO25-GM-CSF and ECHO25-Anti-PD-1 showed that the four modified ECHO25 forms all retained the killing effects of the parent wild-type ECHO25 on specific tumor cells, and showed significant killing effects on colorectal cancer cell lines, gastric cancer cell lines, ovarian cancer cell lines, clear cell renal carcinoma cell lines, endometrial cancer cell lines, HPV-negative cervical cancer cell lines, breast medullary carcinoma cell lines, prostate cancer cell lines, glioma cell lines, esophageal cancer cell lines and so on. The CCK-8 detection results of oncolytic activity to human colorectal cancer cell line SW480, human gastric cancer cell line AGS, human endometrial cancer cell line Ishikawa and human glioma cell line U118-MG were shown in Table 3. In addition, the four modified ECHO25 forms showed no significant killing activity to non-small cell lung squamous carcinoma cell lines, small cell lung cancer cell lines, HPV-positive cervical cancer cell lines, breast non-medullary cancer cell lines, renal adenocarcinoma cell lines, B-cell lymphoma cell lines, T-cell leukemia cell lines, nasal septum squamous carcinoma cell lines, submandibular adenocarcinoma cell lines, etc. It was worth noting that ECHO25-HRV2 showed significant killing activity on some tumor cells to which ECHO25-WT showed almost no killing activity. The CCK-8 detection results of oncolytic activity to human pharyngeal squamous carcinoma cell line FaDu and human thyroid cancer cell line SW579 were shown in Table 4.

TABLE 3

In vitro antitumor experimental results of ECHO25-HRV2, ECHO25-miR133&206T, ECHO25-GM-CSF and ECHO25-Anti-PD-1

| Cell Line | | MOI | | | |
|---|---|---|---|---|---|
| | | 0.1 | 1 | 10 | 100 |
| ECHO25-HRV2 | SW480 | ++ | ++ | ++ | ++ |
| | AGS | ++ | ++ | ++ | ++ |
| | Ishikawa | ++ | ++ | ++ | ++ |
| | U118-MG | ++ | ++ | ++ | ++ |

TABLE 3-continued

In vitro antitumor experimental results of ECHO25-HRV2, ECHO25-miR133&206T, ECHO25-GM-CSF and ECHO25-Anti-PD-1

| Cell Line | | MOI 0.1 | 1 | 10 | 100 |
|---|---|---|---|---|---|
| ECHO25-miR133&206T | SW480 | ++ | ++ | ++ | ++ |
| | AGS | ++ | ++ | ++ | ++ |
| | Ishikawa | ++ | ++ | ++ | ++ |
| | U118-MG | ++ | ++ | ++ | ++ |
| ECHO25-GM-CSF | SW480 | ++ | ++ | ++ | ++ |
| | AGS | ++ | ++ | ++ | ++ |
| | Ishikawa | ++ | ++ | ++ | ++ |
| | U118-MG | ++ | ++ | ++ | ++ |
| ECHO25-Anti-PD-1 | SW480 | ++ | ++ | ++ | ++ |
| | AGS | ++ | ++ | ++ | ++ |
| | Ishikawa | ++ | ++ | ++ | ++ |
| | U118-MG | ++ | ++ | ++ | ++ |

Note:
"−" indicated that there was no significant difference in cell survival rate between virus treatment group and MOCK group; "+" indicated that after virus treatment, the number of cells was reduced, the survival rate was greater than 50% but was significantly different from that of MOCK group; "++" indicated that the cell survival rate after virus treatment was less than 50%, and was significantly different from that of the MOCK group.

TABLE 4

Comparison of in vitro oncolytic experimental results of ECHO25-WT and ECHO25-HRV2 on human pharyngeal squamous carcinoma cell line FaDu and human thyroid cancer cell line SW579

| Cell Line | | MOI 0.1 | 1 | 10 | 100 |
|---|---|---|---|---|---|
| ECHO25-WT | FaDu | − | − | + | + |
| | SW579 | − | − | − | − |
| ECHO25-HRV2 | FaDu | ++ | ++ | ++ | ++ |
| | SW579 | + | ++ | ++ | ++ |

Note:
"−" indicated that there was no significant difference in cell survival rate between virus treatment group and MOCK group; "+" indicated that after virus treatment, the number of cells was reduced, the survival rate was greater than 50% but was significantly different from that of MOCK group; "++" indicated that the cell survival rate after virus treatment was less than 50%, and was significantly different from that of the MOCK group.

2.5 Serial Passaging of ECHO25 for Adaptation

In this example, ECHO25 was serially passaged for adaptation in a certain type of tumor cells to obtain a virus strain with enhanced killing activity to the tumor cell.

The wild-type ECHO25 was serially passaged for adaptation in human liver cancer cell line PLC/PRF/5, human melanoma cell line A-375 or human bladder cancer cell line J82, on which oncolytic effects of wild-type ECHO25 were not very significant, and the specific method was as follows:

One kind of the above tumor cells was evenly plated on a 10 cm cell culture plate, and the culture conditions included a corresponding cell culture media containing 10% fetal bovine serum and glutamine, penicillin and streptomycin, 37° C., 5% $CO_2$, and saturated humidity. When the cell confluence reached 90% or more, the cell culture medium was replaced with serum-free cell culture medium, each plate was inoculated with $10^7$ TCID50 of ECHO25, the culture environment was changed to 33° C., 5% $CO_2$ saturated humidity. When ECHO25 proliferated in tumor cells and caused CPE in the cells (after infection for up to 3 days), the cells and their culture supernatant were harvested. After freeze-thawing for three cycles, centrifugation was performed at 4° C., 4000 rpm for 10 min. The centrifugation supernatant was taken and added onto new tumor cells with a cell confluence of more than 90% to complete one round of virus passage. The passage was repeated for more than 10 times, and a part of the virus solution was taken for virus titer detection in RD cells in each round of passage, and the specific method referred to Example 2.3. Generally, the virus replication ability would increase with the generation, and when a relatively high infectious titer was reached and the virus replication was stable in the tumor cell, the adapted strain of ECHO25 for the tumor cell was obtained.

Subsequently, by the in vitro antitumor experimental method described in Example 2.4, the human tumor cell PLC/PRF/5, A-375 or J82 was inoculated to a 96-well plate at $10^4$ cells/well. After the cells adhered, the medium in each well was replaced with the corresponding culture medium free of serum, followed by incubation at 37° C. for 30 min, and then the serially passaged ECHO25 virus strains (viral titers of which were detected on RD cells) adapted for each of the above kinds of cells at MOIs of 0.1, 1, 10, and 100 were inoculated. Subsequently, CPE of the cells were monitored daily by a microscope, and the cell survival rate was detected using CCK-8 method 72 hours after the infection and culture of viruses.

The results were shown in Table 5, in which after serial passaging of the wild-type enterovirus ECHO25 in a certain kind of tumor cells on which ECHO25 had poor oncolytic effect, the killing activity thereof on the tumor cells was significantly enhanced, indicating that the serial passaging method could be used to obtain an ECHO25 adapted strain with enhanced oncolytic effect on the tumor cells.

TABLE 5

In vitro killing experimental results of ECHO25 on tumor cells after serial passaging for adaptation in tumor cells

| Cell Line | MOI 0.1 | 1 | 10 | 100 |
|---|---|---|---|---|
| PLC/PRF/5 | + | ++ | ++ | ++ |
| A-375 | − | + | ++ | ++ |
| J82 | + | ++ | ++ | ++ |

Note:
"−" indicated that there was no significant difference in cell survival rate between virus treatment group and MOCK group; "+" indicated that after virus treatment, the number of cells was reduced, the survival rate was greater than 50% but was significantly different from that of MOCK group; "++" indicated that the cell survival rate after virus treatment was less than 50%, and was significantly different from that of the MOCK group.

2.6 Evaluation of Oncolytic Effect of Genomic RNA of ECHO25

In this example, a large amount of infectious live viruses of ECHO25 could be produced by transfecting the purified genomic RNA of ECHO25 into a certain kind of tumor cells, and thus kill the tumor cells.

Figure 3:
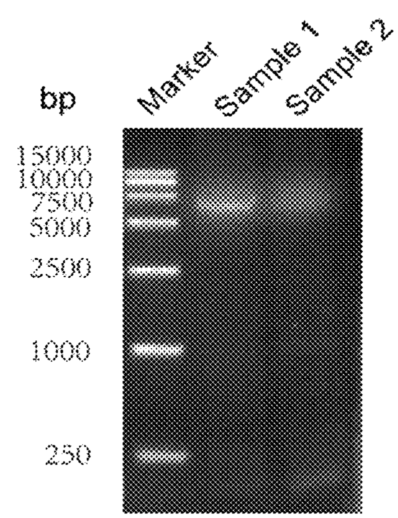
FIG. 3 shows an electrophoresis image of two samples of wild-type ECHO25 virus genomic RNA of the same batch obtained by the in vitro transcription method in Example 2.

The viral genomic RNA was first obtained by in vitro transcription, and this method could be found in, for example, Hadac E M, Kelly E J and Russell S J. Mol Ther, 2011, 19(6): 1041-1047. Specifically, the infectious cloning plasmid of wild-type ECHO25 obtained in Example 1 was linearized, and the linearized plasmid was used as a template for in vitro transcription using MEGAscript™ T7 Transcription Kit (Thermo Fisher Scientific, AM1333) so as to produce a large amount of viral RNA. And the obtained viral RNA was purified using MEGAclear™ Transcription Clean-Up Kit (Thermo Fisher Scientific, AM1908) for next use. The RNA electropherograms of two parallel samples were shown in FIG. 3.

Subsequently, according to the method of the in vitro antitumor experiment described in Example 2.4, the human colorectal cancer tumor cell line SW480 was inoculated to a 24-well plate at $10^5$ cells/well. After the cells adhered, the medium in each well was replaced with a corresponding cell culture medium free of serum, followed by incubation at 37°

C. for 30 min. Then, SW480 cells were transfected with purified virus RNA at 1 μg per well using transfection reagent Lipofectamine® 2000 (Thermo Fisher Scientific, 11668019), and the negative control group was transfected with irrelevant RNA nucleic acid molecules. Subsequently, CPE of the cells were monitored daily by a microscope.

Figure 4:
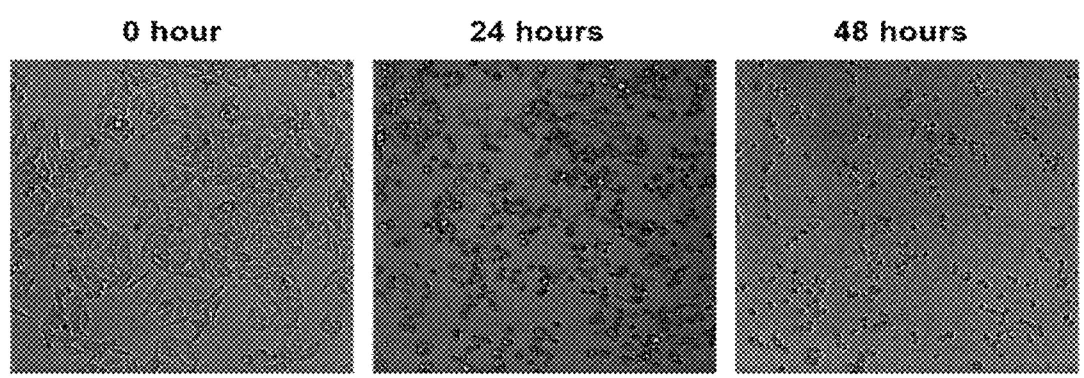
FIG. 4 shows the killing effect of the wild-type ECHO25 virus genomic RNA on human colorectal cancer cell line SW480 in Example 2. The results showed that SW480 cells showed obvious CPE after 24 hours of transfection with ECHO25 genomic RNA, and were almost all lysed to death by 48 hours.
Figure 5A:
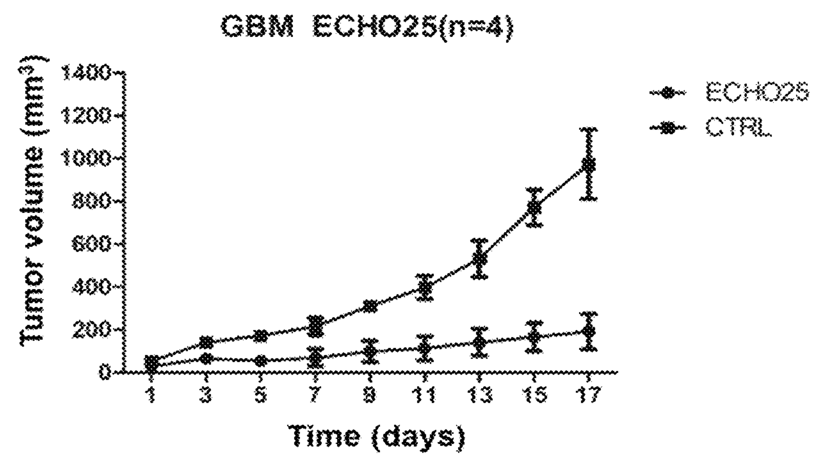
FIGS. 5A to 5D show the results of in vivo antitumor experiment of the wild-type ECHO25 on human glioma cell line GBM (A), human endometrial cancer cell line Ishikawa (B), human prostate cancer cell line PC-3 (C) and human breast cancer cell line BcaP37 (D) in Example 3. The results showed that, in the challenge experimental groups, $10^6$ TCID50 per tumor mass of ECHO25 were injected intratumorally every third day. After 5 treatments in total, the growth of the tumors formed by subcutaneous inoculation of GBM, Ishikawa, PC-3 or BcaP37 cells in SCID mice significantly slowed down and arrested, and the tumors were even lysed and disappeared. In contrast, the tumors of the negative group (CTRL) without treatment of oncolytic virus maintained the normal growth, and their tumor volumes were significantly larger than those in the challenge groups.
Figure 5B:
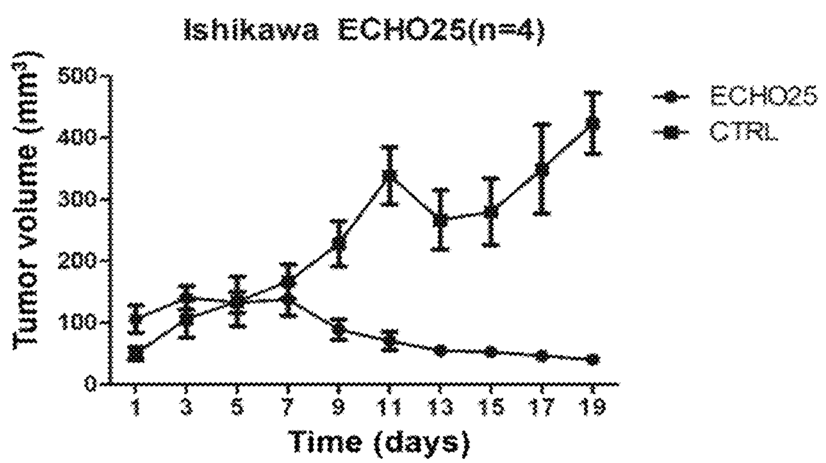
Figure 5C:
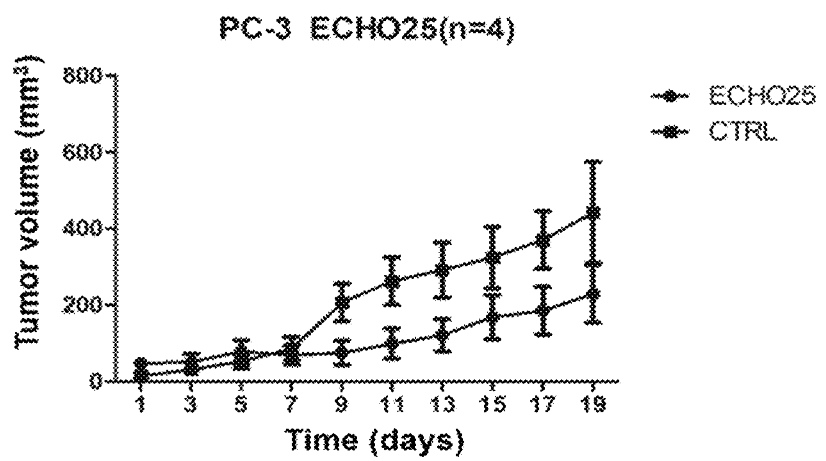
Figure 5D:
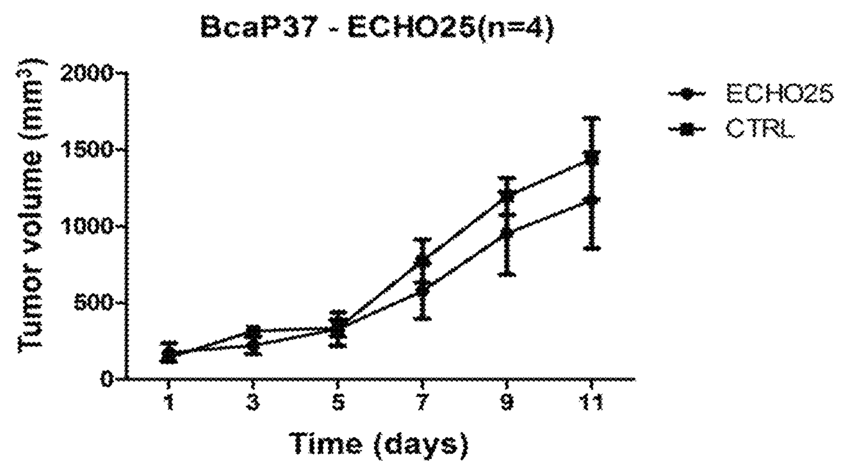

The results showed that CPE began to appear in the SW480 cells transfected with genomic RNA of ECHO25 about 8 hours after transfection, and then the cytopathy gradually increased. After 48 hours, the survival rate was measured using the CCK8 method, the SW480 cells had almost all died and lysed, and the micrographs of SW480 cells at 0, 24 and 48 hours after infection were shown in FIG. 4. The culture supernatant was inoculated into new SW480 cells and CPE was quickly produced. The results indicated that the direct administration with the nucleic acid of ECHO25 also had good killing activity and could be used to treat tumors.

Example 3: In Vivo Antitumor Experiments of ECHO25 and Modified Forms Thereof 3.1 Viruses. Cell Lines and Experimental Animals (1) Viruses: ECHO25-WT (SEQ ID NO: 12), ECHO25-HRV2 (SEQ ID NO: 13), ECHO25-miR133&206T (SEQ ID NO: 14), ECHO25-GM-CSF (SEQ ID NO: 15) and ECHO25-Anti-PD-1 (SEQ ID NO: 16) as provided in Example 1 were used in this example. The methods of virus culture and virus titer measurement could be seen in Examples 2.2 and 2.3, respectively.

(2) Cell lines: human glioma cell line GBM (primary tumor cell line isolated from patient tumor tissue), human endometrial cancer cell line Ishikawa (ECACC No. 99040201), human prostate cancer cell line PC-3 (ATCC® Number: CRL-1435™) and human breast cancer cell line BcaP37 (CCTCC deposit number: GDC206). The above cells were all cultured in DMEM medium, and the medium was added with 10% fetal bovine serum, glutamine and penicillin-streptomycin. All the above cells were cultured under the standard conditions of 37° C. and 5% $CO_2$.

(3) Experimental animals: female C.B17 SCID mice aged 6-8 weeks were from Shanghai Slark Experimental Animal Co., Ltd.; according to the protocol approved by the Experimental Animal Center and Ethics Committee of Xiamen University, the mice were raised under SPF conditions.

3.2 In Vivo Antitumor Experiments of the Viruses

The tumor cells used for subcutaneous tumor formation in SCID mice were digested with 0.01% trypsin, and then resuspended into a single-cell suspension using a cell culture medium containing 10% fetal bovine serum. The cell density of the suspension was counted. The cells were precipitated by centrifugation under 1000 g for 3 min, and then the cells were resuspended with an appropriate volume of PBS to reach a concentration of about $10^6$-$10^7$ cells/100 μl PBS. The tumor cells were subcutaneously inoculated in the back of SCID mice at $10^6$-$10^7$ cells/100 μl PBS/site with a syringe. When the tumor cells grew into a tumor mass of about 100 $mm^3$ under the skin of SCID mice after about 14-21 days, the tumor-bearing SCID mice were randomly divided into experimental groups (administrated with ECHO25-WT, ECHO25-HRV2, ECHO25-miR133&206T, ECHO25-GM-CSF or ECHO25-Anti-PD-1) and negative control group, with 4 mice (n=4) in each group. Oncolytic virus (ECHO25-WT, ECHO25-HRV2, ECHO25-miR133&206T, ECHO25-GM-CSF or ECHO25-Anti-PD-1) at $10^6$ TCID50/100 μl serum-free medium/tumor mass or equivalent amount of serum-free medium were intratumorally injected every two days, for a total of 5 treatments. The tumor size was measured with a vernier caliper and recorded every two days, and the method for calculating the tumor size was:

$$\text{Tumor size (mm}^3\text{)} = \text{tumor length value} \times (\text{tumor width value})^2/2.$$

The treatment results of ECHO25-WT for the above four tumors were shown in FIGS. 5A-5D. The results showed that after the challenge of ECHO25-WT, the growth of the four detected tumors of GBM (A), Ishikawa (B), PC-3 (C) and BcaP37 (D) gradually slowed down and arrested, and the tumors were even lysed and disappeared; by contrast, the tumors of the negative group (CTRL) maintained the normal growth, and their tumor sizes were significantly larger than those of the experimental groups.

Figure 6:
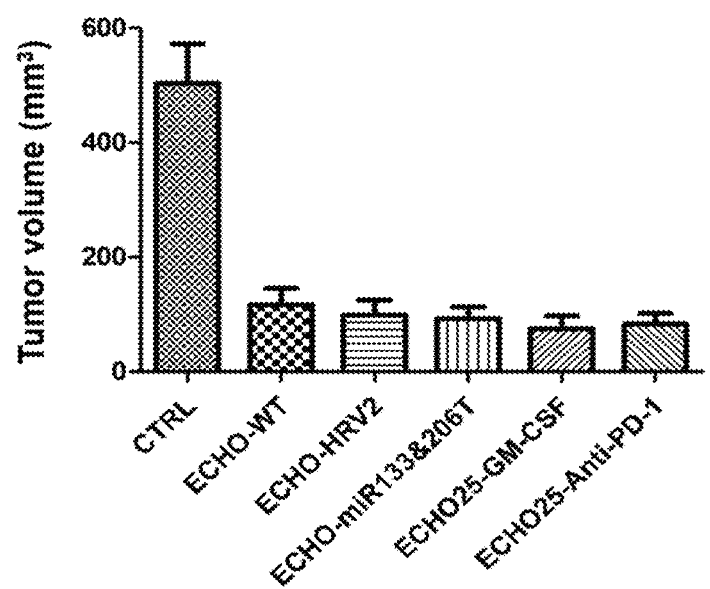
FIG. 6 shows the results of in vivo antitumor experiment of ECHO25-WT, ECHO25-HRV2, ECHO25-miR133&206T, ECHO25-GM-CSF and ECHO25-Anti-PD-1 on human glioma cell line GBM in Example 3. The results showed that, in the challenge experimental groups, $10^6$ TCID50 per tumor mass of ECHO25 were injected intratumorally every third day. After 5 treatments in total for 10 days, the growth of the tumors formed by subcutaneous inoculation of GBM cells in SCID mice arrested, and the tumors were even lysed and disappeared. In contrast, the tumors of the negative group (CTRL) without treatment of oncolytic virus maintained the normal growth, and their tumor volumes were significantly larger than those in the challenge groups.

FIG. 6 showed the results obtained after a treatment of the GBM tumor model with ECHO25-WT, ECHO25-HRV2, ECHO25-miR133&206T, ECHO25-GM-CSF or ECHO25-Anti-PD-1 for 10 days. The results showed that the tumor volumes were significantly reduced after treatment with ECHO25-WT, ECHO25-HRV2, ECHO25-miR133&206T, ECHO25-GM-CSF, and ECHO25-Anti-PD as compared with the negative control group that was not treated with oncolytic virus, and similar reductions in tumor volume were detected after treatment with 5 oncolytic viruses ECHO25-WT, ECHO25-HRV2, ECHO25-miR133&206T, ECHO25-GM-CSF and ECHO25-Anti-PD-1. The above results indicated that all of ECHO25-WT, ECHO25-HRV2, ECHO25-miR133&206T, ECHO25-GM-CSF and ECHO25-Anti-PD-1 showed remarkable and favorable anti-tumor activity in vivo.

Example 4: Safety Evaluation of Oncolytic Virus 4.1 Viruses and Laboratory Animals Used (1) Virus: ECHO25-WT (SEQ ID NO: 12) provided in Example 1 was used in this example. The methods for virus culture and virus titer measurement could refer to Examples 2.2 and 2.3, respectively.

(2) Experimental animals: BALB/c pregnant mice were from Shanghai Slark Experimental Animal Co., Ltd.; according to the protocol approved by the Experimental Animal Center and Ethics Committee of Xiamen University, the mice were raised under clean conditions, and then 1-day-old mice produced by the BALB/c pregnant mice were used for in vivo virulence evaluation of ECHO25.

4.2 Evaluation of In Vivo Safety of the Virus in Mice 1-day-old BALB/c suckling mice were selected for challenge with ECHO25-WT by intraperitoneal injection, and the titer doses for challenge were $10^4$, $10^5$, $10^6$, or $10^7$ TCID50/mouse. Then, the survival rates and health scores for the BALB/c mice challenged with different doses were recorded daily, wherein the evaluation criteria of the health score were: score of 5 represents dying or died; score of 4 represents severe limb paralysis; score of 3 represents weakness or mild deformity of limb; score of 2 represents wasting; score of 1 represents lethargy, piloerection, and trembling; and score of 0 represents healthy.

Figure 7:
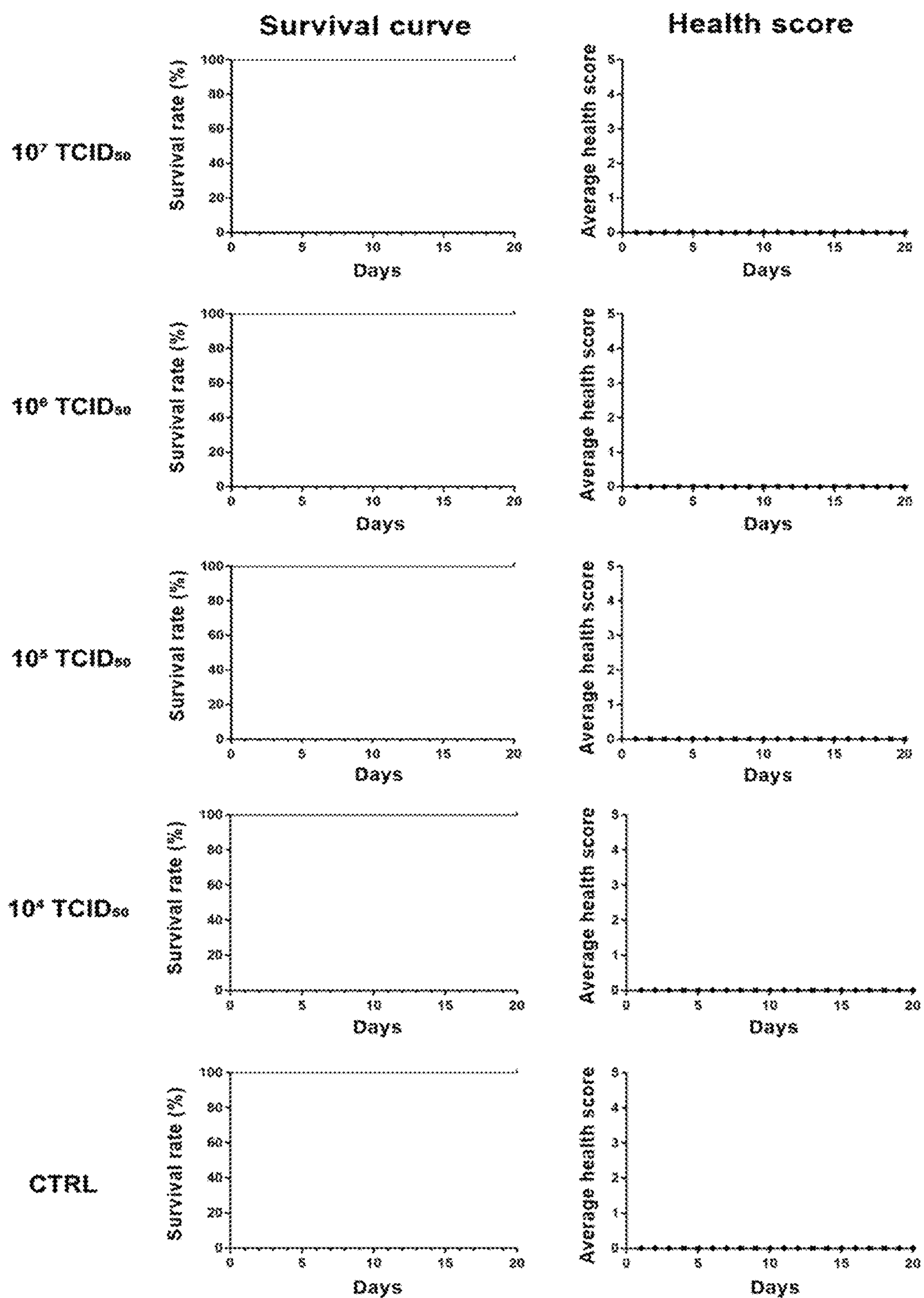
FIG. 7 shows the results of toxicity detection of ECHO25-WT in BALB/c mice in Example 4. 1-Day-old BALB/c mice were subjected to intraperitoneal injection of ECHO25 at different doses ($10^4$, $10^5$, $10^6$, and $10^7$ TCID50/mouse), and then survival rates and health scores of the mice after challenge were obtained. The results showed that ECHO25 had very limited toxicity to BALB/c mice and did not cause disease or death at high doses, indicating that ECHO25 had good safety in vivo.

The results were shown in FIG. 7. Within 14 days after challenge, no disease or death occurred in all mice in the challenge groups, indicating that ECHO25-WT had limited toxicity to BALB/c mice, and had no effect on the status of mice even at very high doses for challenge. The above results indicate that ECHO25-WT had good safety in vivo.

Although specific embodiments of the present invention have been described in detail, those skilled in the art will understand that according to all the teachings that have been published, various modifications and changes can be made to the detail, and these changes are all within the protection scope of the present invention. The protection scope of the present invention is given by the appended claims and any equivalents thereof.

The invention claimed is:

1. A method of treating a tumor, the method comprising administering, to a subject in need thereof, an effective amount of a modified Echovirus 25 (ECHO25) or a medicament comprising the modified ECHO25, wherein as compared to a genome of a wild-type ECHO25, a genome of the modified ECHO25 has an insertion of one or more exogenous nucleic acids, and wherein the one or more exogenous nucleic acids are selected from the group consisting of a nucleic acid sequence encoding a cytokine, a nucleic acid sequence encoding an antitumor protein or polypeptide, and a target sequence of microRNA.

2. The method of claim 1, wherein as compared to the genome of the wild-type ECHO25, the genome of the modified ECHO25 has a substitution of an internal ribosome entry site (IRES) sequence in a 5' untranslated region (5'UTR) with an exogenous IRES sequence.

3. The method of claim 2, wherein the exogenous IRES sequence is an internal ribosome entry site sequence of human rhinovirus 2 (HRV2).

4. The method of claim 1, wherein the modified ECHO25 has one of the following characteristics:

(1) a genomic sequence of the modified ECHO25 has a sequence identity of at least 80% to a nucleotide sequence as shown in SEQ ID NOs: 13-16; and (2) a cDNA sequence of the modified ECHO25 has a sequence identity of at least 80% to a nucleotide sequence as shown in SEQ ID NOs: 8-11.

5. The method of claim 1, wherein the modified ECHO25is administered in combination with an additional pharmaceutically active agent having antitumor activity.

6. A modified ECHO25, comprising:

a substitution of an internal ribosome entry site (IRES) sequence in a 5' untranslated region (5'UTR) with an internal ribosome entry site sequence of human rhinovirus 2 (HRV2) as compared to a wild-type ECHO25, and an exogenous nucleic acid which is selected from the group consisting of a nucleic acid sequence encoding a cytokine, a nucleic acid sequence encoding an antitumor protein or polypeptide, and a target sequence of microRNA.

7. The modified ECHO25 of claim 6, wherein the modified ECHO25 has one of the following characteristics:

(1) a genomic sequence of the modified ECHO25 has a sequence identity of at least 80% to a nucleotide sequence as shown in SEQ ID NO: 13;

(2) a cDNA sequence of the modified ECHO25 has a sequence identity of at least 80% to a nucleotide sequence as shown in SEQ ID NO: 8.

8. An isolated nucleic acid molecule, comprising a genomic sequence or a cDNA sequence of the modified ECHO25 of claim 6.

9. The isolated nucleic acid molecule of claim 8, which consists of the genomic sequence of the modified ECHO25.

10. The isolated nucleic acid molecule of claim 8, which is a vector comprising the cDNA sequence of the modified ECHO25.

11. A method of treating a tumor, the method comprising administering, to a subject in need thereof, an effective amount of the modified ECHO25 of claim 6, or a medicament comprising the modified ECHO25.

12. The method of claim 1, wherein at least one of the following conditions is satisfied:

(i) the cytokine is GM-CSF;

(ii) the antitumor protein or polypeptide is a scFv against PD-1 or PD-L1;

(iii) the microRNA is miR-133 and/or miR-206.

13. The method of claim 1, wherein at least one of the following conditions is satisfied:

(i) the tumor is selected from the group consisting of gastric cancer, liver cancer, ovarian cancer, endometrial cancer, melanoma, prostate cancer, glioma, esophageal cancer, bladder cancer, lymphoma, leukemia, rhabdomyosarcoma, colorectal cancer, non-small cell lung cancer, cervical cancer, breast cancer, kidney cancer, and pancreatic cancer;

(ii) the subject is a human.

14. The modified ECHO25 of claim 6, wherein at least one of the following conditions is satisfied:

(i) the cytokine is GM-CSF;

(ii) the antitumor protein or polypeptide is a scFv against PD-1 or PD-L1;

(iii) the microRNA is miR-133 and/or miR-206.

15. The method of claim 11, wherein at least one of the following conditions is satisfied:

(i) the tumor is selected from the group consisting of gastric cancer, liver cancer, ovarian cancer, endometrial cancer, melanoma, prostate cancer, glioma, esophageal cancer, bladder cancer, lymphoma, leukemia, pharyngeal squamous cell carcinoma, thyroid cancer, rhabdomyosarcoma, colorectal cancer, non-small cell lung cancer, cervical cancer, breast cancer, kidney cancer, and pancreatic cancer;

(ii) the subject is a human.

16. A method of treating a tumor, the method comprising administering, to a subject in need thereof, an effective amount of an isolated nucleic acid molecule comprising a genomic sequence or a cDNA sequence of a modified ECHO25, or a medicament comprising the isolated nucleic acid molecule, wherein as compared to a genome of a wild-type ECHO25, a genome of the modified ECHO25 has an insertion of one or more exogenous nucleic acids, and wherein the one or more exogenous nucleic acids are selected from the group consisting of a nucleic acid sequence encoding a cytokine, a nucleic acid sequence encoding an antitumor protein or polypeptide, and a target sequence of microRNA.

17. The method of claim 16, wherein the isolated nucleic acid molecule consists of the genomic sequence of the modified ECHO25, or is a vector comprising the cDNA sequence of the modified ECHO25.

18. A method of treating a tumor, the method comprising administering, to a subject in need thereof, an effective amount of an isolated nucleic acid molecule comprising a genomic sequence or a cDNA sequence of the modified ECHO25 of claim 6, or a medicament comprising the isolated nucleic acid molecule.

* * * * *

SEQUENCE LISTING

<160> NUMBER OF SEQ ID NOS: 20

<210> SEQ ID NO 1
<211> LENGTH: 7428
<212> TYPE: DNA
<213> ORGANISM: Artificial Sequence
<220> FEATURE:
<223> OTHER INFORMATION: cDNA sequence of ECHO25-WT

<400> SEQUENCE: 1

```
ttaaaacagc ctgtgggttg ttcccaccca tagggcccac tgggcgctag cacactggta      60
ttgtggtacc tttgtgcgcc tgttttatct accccctcccc caaacgtgac ttagaagctc    120
aacacatgtg gtcagcaggt ggcccagtat accaactggg tcttgatcaa gcacttctgt    180
taccccggac cgagtatcaa taggctgctc acgcggctga aggagaaagt gttcgttatc    240
cggccaatta ctacgagaaa cctagtacca ccatggaagt tgcgcggcgt ttcgctccgc    300
acaaccccag tgtagatcag gccgatgagt caccgcactc ctcacgggcg accgtggcgg    360
tggctgcgct ggcggcctgc ccatggggca acccatggga cgcttcaata ccgacatggt    420
gtgaagagtc tattgtgcta attggtaatc ctccggcccc tgaatgcggc taatcccaac    480
tgcggagcag atacccacat gccagtgggc agtctgtcgt aacgggtaac tctgcagcgg    540
aaccgactac tttgggtgtc cgtgtttctt tttattcttt attggctgct tatggtgaca    600
attgagagat tgttgccata tagctattgg attggccatc cggtgacaaa cagaacaata    660
gtttatctat ttgttggttt cataccatta aattttaaag tattaaagac tatcaacttg    720
atcatactac ttaatacagc aaaatgggag ctcatgtgtc aacgcagaaa accggagcgc    780
atgagactgg tttgagcgcc agtgggaatt cggttattca ttacacaaca tcaattatta    840
caaggatgca tcttcaaatt cagcaaacag gcaagacttt tcacaagacc ccagcaaatt    900
taccgaaccc tatgaaggat gtcatgatta aatcactccc ggcgttaaat tcacccactg    960
tggaggaatg tggctacagt gaccgggtgc gctccattac tttgggtaat tcaacaatca   1020
ctacgcagga aagtgcaaat gtggtagttg gctatggtgt ctggccggag tatttgaggg   1080
atgaggaagc cacggcacaa gaccaaccca ctcaaccaga tgttgccacc tgtagattct   1140
acaccctaga atctgttatg tgggagaagt cctcggcggg ctggtggtgg aagtttccag   1200
atgctcttgc agagatgggc ctattcggtc aaaatatgct ataccattat ttgggaaggt   1260
caggctacac aatacacgtg caatgcaatg cgtcaaaatt ccaccaaggg tgccttcttg   1320
tagtctgtgt gccagaagcc gagatgggtt ctgcacagct tgataggaca ttgaatcata   1380
ccaaacttag caacacagaa cacgccagca cattcgggtc catgagttcc aatgaagctg   1440
gggccgtcca aaatgtagtg cacaatgccg ggatgggcgt tggagtgggt aacttgacca   1500
tctaccctca tcagtggatt aatcttagaa ccaacaattg tgccaccata gtaatgccgt   1560
acataaacag tgtgccaatg gataatatgt ttaggcatta caatttcacc cttatggtga   1620
ttccattcgc acagcttgat tatgcaccca gcgcgtccac tcacgttcca ataaccgtga   1680
cagttgcccc catgtgtgcc gaatacaacg ggctaagatt ggcaggtaaa cagggcttac   1740
caacaatgct cactccaggt agcaaccagt tcctcacgtc tgatgatttc cagtccccat   1800
cagcaatgcc acagtttgat gtaacgccgg agattgaaat ccccggtgac gtgaagaatt   1860
taatggaaat ggctgaagtt gattctgtgg tcccagtgaa taatctggat gataaggtaa   1920
attcaattga agcttataca atccccgtca aatcaatgag tggtattgcg acacaagtcg   1980
ttgggttcca attacaaccc ggggacgata gtgcgtttaa gaggacactg ttaggagaga   2040
```

```
ttttgaacta ctttgcaaat tggtcgggaa ttatcaaact gacattccca tactgcggtg   2100

cggcgatgac cactggcaca ttcctgatcg cctactcccc tcctggtgct ggcttccctg   2160

ctaaccgcaa ggactcaatg ttgggcactc acattgtctg ggacatagga ttgcaatcga   2220

gttgtgtgct ctgcgtgcca tggatcagtc agacaaacta ccgcttcgtg acgcatgacg   2280

cttatacaga cgctgggttt attacatgct ggtaccaaac aaacatagtg tcacccccag   2340

acatcccggc agacagtaca atcctatgtt ttgtttcagc ttgtaatgat ttctcggtgc   2400

gcttgttaag ggacacgcca ttcatatcac aaaacgcact tctccaaaat gacccggcta   2460

ctgccattgt tagatcagtg gaacgggtgg ccgataccat agcaagtggc ccaatgaatt   2520

ccgagagagt cccagcattg actgccgtcg agacgggtca cacatctcaa gttgttccca   2580

gtgatactat gcaaaccagg catgttgtta accatcacat tagatcggaa tcttcaatag   2640

agaattttct gagtagatcg gcatgcgttt acattgatgt gtatggcaca aaagagaatg   2700

gtgacatcga acgtttcact aactggaaga tcaacacacg ccaggttgtt cagctgaggc   2760

gcaagctgga gatgttcact tacatcagat ttgatgtgga aataacattc gtaattacaa   2820

gtactcaagg gacatcaacc caaacaagca ctggcacccc agtgctcaca catcaagtga   2880

tgtatgtgcc acccggaggc cccatacccg cgtcatatga ggattatagc tggcaaactt   2940

cgacaaaccc cagcgttttc tggacagaag ggaatgcacc ggctcgcatg tcaataccct   3000

ttatgagtgt gggcaatgcc tattgcaact tttatgatgg ctggtcacat ttctcgcaat   3060

ccggcgtgta tggtttcact accctgaaca acatgggaca gctgtttttc agacatgtga   3120

ataaggacac acttggccct tacaacagca cagtgcgtgt ctatttcaaa ccaaagcaca   3180

tcaaagcatg ggtgcccaga ccaccgcgtc tatgcgatta tgtgtatgca cataatgtcg   3240

atttcacccc cagaggagtc acggacataa gggaaaagat cacactggaa agagacgacc   3300

acacgccttc gatggtaaac cacggtgctt ttggacagca gtctggcgcc atttacgtgg   3360

gtaactacag agtggtaaat aggcacctgg ccacctatgc cgattggcag aattgcgtgt   3420

gggaagatta taatagagac ctcttagtga gcacaaccac agcgcacggg tgtgacacca   3480

tcgctaggtg tcaatgctgc acgggtgtct acttttgtgc ctcaaggaac aagcactacc   3540

cagttagctt tgaagggcca ggcctagtgg aagttcagga gagtgagtat tacccaaaga   3600

gataccagtc ccacgtgctg ttagccgcag ggttttctga accaggagac tgtggtggaa   3660

ttctcaggtg cgagcatggt gttatcggac tagttaccat gggtggcgaa ggcgtagtcg   3720

gctttgctga tgtgcgcgac ctgctgtggt tggaggatga tgcaatggaa caaggggtca   3780

agggttatgt agaacaattg ggcaatgcct tcggttccgg gttcaccaat caaatctgcg   3840

aacaagtcaa cctcctcaaa gaatcactag tgggccaaga ttccatacta gagaagtccc   3900

ttaaagctct tgtgaaaatc atttcagcac tggtaatagt agtgaggaac catgatgact   3960

taattactgt gactgccacc ctcgctctaa ttggctgcac ctcatcgccg tggcggtggc   4020

ttaaacagaa ggtgtcacag tattacggga tacccatggc tgagcgacaa aacaacgggt   4080

ggctcaaaaa gtttacagag atgaccaatg cctgcaaagg gatggagtgg attgccgtca   4140

agatccaaaa gtttatagaa tggctcaaga ttaaaatctt accagaggta aaggagaagc   4200

atgagttcct aaccagactt aaacaactcc cccttctgga aagccaaatt gccaccattg   4260

aacaaagtgc accgtcccag agtgatcagg aacaactctt ctcaaatgtt caatacttcg   4320

cccactactg cagaaagtac gcacctctgt atgctactga ggccaaaaga gtgttctccc   4380
```

```
ttgagaagaa aatgagtaac tacatacagt tcaagtccaa atgccgtatt gaaccagtat   4440
gtttgctatt gcacgggagt cctggagctg ggaaatcggt tgccaccaac ttaattgggc   4500
gatctctagc tgagaagttg aacagttcag tgtattctct accaccagac cctgaccact   4560
tcgatggcta taaacaacaa gccgttgtga ttatggacga cctatgccaa aatccagatg   4620
ggaaggatgt gtcattattt tgtcagatgg tgtcgagtgt tgactttgtc ccaccaatgg   4680
ctgccttgga agaaaaagga attttgttta cctctccctt tgtcttggcc tcaactaatg   4740
ctggttccat caatgccccg acggtgtcag acagcagggc tttggctaga agattccact   4800
ttgacatgaa catcgaggtt atatcaatgt acagccagaa tggcaagatt aacatgccca   4860
tgtcagtcaa aacatgcgac gaagagtgct gtccagttaa cttcaaaaag tgttgccccc   4920
ttgtgtgtgg aaaagccata cagtttatag atagaagaac tcaagtgagg tactccttgg   4980
acatgttggt cactgagatg tttagggagt acaaccatag gcacagcgtc ggggcaaccc   5040
ttgaggcact atttcaaggt ccaccagtat acagggagat caaaattact gttgcacctg   5100
ataccccacc accaccagct attgcatacc tactgaaatc attggacagt gaagcagtta   5160
gggagtactg taaagagaat ggatggctcg ttcctgaaat tagctctacc cttcatattg   5220
aaaaacatgt aagccgagcc tttatctgtc tccaggcact gacaactttt gtatccgtgg   5280
ccggtattat ctacatcatt tataaactat ttgcagggtt tcaaggcgcc tacacaggga   5340
tgcccaacca aaagccaaaa atacccacac taaggcaagc caaggtgcag ggacctgctt   5400
gtgagtttgc tgtagccatg atgaagagaa actccatcac agtgaagaca gagtatggtg   5460
agtttacaat gttgggcatc tacgacaggt gggccgtact accacgccat gcaaaacccg   5520
ggccaaccat ccttatgaat gaccaggaag ttggcgtact agatgcaaaa gaactagtgg   5580
ataaagatgg cacaaacctt gaactgacgc tgttgaagct tgaccggaat gaaaagttca   5640
gagacatcag aggtttcctg gccaaggaag aagtggaggt caatgaagct gttctagcaa   5700
taaacaccag caagttcccg aacatgtaca taccagttgg gcaagtaaca gactacggtt   5760
tcctgaacct ggggggcact ccgacgaaaa gaatgctcat gtacaatttt cctaccagag   5820
ctggccaatg tggtggtatt cttatgtcta ctggtaaggt gttggggata cacgttggtg   5880
gaaatggcca ccagggcttc tcagcagctc tccttaaaca ctacttcaat gatgaacaag   5940
gtgagattga atttattgaa agctcaaagg aagcaggttt cccagtcatt aatactccaa   6000
gcaagactaa attggaacca agtgtcttcc accaagtgtt tgaaggcaac aaggaacctg   6060
cagttctcag gaatggtgat ccacgactca aagcaaattt tgaggaggca atcttttcca   6120
aatatattgg taatgtgaac acacacgtag atgagtacat gatggaagcc gtggatcact   6180
acgcaggaca attggccaca ctggacatta atacggaacc tatgaaattg gaggatgcag   6240
tgtatggcac agaggggttg gaggcacttg atctaaccac cagtgcaggg tacccgtatg   6300
tagcactggg catcaagaag agagacatct tgtctaagaa gaccagagat ctgactaaat   6360
taaaggagtg tatggacaaa tatggtctaa accttccgat ggtgacctat gtgaaggatg   6420
agctcagatc agcagaaaaa gtggctaaag gcaagtctag acttattgag gcatccagcc   6480
tgaacgactc tgtagcgatg agacaaactt ttggcaatct gtacagaaca tttcatttga   6540
acccagggat tgtaactggc agtgcagttg ggtgtgatcc tgaccttttc tggagcaaaa   6600
tacctgtaat gctagatgga catctcatag cctttgatta ctctggatat gatgccagtt   6660
tgagccccgt gtggtttgct tgtttgaagc tattgctaga aaaactagga tactcacaca   6720
aagaaacaaa ttacattgac tatttgtgca attcccacca tttgtacaga gacaagcatt   6780
```

```
acttcgtgcg tggcggcatg ccatcaggtt gctccggtac cagcatcttc aactcaatga   6840

tcaacaacat cataatcagg acgctaatgt tgaaggtgta caaaggaatt gacctggatc   6900

gattcagaat gattgcctat ggcgatgatg ttattgcgtc ttacccctgg ccaatcgatg   6960

cctctttact tgctgaagcc ggcaaggggt atgggctgat catgacacca gcagataaag   7020

gggagtgttt taatgaagtc acctggacta atgtcacctt tttgaagaga tatttcagag   7080

cagatgagca ataccccttt gtggtccatc ctgttatccc aatgaaagac atccatgaat   7140

caattagatg gacaaaagac ccaaagaaca cccaagacca tgtgcgctct ttgtgcttgt   7200

tggcctggca caatggggag cacgaatatg aggaattcat caagaagatc agaagcgtcc   7260

cagtcgggcg ctgtctaacc cttcctgcgt tttggaccct gcgcaggaaa tggttggatt   7320

ccttttagat tagagacaat ttctgcaat ttgaattggc ttaaccctac cacactcacc   7380

gaactagaca acggtgtggt aggggtaaat tctccgcatt cggtgcgg              7428
```

<210> SEQ ID NO 2
<211> LENGTH: 507
<212> TYPE: RNA
<213> ORGANISM: Artificial Sequence
<220> FEATURE:
<223> OTHER INFORMATION: RNA sequence of the internal ribosome entry site of HRV2

<400> SEQUENCE: 2

```
aacuuagaag uuuuucacaa agaccaauag ccgguaauca gccagauuac ugaaggucaa     60

gcacuucugu uuccccgguc aauguugaua ugcuccaaca gggcaaaaac aacugcgauc    120

guuaaccgca aagcgccuac gcaaagcuua guagcaucuu ugaaaucguu uggcuggucg    180

auccgccauu uccccuggua gaccuggcag augaggcuag aaauacccca cuggcgacag    240

uguucuagcc ugcguggcug ccugcacacc cuaugggugu gaagccaaac aauggacaag    300

gugugaagag ccccgugugc ucgcuuugag uccuccggcc ccugaaugug gcuaaccuua    360

acccugcagc uagagcacgu aacccaaugu guaucuaguc guaaugagca auugcgggau    420

gggaccaacu acuuugggug uccguguuuc acuuuuuccu uuauauuugc uuauggugac    480

aauauauaca auauauauau uggcacc                                        507
```

<210> SEQ ID NO 3
<211> LENGTH: 22
<212> TYPE: RNA
<213> ORGANISM: Artificial Sequence
<220> FEATURE:
<223> OTHER INFORMATION: RNA sequence of miR-133 target sequence

<400> SEQUENCE: 3

```
acagcugguu gaaggggacc aa                                              22
```

<210> SEQ ID NO 4
<211> LENGTH: 22
<212> TYPE: RNA
<213> ORGANISM: Artificial Sequence
<220> FEATURE:
<223> OTHER INFORMATION: RNA sequence of miR-206 target sequence

<400> SEQUENCE: 4

```
ccacacacuu ccuuacauuc ca                                              22
```

<210> SEQ ID NO 5
<211> LENGTH: 102

```
<212> TYPE: RNA
<213> ORGANISM: Artificial Sequence
<220> FEATURE:
<223> OTHER INFORMATION: RNA sequence of tandem sequence of miR-133
      target sequence and miR-206 target sequence

<400> SEQUENCE: 5

acagcugguu gaaggggacc aacgauacag cugguugaag gggaccaaac cgguccacac     60

acuuccuuac auuccaucac ccacacacuu ccuuacauuc ca                       102


<210> SEQ ID NO 6
<211> LENGTH: 435
<212> TYPE: DNA
<213> ORGANISM: Artificial Sequence
<220> FEATURE:
<223> OTHER INFORMATION: DNA sequence of GM-CSF gene

<400> SEQUENCE: 6

atgtggctgc agagcctgct gctcttgggc actgtggcct gcagcatctc tgcacccgcc     60

cgctcgccca gccccagcac gcagccctgg gagcatgtga atgccatcca ggaggcccgg    120

cgtctcctga acctgagtag agacactgct gctgagatga atgaaacagt agaagtcatc    180

tcagaaatgt ttgacctcca ggagccgacc tgcctacaga cccgcctgga gctgtacaag    240

cagggcctgc ggggcagcct caccaagctc aagggcccct tgaccatgat ggccagccac    300

tacaagcagc actgccctcc aaccccggaa acttcctgtg caacccagat tatcaccttt    360

gaaagtttca aagagaacct gaaggacttt ctgcttgtca tcccctttga ctgctgggag    420

ccagtccagg agtga                                                     435


<210> SEQ ID NO 7
<211> LENGTH: 795
<212> TYPE: DNA
<213> ORGANISM: Artificial Sequence
<220> FEATURE:
<223> OTHER INFORMATION: DNA sequence of Anti-PD-1 scFv

<400> SEQUENCE: 7

atgaagcacc tgtggttctt cctgctgctg gtggccgctc ctaggtgggt gctgtcccag     60

gtgcagctgg tgcagagcgg cgtggaggtg aagaagcccg gcgcttccgt gaaggtgtcc    120

tgcaaggcct ccggctacac cttcaccaac tactacatgt actgggtgag gcaggcccct    180

ggacagggac tggagtggat gggcggcatc aacccttcca acggcggcac caacttcaac    240

gagaagttca agaaccgggt gaccctgacc accgactcct ccaccaccac cgcctacatg    300

gagctgaagt ccctgcagtt tgacgacacc gccgtgtact actgcgccag gagggactac    360

cggttcgaca tgggcttcga ctactggggc cagggcacaa ccgtgaccgt gtccagcgga    420

ggtggcggat ctggaggggg tggtagcggt ggaggcggga gtgagatcgt gctgacccag    480

tcccctgcta cactgtccct gtcccccggc gagagggcta cactgagctg cagggcctcc    540

aagggcgtgt ccacctccgg ctactcctac ctgcactggt accagcagaa gcctggacag    600

gctcccaggc tgctgatcta cctggcctcc tacctggagt ccggcgtgcc tgctaggttt    660

tccggcagcg gcagcggcac cgatttcacc ctgaccatct cctccctgga gcccgaggac    720

ttcgccgtgt actactgcca gcactccagg gatctgcctc tgaccttcgg cggcggcacc    780

aaggtggaga tcaag                                                     795


<210> SEQ ID NO 8
<211> LENGTH: 7309
```

```
<212> TYPE: DNA
<213> ORGANISM: Artificial Sequence
<220> FEATURE:
<223> OTHER INFORMATION: cDNA sequence of ECHO25-HRV2

<400> SEQUENCE: 8

ttaaaacagc ctgtgggttg ttcccaccca tagggcccac tgggcgctag cacactggta     60

ttgtggtacc tttgtgcgcc tgttttatct acccctcccc caaacgtgac ttagaagaac    120

ttagaagttt ttcacaaaga ccaatagccg gtaatcagcc agattactga aggtcaagca    180

cttctgtttc cccggtcaat gttgatatgc tccaacaggg caaaaacaac tgcgatcgtt    240

aaccgcaaag cgcctacgca aagcttagta gcatctttga aatcgtttgg ctggtcgatc    300

cgccatttcc cctggtagac ctggcagatg aggctagaaa taccccactg gcgacagtgt    360

tctagcctgc gtggctgcct gcacacccta tgggtgtgaa gccaaacaat ggacaaggtg    420

tgaagagccc cgtgtgctcg ctttgagtcc tccggcccct gaatgtggct aaccttaacc    480

ctgcagctag agcacgtaac ccaatgtgta tctagtcgta atgagcaatt gcgggatggg    540

accaactact ttgggtgtcc gtgtttcact tttcctttta tatttgctta tggtgacaat    600

atatacaata tatatattgg caccatggga gctcatgtgt caacgcagaa aaccggagcg    660

catgagactg gtttgagcgc cagtgggaat tcggttattc attacacaac atcaattatt    720

acaaggatgc atcttcaaat tcagcaaaca ggcaagactt ttcacaagac cccagcaaat    780

ttaccgaacc ctatgaagga tgtcatgatt aaatcactcc cggcgttaaa ttcacccact    840

gtggaggaat gtggctacag tgaccgggtg cgctccatta ctttgggtaa ttcaacaatc    900

actacgcagg aaagtgcaaa tgtggtagtt ggctatggtg tctggccgga gtatttgagg    960

gatgaggaag ccacggcaca agaccaaccc actcaaccag atgttgccac ctgtagattc   1020

tacaccctag aatctgttat gtgggagaag tcctcggcgg gctggtggtg gaagtttcca   1080

gatgctcttg cagagatggg cctattcggt caaaatatgc tataccatta tttgggaagg   1140

tcaggctaca caatacacgt gcaatgcaat gcgtcaaaat tccaccaagg gtgccttctt   1200

gtagtctgtg tgccagaagc cgagatgggt tctgcacagc ttgataggac attgaatcat   1260

accaaactta gcaacacaga acacgccagc acattcgggt ccatgagttc caatgaagct   1320

ggggccgtcc aaaatgtagt gcacaatgcc gggatgggcg ttggagtggg taacttgacc   1380

atctaccctc atcagtggat taatcttaga accaacaatt gtgccaccat agtaatgccg   1440

tacataaaca gtgtgccaat ggataatatg tttaggcatt acaatttcac ccttatggtg   1500

attccattcg cacagcttga ttatgcaccc agcgcgtcca ctcacgttcc aataaccgtg   1560

acagttgccc ccatgtgtgc cgaatacaac gggctaagat tggcaggtaa acagggctta   1620

ccaacaatgc tcactccagg tagcaaccag ttcctcacgt ctgatgattt ccagtcccca   1680

tcagcaatgc cacagtttga tgtaacgccg gagattgaaa tccccggtga cgtgaagaat   1740

ttaatggaaa tggctgaagt tgattctgtg gtcccagtga ataatctgga tgataaggta   1800

aattcaattg aagcttatac aatccccgtc aaatcaatga gtggtattgc gacacaagtc   1860

gttgggttcc aattacaacc cggggacgat agtgcgttta agaggacact gttaggagag   1920

attttgaact actttgcaaa ttggtcggga attatcaaac tgacattccc atactgcggt   1980

gcggcgatga ccactggcac attcctgatc gcctactccc ctcctggtgc tggcttccct   2040

gctaaccgca aggactcaat gttgggcact cacattgtct gggacatagg attgcaatcg   2100

agttgtgtgc tctgcgtgcc atggatcagt cagacaaact accgcttcgt gacgcatgac   2160
```

-continued

```
gcttatacag acgctgggtt tattacatgc tggtaccaaa caaacatagt gtcacccccca 2220
gacatcccgg cagacagtac aatcctatgt tttgtttcag cttgtaatga tttctcggtg 2280
cgcttgttaa gggacacgcc attcatatca caaaacgcac ttctccaaaa tgacccggct 2340
actgccattg ttagatcagt ggaacgggtg gccgatacca tagcaagtgg cccaatgaat 2400
tccgagagag tcccagcatt gactgccgtc gagacgggtc acacatctca agttgttccc 2460
agtgatacta tgcaaaccag gcatgttgtt aaccatcaca ttagatcgga atcttcaata 2520
gagaattttc tgagtagatc ggcatgcgtt tacattgatg tgtatggcac aaaagagaat 2580
ggtgacatcg aacgtttcac taactggaag atcaacacac gccaggttgt tcagctgagg 2640
cgcaagctgg agatgttcac ttacatcaga tttgatgtgg aaataacatt cgtaattaca 2700
agtactcaag ggacatcaac ccaaacaagc actggcaccc cagtgctcac acatcaagtg 2760
atgtatgtgc cacccggagg ccccataccc gcgtcatatg aggattatag ctggcaaact 2820
tcgacaaacc ccagcgtttt ctggacagaa gggaatgcac cggctcgcat gtcaataccc 2880
tttatgagtg tgggcaatgc ctattgcaac ttttatgatg gctggtcaca tttctcgcaa 2940
tccggcgtgt atggtttcac taccctgaac aacatgggac agctgttttt cagacatgtg 3000
aataaggaca cacttggccc ttacaacagc acagtgcgtg tctatttcaa accaaagcac 3060
atcaaagcat gggtgcccag accaccgcgt ctatgcgatt atgtgtatgc acataatgtc 3120
gatttcaccc ccagaggagt cacggacata agggaaaaga tcacactgga aagagacgac 3180
cacacgcctt cgatggtaaa ccacggtgct tttggacagc agtctggcgc catttacgtg 3240
ggtaactaca gagtggtaaa taggcacctg gccacctatg ccgattggca gaattgcgtg 3300
tgggaagatt ataatagaga cctcttagtg agcacaacca cagcgcacgg gtgtgacacc 3360
atcgctaggt gtcaatgctg cacgggtgtc tacttttgtg cctcaaggaa caagcactac 3420
ccagttagct ttgaagggcc aggcctagtg gaagttcagg agagtgagta ttacccaaag 3480
agataccagt cccacgtgct gttagccgca gggttttctg aaccaggaga ctgtggtgga 3540
attctcaggt gcgagcatgg tgttatcgga ctagttacca tgggtggcga aggcgtagtc 3600
ggctttgctg atgtgcgcga cctgctgtgg ttggaggatg atgcaatgga acaaggggtc 3660
aagggttatg tagaacaatt gggcaatgcc ttcggttccg ggttcaccaa tcaaatctgc 3720
gaacaagtca acctcctcaa agaatcacta gtgggccaag attccatact agagaagtcc 3780
cttaaagctc ttgtgaaaat catttcagca ctggtaatag tagtgaggaa ccatgatgac 3840
ttaattactg tgactgccac cctcgctcta attggctgca cctcatcgcc gtggcggtgg 3900
cttaaacaga aggtgtcaca gtattacggg atacccatgg ctgagcgaca aaacaacggg 3960
tggctcaaaa agtttacaga gatgaccaat gcctgcaaag ggatggagtg gattgccgtc 4020
aagatccaaa agtttataga atggctcaag attaaaatct taccagaggt aaaggagaag 4080
catgagttcc taaccagact taaacaactc cccctttctgg aaagccaaat tgccaccatt 4140
gaacaaagtg caccgtccca gagtgatcag gaacaactct tctcaaatgt tcaatacttc 4200
gcccactact gcagaaagta cgcacctctg tatgctactg aggccaaaag agtgttctcc 4260
cttgagaaga aaatgagtaa ctacatacag ttcaagtcca aatgccgtat tgaaccagta 4320
tgtttgctat tgcacgggag tcctggagct gggaaatcgg ttgccaccaa cttaattggg 4380
cgatctctag ctgagaagtt gaacagttca gtgtattctc taccaccaga ccctgaccac 4440
ttcgatggct ataaacaaca agccgttgtg attatggacg acctatgcca aaatccagat 4500
gggaaggatg tgtcattatt ttgtcagatg gtgtcgagtg ttgactttgt cccaccaatg 4560
```

```
gctgccttgg aagaaaaagg aattttgttt acctctccct ttgtcttggc ctcaactaat   4620
gctggttcca tcaatgcccc gacggtgtca gacagcaggg ctttggctag aagattccac   4680
tttgacatga acatcgaggt tatatcaatg tacagccaga atggcaagat taacatgccc   4740
atgtcagtca aaacatgcga cgaagagtgc tgtccagtta acttcaaaaa gtgttgcccc   4800
cttgtgtgtg gaaaagccat acagtttata gatagaagaa ctcaagtgag gtactccttg   4860
gacatgttgg tcactgagat gtttagggag tacaaccata ggcacagcgt cggggcaacc   4920
cttgaggcac tatttcaagg tccaccagta tacagggaga tcaaaattac tgttgcacct   4980
gataccccac caccaccagc tattgcatac ctactgaaat cattggacag tgaagcagtt   5040
agggagtact gtaaagagaa tggatggctc gttcctgaaa ttagctctac ccttcatatt   5100
gaaaaacatg taagccgagc ctttatctgt ctccaggcac tgacaacttt tgtatccgtg   5160
gccggtatta tctacatcat ttataaacta tttgcagggt ttcaaggcgc ctacacaggg   5220
atgcccaacc aaaagccaaa aatacccaca ctaaggcaag ccaaggtgca gggacctgct   5280
tgtgagtttg ctgtagccat gatgaagaga aactccatca cagtgaagac agagtatggt   5340
gagtttacaa tgttgggcat ctacgacagg tgggccgtac taccacgcca tgcaaaaccc   5400
gggccaacca tccttatgaa tgaccaggaa gttggcgtac tagatgcaaa agaactagtg   5460
gataaagatg gcacaaacct tgaactgacg ctgttgaagc ttgaccggaa tgaaaagttc   5520
agagacatca gaggtttcct ggccaaggaa gaagtggagg tcaatgaagc tgttctagca   5580
ataaacacca gcaagttccc gaacatgtac ataccagttg ggcaagtaac agactacggt   5640
ttcctgaacc tgggggggcac tccgacgaaa agaatgctca tgtacaattt tcctaccaga   5700
gctggccaat gtggtggtat tcttatgtct actggtaagg tgttggggat acacgttggt   5760
ggaaatggcc accagggctt ctcagcagct ctccttaaac actacttcaa tgatgaacaa   5820
ggtgagattg aatttattga aagctcaaag gaagcaggtt tcccagtcat taatactcca   5880
agcaagacta aattggaacc aagtgtcttc caccaagtgt ttgaaggcaa caaggaacct   5940
gcagttctca ggaatggtga tccacgactc aaagcaaatt ttgaggaggc aatcttttcc   6000
aaatatattg gtaatgtgaa cacacacgta gatgagtaca tgatggaagc cgtggatcac   6060
tacgcaggac aattggccac actggacatt aatacggaac ctatgaaatt ggaggatgca   6120
gtgtatggca cagaggggtt ggaggcactt gatctaacca ccagtgcagg gtacccgtat   6180
gtagcactgg gcatcaagaa gagagacatc ttgtctaaga agaccagaga tctgactaaa   6240
ttaaaggagt gtatggacaa atatggtcta aaccttccga tggtgaccta tgtgaaggat   6300
gagctcagat cagcagaaaa agtggctaaa ggcaagtcta gacttattga ggcatccagc   6360
ctgaacgact ctgtagcgat gagacaaact tttggcaatc tgtacagaac atttcatttg   6420
aacccaggga ttgtaactgg cagtgcagtt gggtgtgatc ctgacctttt ctggagcaaa   6480
atacctgtaa tgctagatgg acatctcata gcctttgatt actctggata tgatgccagt   6540
ttgagccccg tgtggtttgc ttgtttgaag ctattgctag aaaaactagg atactcacac   6600
aaagaaacaa attacattga ctatttgtgc aattcccacc atttgtacag agacaagcat   6660
tacttcgtgc gtggcggcat gccatcaggt tgctccggta ccagcatctt caactcaatg   6720
atcaacaaca tcataatcag gacgctaatg ttgaaggtgt acaaaggaat tgacctggat   6780
cgattcagaa tgattgccta tggcgatgat gttattgcgt cttacccctg gccaatcgat   6840
gcctctttac ttgctgaagc cggcaagggg tatgggctga tcatgacacc agcagataaa   6900
```

```
ggggagtgtt ttaatgaagt cacctggact aatgtcacct ttttgaagag atatttcaga   6960

gcagatgagc aataccccctt tgtggtccat cctgttatcc caatgaaaga catccatgaa   7020

tcaattagat ggacaaaaga cccaaagaac acccaagacc atgtgcgctc tttgtgcttg   7080

ttggcctggc acaatgggga gcacgaatat gaggaattca tcaagaagat cagaagcgtc   7140

ccagtcgggc gctgtctaac ccttcctgcg ttttggaccc tgcgcaggaa atggttggat   7200

tccttttaga ttagagacaa ttttctgcaa tttgaattgg cttaacccta ccacactcac   7260

cgaactagac aacggtgtgg taggggtaaa ttctccgcat tcggtgcgg                7309
```

<210> SEQ ID NO 9
<211> LENGTH: 7530
<212> TYPE: DNA
<213> ORGANISM: Artificial Sequence
<220> FEATURE:
<223> OTHER INFORMATION: cDNA sequence of ECHO25-miR133&206T

<400> SEQUENCE: 9

```
ttaaaacagc ctgtgggttg ttcccaccca tagggcccac tgggcgctag cacactggta     60

ttgtggtacc tttgtgcgcc tgttttatct acccctcccc caaacgtgac ttagaagctc    120

aacacatgtg gtcagcaggt ggcccagtat accaactggg tcttgatcaa gcacttctgt    180

taccccggac cgagtatcaa taggctgctc acgcggctga aggagaaagt gttcgttatc    240

cggccaatta ctacgagaaa cctagtacca ccatggaagt tgcgcggcgt ttcgctccgc    300

acaaccccag tgtagatcag gccgatgagt caccgcactc ctcacgggcg accgtggcgg    360

tggctgcgct ggcggcctgc ccatggggca acccatggga cgcttcaata ccgacatggt    420

gtgaagagtc tattgtgcta attggtaatc ctccggcccc tgaatgcggc taatcccaac    480

tgcggagcag atacccacat gccagtgggc agtctgtcgt aacgggtaac tctgcagcgg    540

aaccgactac tttgggtgtc cgtgtttctt tttattcttt attggctgct tatggtgaca    600

attgagagat tgttgccata tagctattgg attggccatc cggtgacaaa cagaacaata    660

gtttatctat ttgttggttt cataccatta aattttaaag tattaaagac tatcaacttg    720

atcatactac ttaatacagc aaaatgggag ctcatgtgtc aacgcagaaa accggagcgc    780

atgagactgg tttgagcgcc agtgggaatt cggttattca ttacacaaca tcaattatta    840

caaggatgca tcttcaaatt cagcaaacag gcaagacttt tcacaagacc ccagcaaatt    900

taccgaaccc tatgaaggat gtcatgatta aatcactccc ggcgttaaat tcacccactg    960

tggaggaatg tggctacagt gaccgggtgc gctccattac tttgggtaat tcaacaatca   1020

ctacgcagga aagtgcaaat gtggtagttg gctatggtgt ctggccggag tatttgaggg   1080

atgaggaagc cacggcacaa gaccaaccca ctcaaccaga tgttgccacc tgtagattct   1140

acaccctaga atctgttatg tgggagaagt cctcggcggg ctggtggtgg aagtttccag   1200

atgctcttgc agagatgggc ctattcggtc aaaatatgct ataccattat ttgggaaggt   1260

caggctacac aatacacgtg caatgcaatg cgtcaaaatt ccaccaaggg tgccttcttg   1320

tagtctgtgt gccagaagcc gagatgggtt ctgcacagct tgataggaca ttgaatcata   1380

ccaaacttag caacacagaa cacgccagca cattcgggtc catgagttcc aatgaagctg   1440

gggccgtcca aaatgtagtg cacaatgccg ggatgggcgt tggagtgggt aacttgacca   1500

tctaccctca tcagtggatt aatcttagaa ccaacaattg tgccaccata gtaatgccgt   1560

acataaacag tgtgccaatg gataatatgt ttaggcatta caatttcacc cttatggtga   1620

ttccattcgc acagcttgat tatgcaccca gcgcgtccac tcacgttcca ataaccgtga   1680
```

```
cagttgcccc catgtgtgcc gaatacaacg ggctaagatt ggcaggtaaa cagggcttac   1740
caacaatgct cactccaggt agcaaccagt tcctcacgtc tgatgatttc cagtccccat   1800
cagcaatgcc acagtttgat gtaacgccgg agattgaaat ccccggtgac gtgaagaatt   1860
taatggaaat ggctgaagtt gattctgtgg tcccagtgaa taatctggat gataaggtaa   1920
attcaattga agcttataca atccccgtca aatcaatgag tggtattgcg acacaagtcg   1980
ttgggttcca attacaaccc ggggacgata gtgcgtttaa gaggacactg ttaggagaga   2040
ttttgaacta ctttgcaaat tggtcgggaa ttatcaaact gacattccca tactgcggtg   2100
cggcgatgac cactggcaca ttcctgatcg cctactcccc tcctggtgct ggcttccctg   2160
ctaaccgcaa ggactcaatg ttgggcactc acattgtctg ggacatagga ttgcaatcga   2220
gttgtgtgct ctgcgtgcca tggatcagtc agacaaacta ccgcttcgtg acgcatgacg   2280
cttatacaga cgctgggttt attacatgct ggtaccaaac aaacatagtg tcacccccag   2340
acatcccggc agacagtaca atcctatgtt ttgtttcagc ttgtaatgat ttctcggtgc   2400
gcttgttaag ggacacgcca ttcatatcac aaaacgcact tctccaaaat gacccggcta   2460
ctgccattgt tagatcagtg gaacgggtgg ccgataccat agcaagtggc ccaatgaatt   2520
ccgagagagt cccagcattg actgccgtcg agacgggtca cacatctcaa gttgttccca   2580
gtgatactat gcaaaccagg catgttgtta accatcacat tagatcggaa tcttcaatag   2640
agaattttct gagtagatcg gcatgcgttt acattgatgt gtatggcaca aaagagaatg   2700
gtgacatcga acgtttcact aactggaaga tcaacacacg ccaggttgtt cagctgaggc   2760
gcaagctgga gatgttcact tacatcagat ttgatgtgga aataacattc gtaattacaa   2820
gtactcaagg gacatcaacc caaacaagca ctggcacccc agtgctcaca catcaagtga   2880
tgtatgtgcc acccggaggc cccatacccg cgtcatatga ggattatagc tggcaaactt   2940
cgacaaaccc cagcgttttc tggacagaag ggaatgcacc ggctcgcatg tcaataccct   3000
ttatgagtgt gggcaatgcc tattgcaact tttatgatgg ctggtcacat ttctcgcaat   3060
ccggcgtgta tggtttcact accctgaaca acatgggaca gctgtttttc agacatgtga   3120
ataaggacac acttggccct tacaacagca cagtgcgtgt ctatttcaaa ccaaagcaca   3180
tcaaagcatg ggtgcccaga ccaccgcgtc tatgcgatta tgtgtatgca cataatgtcg   3240
atttcacccc cagaggagtc acggacataa gggaaaagat cacactggaa agagacgacc   3300
acacgccttc gatggtaaac cacggtgctt ttggacagca gtctggcgcc atttacgtgg   3360
gtaactacag agtggtaaat aggcacctgg ccacctatgc cgattggcag aattgcgtgt   3420
gggaagatta taatagagac ctcttagtga gcacaaccac agcgcacggg tgtgacacca   3480
tcgctaggtg tcaatgctgc acgggtgtct acttttgtgc ctcaaggaac aagcactacc   3540
cagttagctt tgaagggcca ggcctagtgg aagttcagga gagtgagtat tacccaaaga   3600
gataccagtc ccacgtgctg ttagccgcag ggttttctga accaggagac tgtggtggaa   3660
ttctcaggtg cgagcatggt gttatcggac tagttaccat gggtggcgaa ggcgtagtcg   3720
gctttgctga tgtgcgcgac ctgctgtggt tggaggatga tgcaatggaa caaggggtca   3780
agggttatgt agaacaattg ggcaatgcct tcggttccgg gttcaccaat caaatctgcg   3840
aacaagtcaa cctcctcaaa gaatcactag tgggccaaga ttccatacta gagaagtccc   3900
ttaaagctct tgtgaaaatc atttcagcac tggtaatagt agtgaggaac catgatgact   3960
taattactgt gactgccacc ctcgctctaa ttggctgcac ctcatcgccg tggcggtggc   4020
```

-continued

```
ttaaacagaa ggtgtcacag tattacggga tacccatggc tgagcgacaa aacaacgggt   4080
ggctcaaaaa gtttacagag atgaccaatg cctgcaaagg gatggagtgg attgccgtca   4140
agatccaaaa gtttatagaa tggctcaaga ttaaaatctt accagaggta aaggagaagc   4200
atgagttcct aaccagactt aaacaactcc cccttctgga aagccaaatt gccaccattg   4260
aacaaagtgc accgtcccag agtgatcagg aacaactctt ctcaaatgtt caatacttcg   4320
cccactactg cagaaagtac gcacctctgt atgctactga ggccaaaaga gtgttctccc   4380
ttgagaagaa aatgagtaac tacatacagt tcaagtccaa atgccgtatt gaaccagtat   4440
gtttgctatt gcacgggagt cctggagctg ggaaatcggt tgccaccaac ttaattgggc   4500
gatctctagc tgagaagttg aacagttcag tgtattctct accaccagac cctgaccact   4560
tcgatggcta taaacaacaa gccgttgtga ttatggacga cctatgccaa aatccagatg   4620
ggaaggatgt gtcattattt tgtcagatgg tgtcgagtgt tgactttgtc ccaccaatgg   4680
ctgccttgga agaaaaagga attttgttta cctctccctt tgtcttggcc tcaactaatg   4740
ctggttccat caatgccccg acggtgtcag acagcagggc tttggctaga agattccact   4800
ttgacatgaa catcgaggtt atatcaatgt acagccagaa tggcaagatt aacatgccca   4860
tgtcagtcaa aacatgcgac gaagagtgct gtccagttaa cttcaaaaag tgttgccccc   4920
ttgtgtgtgg aaaagccata cagtttatag atagaagaac tcaagtgagg tactccttgg   4980
acatgttggt cactgagatg tttagggagt acaaccatag gcacagcgtc ggggcaaccc   5040
ttgaggcact atttcaaggt ccaccagtat acagggagat caaaattact gttgcacctg   5100
ataccccacc accaccagct attgcatacc tactgaaatc attggacagt gaagcagtta   5160
gggagtactg taaagagaat ggatggctcg ttcctgaaat tagctctacc cttcatattg   5220
aaaaacatgt aagccgagcc tttatctgtc tccaggcact gacaactttt gtatccgtgg   5280
ccggtattat ctacatcatt tataaactat ttgcagggtt tcaaggcgcc tacacaggga   5340
tgcccaacca aaagccaaaa atacccacac taaggcaagc caaggtgcag ggacctgctt   5400
gtgagtttgc tgtagccatg atgaagagaa actccatcac agtgaagaca gagtatggtg   5460
agtttacaat gttgggcatc tacgacaggt gggccgtact accacgccat gcaaaacccg   5520
ggccaaccat ccttatgaat gaccaggaag ttggcgtact agatgcaaaa gaactagtgg   5580
ataaagatgg cacaaacctt gaactgacgc tgttgaagct tgaccggaat gaaaagttca   5640
gagacatcag aggtttcctg gccaaggaag aagtggaggt caatgaagct gttctagcaa   5700
taaacaccag caagttcccg aacatgtaca taccagttgg gcaagtaaca gactacggtt   5760
tcctgaacct gggggcact ccgacgaaaa gaatgctcat gtacaatttt cctaccagag   5820
ctggccaatg tggtggtatt cttatgtcta ctggtaaggt gttggggata cacgttggtg   5880
gaaatggcca ccagggcttc tcagcagctc tccttaaaca ctacttcaat gatgaacaag   5940
gtgagattga atttattgaa agctcaaagg aagcaggttt cccagtcatt aatactccaa   6000
gcaagactaa attggaacca agtgtcttcc accaagtgtt tgaaggcaac aaggaacctg   6060
cagttctcag gaatggtgat ccacgactca aagcaaattt tgaggaggca atcttttcca   6120
aatatattgg taatgtgaac acacacgtag atgagtacat gatggaagcc gtggatcact   6180
acgcaggaca attggccaca ctggacatta atacggaacc tatgaaattg gaggatgcag   6240
tgtatggcac agaggggttg gaggcacttg atctaaccac cagtgcaggg tacccgtatg   6300
tagcactggg catcaagaag agagacatct tgtctaagaa gaccagagat ctgactaaat   6360
taaaggagtg tatggacaaa tatggtctaa accttccgat ggtgacctat gtgaaggatg   6420
```

agctcagatc agcagaaaaa gtggctaaag gcaagtctag acttattgag gcatccagcc 6480
tgaacgactc tgtagcgatg agacaaactt ttggcaatct gtacagaaca tttcatttga 6540
acccagggat tgtaactggc agtgcagttg ggtgtgatcc tgaccttttc tggagcaaaa 6600
tacctgtaat gctagatgga catctcatag cctttgatta ctctggatat gatgccagtt 6660
tgagccccgt gtggtttgct tgtttgaagc tattgctaga aaaactagga tactcacaca 6720
aagaaacaaa ttacattgac tatttgtgca attcccacca tttgtacaga gacaagcatt 6780
acttcgtgcg tggcggcatg ccatcaggtt gctccggtac cagcatcttc aactcaatga 6840
tcaacaacat cataatcagg acgctaatgt tgaaggtgta caaaggaatt gacctggatc 6900
gattcagaat gattgcctat ggcgatgatg ttattgcgtc ttacccctgg ccaatcgatg 6960
cctctttact tgctgaagcc ggcaaggggt atgggctgat catgacacca gcagataaag 7020
gggagtgttt taatgaagtc acctggacta atgtcacctt tttgaagaga tatttcagag 7080
cagatgagca ataccccttt gtggtccatc ctgttatccc aatgaaagac atccatgaat 7140
caattagatg gacaaaagac ccaaagaaca cccaagacca tgtgcgctct ttgtgcttgt 7200
tggcctggca caatggggag cacgaatatg aggaattcat caagaagatc agaagcgtcc 7260
cagtcgggcg ctgtctaacc cttcctgcgt tttggaccct gcgcaggaaa tggttggatt 7320
ccttttagat tagagacaca gctggttgaa ggggaccaac gatacagctg gttgaagggg 7380
accaaaccgg tccacacact tccttacatt ccatcaccca cacacttcct tacattccaa 7440
attttctgca atttgaattg gcttaaccct accacactca ccgaactaga caacggtgtg 7500
gtaggggtaa attctccgca ttcggtgcgg 7530

<210> SEQ ID NO 10
<211> LENGTH: 7905
<212> TYPE: DNA
<213> ORGANISM: Artificial Sequence
<220> FEATURE:
<223> OTHER INFORMATION: cDNA sequence of ECHO25-GM-CSF

<400> SEQUENCE: 10
ttaaaacagc ctgtgggttg ttcccaccca tagggcccac tgggcgctag cacactggta 60
ttgtggtacc tttgtgcgcc tgttttatct acccctcccc caaacgtgac ttagaagctc 120
aacacatgtg gtcagcaggt ggcccagtat accaactggg tcttgatcaa gcacttctgt 180
taccccggac cgagtatcaa taggctgctc acgcggctga aggagaaagt gttcgttatc 240
cggccaatta ctacgagaaa cctagtacca ccatggaagt tgcgcggcgt ttcgctccgc 300
acaaccccag tgtagatcag gccgatgagt caccgcactc ctcacgggcg accgtggcgg 360
tggctgcgct ggcggcctgc ccatggggca acccatggga cgcttcaata ccgacatggt 420
gtgaagagtc tattgtgcta attggtaatc ctccggcccc tgaatgcggc taatcccaac 480
tgcggagcag atacccacat gccagtgggc agtctgtcgt aacgggtaac tctgcagcgg 540
aaccgactac tttgggtgtc cgtgtttctt tttattcttt attggctgct tatggtgaca 600
attgagagat tgttgccata tagctattgg attggccatc cggtgacaaa cagaacaata 660
gtttatctat ttgttggttt cataccatta aattttaaag tattaaagac tatcaacttg 720
atcatactac ttaatacagc aaaatgggag ctcatgtgtc aacgcagaaa accggagcgc 780
atgagactgg tttgagcgcc agtgggaatt cggttattca ttacacaaca tcaattatta 840
caaggatgca tcttcaaatt cagcaaacag gcaagacttt tcacaagacc ccagcaaatt 900

-continued

```
taccgaaccc tatgaaggat gtcatgatta aatcactccc ggcgttaaat tcacccactg    960
tggaggaatg tggctacagt gaccgggtgc gctccattac tttgggtaat tcaacaatca   1020
ctacgcagga aagtgcaaat gtggtagttg gctatggtgt ctggccggag tatttgaggg   1080
atgaggaagc cacggcacaa gaccaaccca ctcaaccaga tgttgccacc tgtagattct   1140
acaccctaga atctgttatg tgggagaagt cctcggcggg ctggtggtgg aagtttccag   1200
atgctcttgc agagatgggc ctattcggtc aaaatatgct ataccattat ttgggaaggt   1260
caggctacac aatacacgtg caatgcaatg cgtcaaaatt ccaccaaggg tgccttcttg   1320
tagtctgtgt gccagaagcc gagatgggtt ctgcacagct tgataggaca ttgaatcata   1380
ccaaacttag caacacagaa cacgccagca cattcgggtc catgagttcc aatgaagctg   1440
gggccgtcca aaatgtagtg cacaatgccg ggatgggcgt tggagtgggt aacttgacca   1500
tctaccctca tcagtggatt aatcttagaa ccaacaattg tgccaccata gtaatgccgt   1560
acataaacag tgtgccaatg gataatatgt ttaggcatta caatttcacc cttatggtga   1620
ttccattcgc acagcttgat tatgcaccca gcgcgtccac tcacgttcca ataaccgtga   1680
cagttgcccc catgtgtgcc gaatacaacg ggctaagatt ggcaggtaaa cagggcttac   1740
caacaatgct cactccaggt agcaaccagt tcctcacgtc tgatgatttc cagtccccat   1800
cagcaatgcc acagtttgat gtaacgccgg agattgaaat ccccggtgac gtgaagaatt   1860
taatggaaat ggctgaagtt gattctgtgg tcccagtgaa taatctggat gataaggtaa   1920
attcaattga agcttataca atccccgtca aatcaatgag tggtattgcg acacaagtcg   1980
ttgggttcca attacaaccc ggggacgata gtgcgtttaa gaggacactg ttaggagaga   2040
ttttgaacta ctttgcaaat tggtcgggaa ttatcaaact gacattccca tactgcggtg   2100
cggcgatgac cactggcaca ttcctgatcg cctactcccc tcctggtgct ggcttccctg   2160
ctaaccgcaa ggactcaatg ttgggcactc acattgtctg ggacatagga ttgcaatcga   2220
gttgtgtgct ctgcgtgcca tggatcagtc agacaaacta ccgcttcgtg acgcatgacg   2280
cttatacaga cgctgggttt attacatgct ggtaccaaac aaacatagtg tcacccccag   2340
acatcccggc agacagtaca atcctatgtt ttgtttcagc ttgtaatgat ttctcggtgc   2400
gcttgttaag ggacacgcca ttcatatcac aaaacgcact tctccaaaat gacccggcta   2460
ctgccattgt tagatcagtg gaacgggtgg ccgataccat agcaagtggc ccaatgaatt   2520
ccgagagagt cccagcattg actgccgtcg agacgggtca cacatctcaa gttgttccca   2580
gtgatactat gcaaaccagg catgttgtta accatcacat tagatcggaa tcttcaatag   2640
agaattttct gagtagatcg gcatgcgttt acattgatgt gtatggcaca aaagagaatg   2700
gtgacatcga acgtttcact aactggaaga tcaacacacg ccaggttgtt cagctgaggc   2760
gcaagctgga gatgttcact tacatcagat ttgatgtgga aataacattc gtaattacaa   2820
gtactcaagg gacatcaacc caaacaagca ctggcacccc agtgctcaca catcaagtga   2880
tgtatgtgcc acccggaggc cccatacccg cgtcatatga ggattatagc tggcaaactt   2940
cgacaaaccc cagcgttttc tggacagaag ggaatgcacc ggctcgcatg tcaataccct   3000
ttatgagtgt gggcaatgcc tattgcaact tttatgatgg ctggtcacat ttctcgcaat   3060
ccggcgtgta tggtttcact accctgaaca acatgggaca gctgtttttc agacatgtga   3120
ataaggacac acttggccct tacaacagca cagtgcgtgt ctatttcaaa ccaaagcaca   3180
tcaaagcatg ggtgcccaga ccaccgcgtc tatgcgatta tgtgtatgca cataatgtcg   3240
atttcacccc cagaggagtc acggacataa gggaaaagat cacactggaa agagacgacc   3300
```

```
acacgccttc gatggtaaac cacggtgctt ttggacagca gtggctgcag agcctgctgc   3360
tcttgggcac tgtggcctgc agcatctctg cacccgcccg ctcgcccagc cccagcacgc   3420
agccctggga gcatgtgaat gccatccagg aggcccggcg tctcctgaac ctgagtagag   3480
acactgctgc tgagatgaat gaaacagtag aagtcatctc agaaatgttt gacctccagg   3540
agccgacctg cctacagacc cgcctggagc tgtacaagca gggcctgcgg ggcagcctca   3600
ccaagctcaa gggccccttg accatgatgg ccagccacta caagcagcac tgccctccaa   3660
ccccggaaac ttcctgtgca acccagatta tcacctttga aagtttcaaa gagaacctga   3720
aggactttct gcttgtcatc ccctttgact gctgggagcc agtccaggag gacgaccaca   3780
cgccttcgat ggtaaaccac ggtgcttttg gacagcagtc tggcgccatt tacgtgggta   3840
actacagagt ggtaaatagg cacctggcca cctatgccga ttggcagaat tgcgtgtggg   3900
aagattataa tagagacctc ttagtgagca caaccacagc gcacgggtgt gacaccatcg   3960
ctaggtgtca atgctgcacg ggtgtctact tttgtgcctc aaggaacaag cactacccag   4020
ttagctttga agggccaggc ctagtggaag ttcaggagag tgagtattac ccaaagagat   4080
accagtccca cgtgctgtta gccgcagggt tttctgaacc aggagactgt ggtggaattc   4140
tcaggtgcga gcatggtgtt atcggactag ttaccatggg tggcgaaggc gtagtcggct   4200
ttgctgatgt gcgcgacctg ctgtggttgg aggatgatgc aatggaacaa ggggtcaagg   4260
gttatgtaga acaattgggc aatgccttcg gttccgggtt caccaatcaa atctgcgaac   4320
aagtcaacct cctcaaagaa tcactagtgg gccaagattc catactagag aagtccctta   4380
aagctcttgt gaaaatcatt tcagcactgg taatagtagt gaggaaccat gatgacttaa   4440
ttactgtgac tgccaccctc gctctaattg gctgcacctc atcgccgtgg cggtggctta   4500
aacagaaggt gtcacagtat tacgggatac ccatggctga gcgacaaaac aacgggtggc   4560
tcaaaaagtt tacagagatg accaatgcct gcaaagggat ggagtggatt gccgtcaaga   4620
tccaaaagtt tatagaatgg ctcaagatta aaatcttacc agaggtaaag gagaagcatg   4680
agttcctaac cagacttaaa caactccccc ttctggaaag ccaaattgcc accattgaac   4740
aaagtgcacc gtcccagagt gatcaggaac aactcttctc aaatgttcaa tacttcgccc   4800
actactgcag aaagtacgca cctctgtatg ctactgaggc caaaagagtg ttctcccttg   4860
agaagaaaat gagtaactac atacagttca agtccaaatg ccgtattgaa ccagtatgtt   4920
tgctattgca cgggagtcct ggagctggga aatcggttgc caccaactta attgggcgat   4980
ctctagctga gaagttgaac agttcagtgt attctctacc accagaccct gaccacttcg   5040
atggctataa acaacaagcc gttgtgatta tggacgacct atgccaaaat ccagatggga   5100
aggatgtgtc attattttgt cagatggtgt cgagtgttga ctttgtccca ccaatggctg   5160
ccttggaaga aaaaggaatt ttgtttacct ctccctttgt cttggcctca actaatgctg   5220
gttccatcaa tgccccgacg gtgtcagaca gcagggcttt ggctagaaga ttccactttg   5280
acatgaacat cgaggttata tcaatgtaca gccagaatgg caagattaac atgcccatgt   5340
cagtcaaaac atgcgacgaa gagtgctgtc cagttaactt caaaaagtgt tgcccccttg   5400
tgtgtggaaa agccatacag tttatagata gaagaactca agtgaggtac tccttggaca   5460
tgttggtcac tgagatgttt agggagtaca accataggca cagcgtcggg gcaacccttg   5520
aggcactatt tcaaggtcca ccagtataca gggagatcaa aattactgtt gcacctgata   5580
ccccaccacc accagctatt gcatacctac tgaaatcatt ggacagtgaa gcagttaggg   5640
```

```
agtactgtaa agagaatgga tggctcgttc ctgaaattag ctctaccctt catattgaaa   5700
aacatgtaag ccgagccttt atctgtctcc aggcactgac aacttttgta tccgtggccg   5760
gtattatcta catcatttat aaactatttg cagggtttca aggcgcctac acagggatgc   5820
ccaaccaaaa gccaaaaata cccacactaa ggcaagccaa ggtgcaggga cctgcttgtg   5880
agtttgctgt agccatgatg aagagaaact ccatcacagt gaagacagag tatggtgagt   5940
ttacaatgtt gggcatctac gacaggtggg ccgtactacc acgccatgca aaacccgggc   6000
caaccatcct tatgaatgac caggaagttg gcgtactaga tgcaaaagaa ctagtggata   6060
aagatggcac aaaccttgaa ctgacgctgt tgaagcttga ccggaatgaa aagttcagag   6120
acatcagagg tttcctggcc aaggaagaag tggaggtcaa tgaagctgtt ctagcaataa   6180
acaccagcaa gttcccgaac atgtacatac cagttgggca agtaacagac tacggtttcc   6240
tgaacctggg gggcactccg acgaaaagaa tgctcatgta caattttcct accagagctg   6300
gccaatgtgg tggtattctt atgtctactg gtaaggtgtt ggggatacac gttggtggaa   6360
atggccacca gggcttctca gcagctctcc ttaaacacta cttcaatgat gaacaaggtg   6420
agattgaatt tattgaaagc tcaaaggaag caggtttccc agtcattaat actccaagca   6480
agactaaatt ggaaccaagt gtcttccacc aagtgtttga aggcaacaag gaacctgcag   6540
ttctcaggaa tggtgatcca cgactcaaag caaattttga ggaggcaatc ttttccaaat   6600
atattggtaa tgtgaacaca cacgtagatg agtacatgat ggaagccgtg gatcactacg   6660
caggacaatt ggccacactg gacattaata cggaacctat gaaattggag gatgcagtgt   6720
atggcacaga ggggttggag gcacttgatc taaccaccag tgcagggtac ccgtatgtag   6780
cactgggcat caagaagaga gacatcttgt ctaagaagac cagagatctg actaaattaa   6840
aggagtgtat ggacaaatat ggtctaaacc ttccgatggt gacctatgtg aaggatgagc   6900
tcagatcagc agaaaaagtg gctaaaggca agtctagact tattgaggca tccagcctga   6960
acgactctgt agcgatgaga caaacttttg gcaatctgta cagaacattt catttgaacc   7020
cagggattgt aactggcagt gcagttgggt gtgatcctga ccttttctgg agcaaaatac   7080
ctgtaatgct agatggacat ctcatagcct ttgattactc tggatatgat gccagtttga   7140
gccccgtgtg gtttgcttgt ttgaagctat tgctagaaaa actaggatac tcacacaaag   7200
aaacaaatta cattgactat ttgtgcaatt cccaccattt gtacagagac aagcattact   7260
tcgtgcgtgg cggcatgcca tcaggttgct ccggtaccag catcttcaac tcaatgatca   7320
acaacatcat aatcaggacg ctaatgttga aggtgtacaa aggaattgac ctggatcgat   7380
tcagaatgat tgcctatggc gatgatgtta ttgcgtctta cccctggcca atcgatgcct   7440
ctttacttgc tgaagccggc aaggggtatg ggctgatcat gacaccagca gataaagggg   7500
agtgttttaa tgaagtcacc tggactaatg tcaccttttt gaagagatat ttcagagcag   7560
atgagcaata cccctttgtg gtccatcctg ttatcccaat gaaagacatc catgaatcaa   7620
ttagatggac aaaagaccca aagaacaccc aagaccatgt gcgctctttg tgcttgttgg   7680
cctggcacaa tggggagcac gaatatgagg aattcatcaa gaagatcaga agcgtcccag   7740
tcgggcgctg tctaaccctt cctgcgtttt ggaccctgcg caggaaatgg ttggattcct   7800
tttagattag agacaatttt ctgcaatttg aattggctta accctaccac actcaccgaa   7860
ctagacaacg gtgtggtagg ggtaaattct ccgcattcgg tgcgg                   7905
```

<210> SEQ ID NO 11
<211> LENGTH: 8271

```
<212> TYPE: DNA
<213> ORGANISM: Artificial Sequence
<220> FEATURE:
<223> OTHER INFORMATION: cDNA sequence of ECHO25-Anti-PD1

<400> SEQUENCE: 11

ttaaaacagc ctgtgggttg ttcccaccca tagggcccac tgggcgctag cacactggta     60
ttgtggtacc tttgtgcgcc tgttttatct acccctcccc caaacgtgac ttagaagctc    120
aacacatgtg gtcagcaggt ggcccagtat accaactggg tcttgatcaa gcacttctgt    180
taccccggac cgagtatcaa taggctgctc acgcggctga aggagaaagt gttcgttatc    240
cggccaatta ctacgagaaa cctagtacca ccatggaagt tgcgcggcgt ttcgctccgc    300
acaaccccag tgtagatcag gccgatgagt caccgcactc ctcacgggcg accgtggcgg    360
tggctgcgct ggcggcctgc ccatggggca acccatggga cgcttcaata ccgacatggt    420
gtgaagagtc tattgtgcta attggtaatc ctccggcccc tgaatgcggc taatcccaac    480
tgcggagcag atacccacat gccagtgggc agtctgtcgt aacgggtaac tctgcagcgg    540
aaccgactac tttgggtgtc cgtgtttctt tttattcttt attggctgct tatggtgaca    600
attgagagat tgttgccata tagctattgg attggccatc cggtgacaaa cagaacaata    660
gtttatctat ttgttggttt cataccatta aattttaaag tattaaagac tatcaacttg    720
atcatactac ttaatacagc aaaatgggag ctcatgtgtc aacgcagaaa accggagcgc    780
atgagactgg tttgagcgcc agtgggaatt cggttattca ttacacaaca tcaattatta    840
caaggatgca tcttcaaatt cagcaaacag gcaagacttt tcacaagacc ccagcaaatt    900
taccgaaccc tatgaaggat gtcatgatta aatcactccc ggcgttaaat tcacccactg    960
tggaggaatg tggctacagt gaccgggtgc gctccattac tttgggtaat tcaacaatca   1020
ctacgcagga aagtgcaaat gtggtagttg gctatggtgt ctggccggag tatttgaggg   1080
atgaggaagc cacggcacaa gaccaaccca ctcaaccaga tgttgccacc tgtagattct   1140
acaccctaga atctgttatg tgggagaagt cctcggcggg ctggtggtgg aagtttccag   1200
atgctcttgc agagatgggc ctattcggtc aaaatatgct ataccattat ttgggaaggt   1260
caggctacac aatacacgtg caatgcaatg cgtcaaaatt ccaccaaggg tgccttcttg   1320
tagtctgtgt gccagaagcc gagatgggtt ctgcacagct tgataggaca ttgaatcata   1380
ccaaacttag caacacagaa cacgccagca cattcgggtc catgagttcc aatgaagctg   1440
gggccgtcca aaatgtagtg cacaatgccg ggatgggcgt tggagtgggt aacttgacca   1500
tctaccctca tcagtggatt aatcttagaa ccaacaattg tgccaccata gtaatgccgt   1560
acataaacag tgtgccaatg gataatatgt ttaggcatta caatttcacc cttatggtga   1620
ttccattcgc acagcttgat tatgcaccca gcgcgtccac tcacgttcca ataaccgtga   1680
cagttgcccc catgtgtgcc gaatacaacg ggctaagatt ggcaggtaaa cagggcttac   1740
caacaatgct cactccaggt agcaaccagt tcctcacgtc tgatgatttc cagtccccat   1800
cagcaatgcc acagtttgat gtaacgccgg agattgaaat ccccggtgac gtgaagaatt   1860
taatggaaat ggctgaagtt gattctgtgg tcccagtgaa taatctggat gataaggtaa   1920
attcaattga agcttataca atccccgtca aatcaatgag tggtattgcg acacaagtcg   1980
ttgggttcca attacaaccc ggggacgata gtgcgtttaa gaggacactg ttaggagaga   2040
ttttgaacta ctttgcaaat tggtcgggaa ttatcaaact gacattccca tactgcggtg   2100
cggcgatgac cactggcaca ttcctgatcg cctactcccc tcctggtgct ggcttccctg   2160
```

-continued

```
ctaaccgcaa ggactcaatg ttgggcactc acattgtctg ggacatagga ttgcaatcga   2220

gttgtgtgct ctgcgtgcca tggatcagtc agacaaacta ccgcttcgtg acgcatgacg   2280

cttatacaga cgctgggttt attacatgct ggtaccaaac aaacatagtg tcacccccag   2340

acatcccggc agacagtaca atcctatgtt ttgtttcagc ttgtaatgat ttctcggtgc   2400

gcttgttaag ggacacgcca ttcatatcac aaaacgcact tctccaaaat gacccggcta   2460

ctgccattgt tagatcagtg gaacgggtgg ccgataccat agcaagtggc ccaatgaatt   2520

ccgagagagt cccagcattg actgccgtcg agacgggtca cacatctcaa gttgttccca   2580

gtgatactat gcaaaccagg catgttgtta accatcacat tagatcggaa tcttcaatag   2640

agaattttct gagtagatcg gcatgcgttt acattgatgt gtatggcaca aaagagaatg   2700

gtgacatcga acgtttcact aactggaaga tcaacacacg ccaggttgtt cagctgaggc   2760

gcaagctgga gatgttcact tacatcagat ttgatgtgga aataacattc gtaattacaa   2820

gtactcaagg gacatcaacc caaacaagca ctggcacccc agtgctcaca catcaagtga   2880

tgtatgtgcc acccggaggc cccataccca cgtcatatga ggattatagc tggcaaactt   2940

cgacaaaccc cagcgttttc tggacagaag ggaatgcacc ggctcgcatg tcaataccct   3000

ttatgagtgt gggcaatgcc tattgcaact tttatgatgg ctggtcacat ttctcgcaat   3060

ccggcgtgta tggtttcact accctgaaca acatgggaca gctgtttttc agacatgtga   3120

ataaggacac acttggccct tacaacagca cagtgcgtgt ctatttcaaa ccaaagcaca   3180

tcaaagcatg ggtgcccaga ccaccgcgtc tatgcgatta tgtgtatgca cataatgtcg   3240

atttcacccc cagaggagtc acggacataa gggaaaagat cacactggaa agagacgacc   3300

acacgccttc gatggtaaac cacggtgctt ttggacagca gatgaagcac ctgtggttct   3360

tcctgctgct ggtggccgct cctaggtggg tgctgtccca ggtgcagctg gtgcagagcg   3420

gcgtggaggt gaagaagccc ggcgcttccg tgaaggtgtc ctgcaaggcc tccggctaca   3480

ccttcaccaa ctactacatg tactgggtga ggcaggcccc tggacaggga ctggagtgga   3540

tgggcggcat caacccttcc aacggcggca ccaacttcaa cgagaagttc aagaaccggg   3600

tgaccctgac caccgactcc tccaccacca ccgcctacat ggagctgaag tccctgcagt   3660

ttgacgacac cgccgtgtac tactgcgcca ggagggacta ccggttcgac atgggcttcg   3720

actactgggg ccagggcaca accgtgaccg tgtccagcgg aggtggcgga tctggagggg   3780

gtggtagcgg tggaggcggg agtgagatcg tgctgaccca gtcccctgct acactgtccc   3840

tgtcccccgg cgagagggct acactgagct gcagggcctc caagggcgtg tccacctccg   3900

gctactccta cctgcactgg taccagcaga agcctggaca ggctcccagg ctgctgatct   3960

acctggcctc ctacctggag tccggcgtgc ctgctaggtt ttccggcagc ggcagcggca   4020

ccgatttcac cctgaccatc tcctccctgg agcccgagga cttcgccgtg tactactgcc   4080

agcactccag ggatctgcct ctgaccttcg gcggcggcac caaggtggag atcaaggacg   4140

accacacgcc ttcgatggta aaccacggtg cttttggaca gcagtctggc gccatttacg   4200

tgggtaacta cagagtggta aataggcacc tggccaccta tgccgattgg cagaattgcg   4260

tgtgggaaga ttataataga gacctcttag tgagcacaac cacagcgcac gggtgtgaca   4320

ccatcgctag gtgtcaatgc tgcacgggtg tctacttttg tgcctcaagg aacaagcact   4380

acccagttag ctttgaaggg ccaggcctag tggaagttca ggagagtgag tattacccaa   4440

agagatacca gtcccacgtg ctgttagccg cagggttttc tgaaccagga gactgtggtg   4500

gaattctcag gtgcgagcat ggtgttatcg gactagttac catgggtggc gaaggcgtag   4560
```

```
tcggctttgc tgatgtgcgc gacctgctgt ggttggagga tgatgcaatg gaacaagggg   4620
tcaagggtta tgtagaacaa ttgggcaatg ccttcggttc cgggttcacc aatcaaatct   4680
gcgaacaagt caacctcctc aaagaatcac tagtgggcca agattccata ctagagaagt   4740
cccttaaagc tcttgtgaaa atcatttcag cactggtaat agtagtgagg aaccatgatg   4800
acttaattac tgtgactgcc accctcgctc taattggctg cacctcatcg ccgtggcggt   4860
ggcttaaaca gaaggtgtca cagtattacg ggatacccat ggctgagcga caaaacaacg   4920
ggtggctcaa aaagtttaca gagatgacca atgcctgcaa agggatggag tggattgccg   4980
tcaagatcca aaagtttata gaatggctca agattaaaat cttaccagag gtaaaggaga   5040
agcatgagtt cctaaccaga cttaaacaac tccccttct ggaaagccaa attgccacca   5100
ttgaacaaag tgcaccgtcc cagagtgatc aggaacaact cttctcaaat gttcaatact   5160
tcgcccacta ctgcagaaag tacgcacctc tgtatgctac tgaggccaaa agagtgttct   5220
cccttgagaa gaaaatgagt aactacatac agttcaagtc caaatgccgt attgaaccag   5280
tatgtttgct attgcacggg agtcctggag ctgggaaatc ggttgccacc aacttaattg   5340
ggcgatctct agctgagaag ttgaacagtt cagtgtattc tctaccacca gaccctgacc   5400
acttcgatgg ctataaacaa caagccgttg tgattatgga cgacctatgc caaaatccag   5460
atgggaagga tgtgtcatta ttttgtcaga tggtgtcgag tgttgacttt gtcccaccaa   5520
tggctgcctt ggaagaaaaa ggaattttgt ttacctctcc ctttgtcttg gcctcaacta   5580
atgctggttc catcaatgcc ccgacggtgt cagacagcag ggctttggct agaagattcc   5640
actttgacat gaacatcgag gttatatcaa tgtacagcca gaatggcaag attaacatgc   5700
ccatgtcagt caaaacatgc gacgaagagt gctgtccagt taacttcaaa aagtgttgcc   5760
cccttgtgtg tggaaaagcc atacagttta tagatagaag aactcaagtg aggtactcct   5820
tggacatgtt ggtcactgag atgtttaggg agtacaacca taggcacagc gtcggggcaa   5880
cccttgaggc actatttcaa ggtccaccag tatacaggga gatcaaaatt actgttgcac   5940
ctgatacccc accaccacca gctattgcat acctactgaa atcattggac agtgaagcag   6000
ttagggagta ctgtaaagag aatggatggc tcgttcctga aattagctct acccttcata   6060
ttgaaaaaca tgtaagccga gcctttatct gtctccaggc actgacaact tttgtatccg   6120
tggccggtat tatctacatc atttataaac tatttgcagg gtttcaaggc gcctacacag   6180
ggatgcccaa ccaaaagcca aaaataccca cactaaggca agccaaggtg cagggacctg   6240
cttgtgagtt tgctgtagcc atgatgaaga gaaactccat cacagtgaag acagagtatg   6300
gtgagtttac aatgttgggc atctacgaca ggtgggccgt actaccacgc catgcaaaac   6360
ccgggccaac catccttatg aatgaccagg aagttggcgt actagatgca aaagaactag   6420
tggataaaga tggcacaaac cttgaactga cgctgttgaa gcttgaccgg aatgaaaagt   6480
tcagagacat cagaggtttc ctggccaagg aagaagtgga ggtcaatgaa gctgttctag   6540
caataaacac cagcaagttc ccgaacatgt acataccagt tgggcaagta acagactacg   6600
gtttcctgaa cctgggggc actccgacga aaagaatgct catgtacaat tttcctacca   6660
gagctggcca atgtggtggt attcttatgt ctactggtaa ggtgttgggg atacacgttg   6720
gtggaaatgg ccaccagggc ttctcagcag ctctccttaa acactacttc aatgatgaac   6780
aaggtgagat tgaatttatt gaaagctcaa aggaagcagg tttcccagtc attaatactc   6840
caagcaagac taaattggaa ccaagtgtct tccaccaagt gtttgaaggc aacaaggaac   6900
```

```
ctgcagttct caggaatggt gatccacgac tcaaagcaaa ttttgaggag gcaatctttt   6960
ccaaatatat tggtaatgtg aacacacacg tagatgagta catgatggaa gccgtggatc   7020
actacgcagg acaattggcc acactggaca ttaatacgga acctatgaaa ttggaggatg   7080
cagtgtatgg cacagagggg ttggaggcac ttgatctaac caccagtgca gggtacccgt   7140
atgtagcact gggcatcaag aagagagaca tcttgtctaa gaagaccaga gatctgacta   7200
aattaaagga gtgtatggac aaatatggtc taaaccttcc gatggtgacc tatgtgaagg   7260
atgagctcag atcagcagaa aaagtggcta aaggcaagtc tagacttatt gaggcatcca   7320
gcctgaacga ctctgtagcg atgagacaaa cttttggcaa tctgtacaga acatttcatt   7380
tgaacccagg gattgtaact ggcagtgcag ttgggtgtga tcctgacctt ttctggagca   7440
aaatacctgt aatgctagat ggacatctca tagcctttga ttactctgga tatgatgcca   7500
gtttgagccc cgtgtggttt gcttgtttga agctattgct agaaaaacta ggatactcac   7560
acaaagaaac aaattacatt gactatttgt gcaattccca ccatttgtac agagacaagc   7620
attacttcgt gcgtggcggc atgccatcag gttgctccgg taccagcatc ttcaactcaa   7680
tgatcaacaa catcataatc aggacgctaa tgttgaaggt gtacaaagga attgacctgg   7740
atcgattcag aatgattgcc tatggcgatg atgttattgc gtcttacccc tggccaatcg   7800
atgcctcttt acttgctgaa gccggcaagg ggtatgggct gatcatgaca ccagcagata   7860
aaggggagtg ttttaatgaa gtcacctgga ctaatgtcac ctttttgaag agatatttca   7920
gagcagatga gcaatacccc tttgtggtcc atcctgttat cccaatgaaa gacatccatg   7980
aatcaattag atggacaaaa gacccaaaga acacccaaga ccatgtgcgc tctttgtgct   8040
tgttggcctg gcacaatggg gagcacgaat atgaggaatt catcaagaag atcagaagcg   8100
tcccagtcgg gcgctgtcta acccttcctg cgttttggac cctgcgcagg aaatggttgg   8160
attcctttta gattagagac aattttctgc aatttgaatt ggcttaaccc taccacactc   8220
accgaactag acaacggtgt ggtaggggta aattctccgc attcggtgcg g            8271
```

<210> SEQ ID NO 12
<211> LENGTH: 7428
<212> TYPE: RNA
<213> ORGANISM: Artificial Sequence
<220> FEATURE:
<223> OTHER INFORMATION: Genomic sequence of ECHO25-WT

<400> SEQUENCE: 12

```
uuaaaacagc cugugggguug uucccaccca uagggcccac ugggcgcuag cacacuggua     60
uugugguacc uuugugcgcc uguuuuaucu accccucccc caaacgugac uuagaagcuc    120
aacacaugug gucagcaggu ggcccaguau accaacuggg ucuugaucaa gcacuucugu    180
uaccccggac cgaguaucaa uaggcugcuc acgcggcuga aggagaaagu guucguuauc    240
cggccaauua cuacgagaaa ccuaguacca ccauggaagu ugcgcggcgu uucgcuccgc    300
acaaccccag uguagaucag gccgaugagu caccgcacuc cucacgggcg accguggcgg    360
uggcugcgcu ggcggccugc ccauggggca acccauggga cgcuucaaua ccgacauggu    420
gugaagaguc uauugugcua auugguaauc cuccggcccc ugaaugcggc uaaucccaac    480
ugcggagcag auacccacau gccagugggc agucugucgu aacggguaac ucugcagcgg    540
aaccgacuac uuugggguguc cguguuucuu uuuauucuuu auuggcugcu uaugguugaca    600
auugagagau uguugccaua uagcuauugg auuggccauc cggugacaaa cagaacaaua    660
guuuaucuau uuguugguuu cauaccauua aauuuuaaag uauuaaagac uaucaacuug    720
```

```
aucauacuac uuaauacagc aaaaugggag cucaugugug aacgcagaaa accggagcgc    780
augagacugg uuugagcgcc agugggaauu cgguuauuca uuacacaaca ucaauuauua    840
caaggaugca ucuucaaauu cagcaaacag gcaagacuuu ucacaagacc ccagcaaauu    900
uaccgaaccc uaugaaggau gucaugauua aaucacuccc ggcguuaaau ucacccacug    960
uggaggaaug uggcuacagu gaccgggugc gcuccauuac uuuggguaau ucaacaauca   1020
cuacgcagga aagugcaaau gugguaguug gcuauggugu cuggccggag uauuugaggg   1080
augaggaagc cacggcacaa gaccaaccca cucaaccaga uguugccacc uguagauucu   1140
acacccuaga aucuguuaug ugggagaagu ccucggcggg cugguggugg aaguuuccag   1200
augcucuugc agagaugggc cuauucgguc aaaauaugcu auaccauuau uugggaaggu   1260
caggcuacac aauacacgug caaugcaaug cgucaaaauu ccaccaaggg ugccuucuug   1320
uagucugugu gccagaagcc gagaugggu cugcacagcu ugauaggaca uugaaucaua   1380
ccaaacuuag caacacagaa cacgccagca cauucgggug caugaguucc aaugaagcug   1440
gggccgucca aaauguagug cacaaugccg ggaugggcgu uggagugggu aacuugacca   1500
ucuacccuca ucaguggauu aaucuuagaa ccaacaauug ugccaccaua guaaugccgu   1560
acauaaacag ugugccaaug gauaauaugu uuaggcauua caauuucacc cuuaugguga   1620
uuccauucgc acagcuugau uaugcaccca gcgcguccac ucacguucca auaaccguga   1680
caguugcccc caugugugcc gaauacaacg ggcuaagauu ggcagguaaa cagggcuuac   1740
caacaaugcu cacuccaggu agcaaccagu uccucacguc ugaugauuuc caguccccau   1800
cagcaaugcc acaguuugau guaacgccgg agauugaaau ccccggugac gugaagaauu   1860
uaauggaaau ggcugaaguu gauucugugg ucccagugaa uaaucuggau gauaagguaa   1920
auucaauuga agcuuauaca aucccccguca aaucaaugag ugguauugcg acacaagucg   1980
uuggguucca auuacaaccc ggggacgaua gugcguuuaa gaggacacug uuaggagaga   2040
uuuugaacua cuuugcaaau uggucgggaa uuaucaaacu gacauuccca uacugcggug   2100
cggcgaugac cacuggcaca uuccugaucg ccuacucccc uccuggugcu ggcuucccug   2160
cuaaccgcaa ggacucaaug uugggcacuc acauugucug ggacauagga uugcaaucga   2220
guugugugcu cugcgugcca uggaucaguc agacaaacua ccgcuucgug acgcaugacg   2280
cuuauacaga cgcuggguuu auuacaugcu gguaccaaac aaacauagug ucacccccag   2340
acaucccggc agacaguaca auccuauguu uuguuucagc uuguaaugau uucucggugc   2400
gcuuguuaag ggacacgcca uucauaucac aaaacgcacu ucuccaaaau gacccggcua   2460
cugccauugu uagaucagug gaacgggugg ccgauaccau agcaaguggc ccaaugaauu   2520
ccgagagagu cccagcauug acugccgucg agacggguca cacaucucaa guuguuccca   2580
gugauacuau gcaaaccagg cauguuguua accaucacau uagaucggaa ucuucaauag   2640
agaauuuucu gaguagaucg gcaugcguuu acauugaugu guauggcaca aaagagaaug   2700
gugacaucga acguuucacu aacuggaaga ucaacacacg ccagguuguu cagcugaggc   2760
gcaagcugga gauguucacu uacaucagau uugaugugga aauaacauuc guaauuacaa   2820
guacucaagg gacaucaacc caaacaagca cuggcacccc agugcucaca caucaaguga   2880
uguaugugcc acccggaggc cccauacccg cgucauauga ggauuauagc uggcaaacuu   2940
cgacaaaccc cagcguuuuc uggacagaag ggaaugcacc ggcucgcaug ucaauacccu   3000
uuaugagugu gggcaaugcc uauugcaacu uuuaugaugg cuggucacau uucucgcaau   3060
```

```
ccggcgugua ugguuucacu acccugaaca acaugggaca gcuguuuuuc agacauguga   3120
auaaggacac acuuggcccu uacaacagca cagugcgugu cuauuucaaa ccaaagcaca   3180
ucaaagcaug ggugcccaga ccaccgcguc uaugcgauua uguguaugca cauaaugucg   3240
auuucacccc cagaggaguc acggacauaa gggaaaagau cacacuggaa agagacgacc   3300
acacgccuuc gaugguaaac cacggugcuu uuggacagca gucuggcgcc auuuacgugg   3360
guaacuacag agugguaaau aggcaccugg ccaccuaugc cgauuggcag aauugcgugu   3420
gggaagauua uaauagagac cucuuaguga gcacaaccac agcgcacggg ugugacacca   3480
ucgcuaggug ucaaugcugc acgggugucu acuuuugugc cucaaggaac aagcacuacc   3540
caguuagcuu ugaagggcca ggccuagugg aaguucagga gagugaguau uacccaaaga   3600
gauaccaguc ccacgugcug uuagccgcag gguuuucuga accaggagac ugugguggaa   3660
uucucaggug cgagcauggu guuaucggac uaguuaccau ggguggcgaa ggcguagucg   3720
gcuuugcuga ugugcgcgac cugcuguggu uggaggauga ugcaauggaa caagggguca   3780
aggguuaugu agaacaauug ggcaaugccu ucgguuccgg guucaccaau caaaucugcg   3840
aacaagucaa ccuccucaaa gaaucacuag ugggccaaga uuccauacua gagaaguccc   3900
uuaaagcucu ugugaaaauc auuucagcac ugguaauagu agugaggaac caugaugacu   3960
uaauuacugu gacugccacc cucgcucuaa uuggcugcac cucaucgccg uggcggugge   4020
uuaaacagaa ggugucacag uauuacggga uacccauggc ugagcgacaa aacaacgggu   4080
ggcucaaaaa guuuacagag augaccaaug ccugcaaagg gauggagugg auugccguca   4140
agauccaaaa guuuauagaa uggcucaaga uuaaaaucuu accagaggua aaggagaagc   4200
augaguuccu aaccagacuu aaacaacucc cccuucugga aagccaaauu gccaccauug   4260
aacaaagugc accgucccag agugaucagg aacaacucuu cucaaauguu caauacuucg   4320
cccacuacug cagaaaguac gcaccucugu augcuacuga ggccaaaaga guguucuccc   4380
uugagaagaa aaugaguaac uacauacagu ucaaguccaa augccguauu gaaccaguau   4440
guuugcuauu gcacgggagu ccuggagcug ggaaaucggu ugccaccaac uuaauugggc   4500
gaucucuagc ugagaaguug aacaguucag uguauucucu accaccagac ccugaccacu   4560
ucgauggcua uaaacaacaa gccguuguga uuauggacga ccuaugccaa aauccagaug   4620
ggaaggaugu gucauuauuu ugucagaugg ugucgagugu ugacuuuguc ccaccaaugg   4680
cugccuugga agaaaaagga auuuuguuua ccucucccuu ugucuuggcc ucaacuaaug   4740
cugguuccau caaugccccg acggugucag acagcagggc uuuggcuaga agauuccacu   4800
uugacaugaa caucgagguu auaucaaugu acagccagaa uggcaagauu aacaugccca   4860
ugucagucaa aacaugcgac gaagagugcu guccaguuaa cuucaaaaag uguugccccc   4920
uugugugugg aaaagccaua caguuuauag auagaagaac ucaagugagg uacuccuugg   4980
acauguuggu cacugagaug uuuagggagu acaaccauag gcacagcguc ggggcaaccc   5040
uugaggcacu auuucaaggu ccaccaguau acagggagau caaaauuacu guugcaccug   5100
auaccccacc accaccagcu auugcauacc uacugaaauc auuggacagu gaagcaguua   5160
gggaguacug uaaagagaau ggauggcucg uuccugaaau uagcucuacc cuucauauug   5220
aaaaacaugu aagccgagcc uuuaucuguc uccaggcacu gacaacuuuu guauccgugg   5280
ccgguauuau cuacaucauu uauaaacuau uugcaggguu ucaaggcgcc uacacaggga   5340
ugcccaacca aaagccaaaa auacccacac uaaggcaagc caaggugcag ggaccugcuu   5400
gugaguuugc uguagccaug augaagagaa acuccaucac agugaagaca gaguauggug   5460
```

```
aguuuacaau guugggcauc uacgacaggu gggccguacu accacgccau gcaaaacccg   5520
ggccaaccau ccuuaugaau gaccaggaag uuggcguacu agaugcaaaa gaacuagugg   5580
auaaagaugg cacaaaccuu gaacugacgc uguugaagcu ugaccggaau gaaaaguuca   5640
gagacaucag agguuuccug gccaaggaag aaguggaggu caaugaagcu guucuagcaa   5700
uaaacaccag caaguucccg aacauguaca uaccaguugg gcaaguaaca gacuacgguu   5760
uccugaaccu gggggcacu ccgacgaaaa gaaugcucau guacaauuuu ccuaccagag   5820
cuggccaaug ugguguauu cuuaugucua cugguaaggu guuggggaua cacguuggug   5880
gaaauggcca ccagggcuuc ucagcagcuc uccuuaaaca cuacuucaau gaugaacaag   5940
gugagauuga auuuauugaa agcucaaagg aagcagguuu cccagucauu aauacuccaa   6000
gcaagacuaa auuggaacca agugucuucc accaagugu ugaaggcaac aaggaaccug   6060
caguucucag gaauggugau ccacgacuca aagcaaauuu ugaggaggca aucuuuucca   6120
aauauauugg uaaugugaac acacacguag augaguacau gauggaagcc guggaucacu   6180
acgcaggaca auuggccaca cuggacauua auacggaacc uaugaaauug gaggaugcag   6240
uguauggcac agagggguug gaggcacuug aucuaaccac cagugcaggg uacccguaug   6300
uagcacuggg caucaagaag agagacaucu ugucuaagaa gaccagagau cugacuaaau   6360
uaaaggagug uauggacaaa uauggucuaa accuuccgau ggugaccuau gugaaggaug   6420
agcucagauc agcagaaaaa guggcuaaag gcaagucuag acuuauugag gcauccagcc   6480
ugaacgacuc uguagcgaug agacaaacuu uuggcaaucu guacagaaca uuucauuuga   6540
acccaggau uguaacuggc agugcaguug ggugugaucc ugaccuuuuc uggagcaaaa   6600
uaccuguaau gcuagaugga caucucauag ccuuugauua cucuggauau gaugccaguu   6660
ugagccccgu gugguuugcu uguuugaagc uauugcuaga aaaacuagga uacucacaca   6720
aagaaacaaa uuacauugac uauuugugca auucccacca uuuguacaga gacaagcauu   6780
acuucgugcg uggcggcaug ccaucagguu gcuccgguac cagcaucuuc aacucaauga   6840
ucaacaacau cauaaucagg acgcuaaugu ugaaggugua caaaggaauu gaccuggauc   6900
gauucagaau gauugccuau ggcgaugaug uuauugcguc uuaccccugg ccaaucgaug   6960
ccucuuuacu ugcugaagcc ggcaaggggu augggcugau caugacacca gcagauaaag   7020
gggaguguuu uaaugaaguc accuggacua augucaccuu uuugaagaga uauuucagag   7080
cagaugagca auaccccuuu gugguccauc cuguuauccc aaugaaagac auccaugaau   7140
caauuagaug gacaaaagac ccaaagaaca cccaagacca ugugcgcucu uugugcuugu   7200
uggccuggca caauggggag cacgaauaug aggaauucau caagaagauc agaagcgucc   7260
cagucgggcg cugucuaacc cuuccugcgu uuuggacccu gcgcaggaaa ugguuggauu   7320
ccuuuuagau uagagacaau uuucugcaau uugaauuggc uuaacccuac cacacucacc   7380
gaacuagaca acggugugu agggguaaau ucuccgcauu cggugcgg                7428
```

<210> SEQ ID NO 13
<211> LENGTH: 7309
<212> TYPE: RNA
<213> ORGANISM: Artificial Sequence
<220> FEATURE:
<223> OTHER INFORMATION: Genomic sequence of ECHO25-HRV2

<400> SEQUENCE: 13

```
uuaaaacagc cuguggguug uucccaccca uagggcccac ugggcgcuag cacacuggua     60
```

-continued

```
uugugguacc uuugugcgcc uguuuuaucu accccucccc caaacgugac uuagaagaac    120
uuagaaguuu uucacaaaga ccaauagccg guaaucagcc agauuacuga aggucaagca    180
cuucuguuuc cccggucaau guugauaugc uccaacaggg caaaaacaac ugcgaucguu    240
aaccgcaaag cgccuacgca aagcuuagua gcaucuuuga aaucguuugg cuggucgauc    300
cgccauuucc ccugguagac cuggcagaug aggcuagaaa uaccccacug gcgacagugu    360
ucuagccugc guggcugccu gcacacccua ugggugugaa gccaaacaau ggacaaggug    420
ugaagagccc cgugugcucg cuuugagucc uccggccccu gaauguggcu aaccuuaacc    480
cugcagcuag agcacguaac ccaaugugua ucuagucgua augagcaauu gcgggauggg    540
accaacuacu uugggugucc guguuucacu uuuuccuuua uauuugcuua uggugacaau    600
auauacaaua uauauauugg caccauggga gcucaugugu caacgcagaa aaccggagcg    660
caugagacug guuugagcgc caguggg aau ucgguuauuc auuacacaac aucaauuauu    720
acaaggaugc aucuucaaau ucagcaaaca ggcaagacuu uucacaagac cccagcaaau    780
uuaccgaacc cuaugaagga ugucaugauu aaaucacucc cggcguuaaa uucacccacu    840
guggaggaau guggcuacag ugaccgggug cgcuccauua cuuuggguaa uucaacaauc    900
acuacgcagg aaagugcaaa ugugguaguu ggcuauggug ucuggccgga guauuugagg    960
gaugaggaag ccacggcaca agaccaaccc acucaaccag auguugccac cuguagauuc   1020
uacacccuag aaucuguuau gugggagaag uccucggcgg gcugguggug gaaguuucca   1080
gaugcucuug cagagauggg ccuauucggu caaaauaugc uauaccauua uuugggaagg   1140
ucaggcuaca caauacacgu gcaaugcaau gcgucaaaau uccaccaagg gugccuucuu   1200
guagucugug ugccagaagc cgagaugggu ucugcacagc uugauaggac auugaaucau   1260
accaaacuua gcaacacaga acacgccagc acauucgggu ccaugaguuc caaugaagcu   1320
ggggccgucc aaaauguagu gcacaaugcc gggaugggcg uuggaguggg uaacuugacc   1380
aucuacccuc aucaguggau uaaucuuaga accaacaauu gugccaccau aguaaugccg   1440
uacauaaaca gugugccaau ggauaauaug uuuaggcauu acaauuucac ccuuauggug   1500
auuccauucg cacagcuuga uuaugcaccc agcgcgucca cucacguucc aauaaccgug   1560
acaguugccc ccaugugugc cgaauacaac gggcuaagau uggcagguaa acagggcuua   1620
ccaacaaugc ucacuccagg uagcaaccag uuccucacgu cugaugauuu ccagucccca   1680
ucagcaaugc cacaguuuga uguaacgccg gagauugaaa uccccgguga cgugaagaau   1740
uuaauggaaa uggcugaagu ugauucugug gucccaguga auaaucugga ugauaaggua   1800
aauucaauug aagcuuauac aauccccguc aaaucaauga gugguauugc gacacaaguc   1860
guuggguucc aauuacaacc cggggacgau agugcguuua agaggacacu guuaggagag   1920
auuuugaacu acuuugcaaa uuggucggga auuaucaaac ugacauuccc auacugcggu   1980
gcggcgauga ccacuggcac auuccugauc gccuacuccc cuccuggugc uggcuucccu   2040
gcuaaccgca aggacucaau guugggcacu cacauugucu gggacauagg auugcaaucg   2100
aguugugugc ucugcgugcc auggaucagu cagacaaacu accgcuucgu gacgcaugac   2160
gcuuauacag acgcuggguu uauuacaugc ugguaccaaa caaacauagu gucaccccca   2220
gacaucccgg cagacaguac aauccuaugu uuuguuucag cuuguaauga uuucucggug   2280
cgcuuguuaa gggacacgcc auucauauca caaaacgcac uucuccaaaa ugacccggcu   2340
acugccauug uuagaucagu ggaacgggug gccgauacca uagcaagugg cccaaugaau   2400
uccgagagag ucccagcauu gacugccguc gagacggguc acacaucuca aguuguuccc   2460
```

```
agugauacua ugcaaaccag gcauguuguu aaccaucaca uuagaucgga aucuucaaua   2520
gagaauuuuc ugaguagauc ggcaugcguu uacauugaug uguauggcac aaaagagaau   2580
ggugacaucg aacguuucac uaacuggaag aucaacacac gccagguugu ucagcugagg   2640
cgcaagcugg agauguucac uuacaucaga uuugaugugg aaauaacauu cguaauuaca   2700
aguacucaag ggacaucaac ccaaacaagc acuggcaccc cagugcucac acaucaagug   2760
auguaugugc cacccggagg ccccauaccc gcgucauaug aggauuauag cuggcaaacu   2820
ucgacaaacc ccagcguuuu cuggacagaa gggaaugcac cggcucgcau gucaauaccc   2880
uuuaugagug ugggcaaugc cuauugcaac uuuuaugaug gcuggucaca uuucucgcaa   2940
uccggcgugu augguuucac uacccugaac aacaugggac agcuguuuuu cagacaugug   3000
aauaaggaca cacuuggccc uuacaacagc acagugcgug ucuauuucaa accaaagcac   3060
aucaaagcau gggugcccag accaccgcgu cuaugcgauu auguguaugc acauaauguc   3120
gauuucaccc ccagaggagu cacggacaua agggaaaaga ucacacugga aagagacgac   3180
cacacgccuu cgaugguaaa ccacggugcu uuuggacagc agucuggcgc cauuuacgug   3240
gguaacuaca gagugguaaa uaggcaccug gccaccuaug ccgauuggca gaauugcgug   3300
ugggaagauu auaauagaga ccucuuagug agcacaacca cagcgcacgg gugugacacc   3360
aucgcuaggu gucaaugcug cacggguguc uacuuuugug ccucaaggaa caagcacuac   3420
ccaguuagcu uugaagggcc aggccuagug gaaguucagg agagugagua uuacccaaag   3480
agauaccagu cccacgugcu guuagccgca ggguuuucug aaccaggaga cuguggugga   3540
auucucaggu gcgagcaugg uguuaucgga cuaguuacca uggguggcga aggcguaguc   3600
ggcuuugcug augugcgcga ccugcugugg uuggaggaug augcaaugga acaagggguc   3660
aaggguuaug uagaacaauu gggcaaugcc uucgguuccg gguucaccaa ucaaaucugc   3720
gaacaaguca accuccucaa agaaucacua gugggccaag auuccauacu agagaagucc   3780
cuuaaagcuc uugugaaaau cauuucagca cugguaauag uagugaggaa ccaugaugac   3840
uuaauuacug ugacugccac ccucgcucua auuggcugca ccucaucgcc guggcggugg   3900
cuuaaacaga aggugucaca guauuacggg auacccaugg cugagcgaca aaacaacggg   3960
uggcucaaaa aguuuacaga gaugaccaau gccugcaaag ggauggagug gauugccguc   4020
aagauccaaa aguuuauaga auggcucaag auuaaaaucu uaccagaggu aaaggagaag   4080
caugaguucc uaaccagacu uaaacaacuc ccccuucugg aaagccaaau ugccaccauu   4140
gaacaaagug caccguccca gagugaucag gaacaacucu ucucaaaugu ucaauacuuc   4200
gcccacuacu gcagaaagua cgcaccucug uaugcuacug aggccaaaag aguguucucc   4260
cuugagaaga aaaugaguaa cuacauacag uucaagucca aaugccguau ugaaccagua   4320
uguuugcuau ugcacgggag uccuggagcu gggaaaucgg uugccaccaa cuuaauuggg   4380
cgaucucuag cugagaaguu gaacaguuca guguauucuc uaccaccaga cccugaccac   4440
uucgauggcu auaaacaaca agccguugug auuauggacg accuaugcca aaauccagau   4500
gggaaggaug ugucauuauu uugucagaug gugucgagug uugacuuugu cccaccaaug   4560
gcugccuugg aagaaaaagg aauuuuguuu accucucccu uugucuuggc cucaacuaau   4620
gcugguucca ucaaugcccc gacgguguca gacagcaggg cuuuggcuag aagauuccac   4680
uuugacauga acaucgaggu uauaucaaug uacagccaga auggcaagau uaacaugccc   4740
augucaguca aaacaugcga cgaagagugc uguccaguua acuucaaaaa guguugcccc   4800
```

```
cuugugugug gaaaagccau acaguuuaua gauagaagaa cucaagugag guacuccuug   4860
gacauguugg ucacugagau guuuagggag uacaaccaua ggcacagcgu cggggcaacc   4920
cuugaggcac uauuucaagg uccaccagua uacagggaga ucaaaauuac uguugcaccu   4980
gauaccccac caccaccagc uauugcauac cuacugaaau cauuggacag ugaagcaguu   5040
agggaguacu guaaagagaa uggauggcuc guuccugaaa uuagcucuac ccuucauauu   5100
gaaaaacaug uaagccgagc cuuuaucugu cuccaggcac ugacaacuuu uguauccgug   5160
gccgguauua ucuacaucau uuauaaacua uuugcagggu uucaaggcgc cuacacaggg   5220
augcccaacc aaaagccaaa aauacccaca cuaaggcaag ccaaggugca gggaccugcu   5280
ugugaguuug cuguagccau gaugaagaga aacuccauca cagugaagac agaguauggu   5340
gaguuuacaa uguugggcau cuacgacagg ugggccguac uaccacgcca ugcaaaaccc   5400
gggccaacca uccuuaugaa ugaccaggaa guuggcguac uagaugcaaa agaacuagug   5460
gauaaagaug gcacaaaccu ugaacugacg cuguugaagc uugaccggaa ugaaaaguuc   5520
agagacauca gagguuuccu ggccaaggaa gaaguggagg ucaaugaagc uguucuagca   5580
auaaacacca gcaaguuccc gaacauguac auaccaguug ggcaaguaac agacuacggu   5640
uuccugaacc uggggggcac uccgacgaaa agaaugcuca uguacaauuu uccuaccaga   5700
gcuggccaau gugguggauau ucuuaugucu acugguaagg uguuggggau acacguuggu   5760
ggaaauggcc accagggcuu cucagcagcu cuccuuaaac acuacuucaa ugaugaacaa   5820
ggugagauug aauuuauuga aagcucaaag gaagcagguu ucccagucau uaauacucca   5880
agcaagacua aauuggaacc aagugucuuc caccaagugu uugaaggcaa caaggaaccu   5940
gcaguucuca ggaaugguga uccacgacuc aaagcaaauu uugaggaggc aaucuuuucc   6000
aaauauauug guaaugugaa cacacacgua gaugaguaca ugauggaagc cguggaucac   6060
uacgcaggac aauuggccac acuggacauu aauacggaac cuaugaaauu ggaggaugca   6120
guguauggca cagaggggguu ggaggcacuu gaucuaacca ccagugcagg guacccguau   6180
guagcacugg gcaucaagaa gagagacauc uugucuaaga agaccagaga ucugacuaaa   6240
uuaaaggagu guauggacaa auauggucua aaccuuccga uggugaccua ugugaaggau   6300
gagcucagau cagcagaaaa aguggcuaaa ggcaagucua gacuuauuga ggcauccagc   6360
cugaacgacu cuguagcgau gagacaaacu uuuggcaauc uguacagaac auuucauuug   6420
aacccaggga uuguaacugg cagugcaguu gggugugauc cugaccuuuu cuggagcaaa   6480
auaccuguaa ugcuagaugg acaucucaua gccuuugauu acucuggaua ugaugccagu   6540
uugagccccg uguggguuugc uuguuugaag cuauugcuag aaaaacuagg auacucacac   6600
aaagaaacaa auuacauuga cuauuugugc aauucccacc auuuguacag agacaagcau   6660
uacuucgugc guggcggcau gccaucaggu ugcuccggua ccagcaucuu caacucaaug   6720
aucaacaaca ucauaaucag gacgcuaaug uugaaggugu acaaaggaau ugaccuggau   6780
cgauucagaa ugauugccua uggcgaugau guuauugcgu cuuaccccug gccaaucgau   6840
gccucuuuac uugcugaagc cggcaagggg uaugggcuga ucaugacacc agcagauaaa   6900
ggggaguguu uuaaugaagu caccuggacu aaugucaccu uuuugaagag auauuucaga   6960
gcagaugagc aauaccccuu uguggguccau ccuguuaucc caaugaaaga cauccaugaa   7020
ucaauuagau ggacaaaaga cccaaagaac acccaagacc augugcgcuc uuugugcuug   7080
uuggccuggc acaaugggga gcacgaauau gaggaauuca ucaagaagau cagaagcguc   7140
ccagucgggc gcugucuaac ccuuccugcg uuuuggaccc ugcgcaggaa augguuggau   7200
```

uccuuuuaga uuagagacaa uuuucugcaa uuugaauugg cuuaacccua ccacacucac 7260
cgaacuagac aacggugugg uaggggguaaa uucuccgcau ucggugcgg 7309

<210> SEQ ID NO 14
<211> LENGTH: 7530
<212> TYPE: RNA
<213> ORGANISM: Artificial Sequence
<220> FEATURE:
<223> OTHER INFORMATION: Genomic sequence of ECHO25-miR133&206T

<400> SEQUENCE: 14
uuaaaacagc cuguggguug uucccaccca uagggcccac ugggcgcuag cacacuggua 60
uugugguacc uuugugcgcc uguuuuaucu accccucccc caaacgugac uuagaagcuc 120
aacacaugug gucagcaggu ggcccaguau accaacuggg ucuugaucaa gcacuucugu 180
uaccccggac cgaguaucaa uaggcugcuc acgcggcuga aggagaaagu guucguuauc 240
cggccaauua cuacgagaaa ccuaguacca ccauggaagu ugcgcggcgu uucgcuccgc 300
acaaccccag uguagaucag gccgaugagu caccgcacuc cucacgggcg accguggcgg 360
uggcugcgcu ggcggccugc ccauggggca acccauggga cgcuucaaua ccgacauggu 420
gugaagaguc uauugugcua auugguaauc cuccggcccc ugaaugcggc uaaucccaac 480
ugcggagcag auacccacau gccagugggc agucugucgu aacggguaac ucugcagcgg 540
aaccgacuac uuugggugu cguguuucuu uuuauucuuu auuggcugcu uauggugaca 600
auugagagau uguugccaua uagcuauugg auuggccauc cggugacaaa cagaacaaua 660
guuuaucuau uuguugguuu cauaccauua aauuuuaaag uauuaaagac uaucaacuug 720
aucauacuac uuaauacagc aaaaugggag cucaugugug aacgcagaaa accggagcgc 780
augagacugg uuugagcgcc aguggggaauu cgguuauuca uuacacaaca ucaauuauua 840
caaggaugca ucuucaaauu cagcaaacag gcaagacuuu ucacaagacc ccagcaaauu 900
uaccgaaccc uaugaaggau gucaugauua aaucacuccc ggcguuaaau ucacccacug 960
uggaggaaug uggcuacagu gaccgggugc gcuccauuac uuuggguaau ucaacaauca 1020
cuacgcagga aagugcaaau gugguaguug gcuauggugu cuggccggag uauuugaggg 1080
augaggaagc cacggcacaa gaccaaccca cucaaccaga uguugccacc uguagauucu 1140
acacccuaga aucuguuaug ugggagaagu ccucggcggg cugguggugg aaguuuccag 1200
augcucuugc agagaugggc cuauucgguc aaaauaugcu auaccauuau uugggaaggu 1260
caggcuacac aauacacgug caaugcaaug cgucaaaauu ccaccaaggg ugccuucuug 1320
uagucugugu gccagaagcc gagaugggu cugcacagcu ugauaggaca uugaaucaua 1380
ccaaacuuag caacacagaa cacgccagca cauucgggcu caugaguucc aaugaagcug 1440
gggccgucca aaauguagug cacaaugccg ggaugggcgu uggagugggu aacuugacca 1500
ucuacccuca ucaguggauu aaucuuagaa ccaacaauug ugccaccaua guaaugccgu 1560
acauaaacag ugugccaaug gauaauaugu uuaggcauua caauuucacc cuuaugguga 1620
uuccauucgc acagcuugau uaugcaccca gcgcguccac ucacguucca auaaccguga 1680
caguugcccc cauguguggcc gaauacaacg ggcuaagauu ggcagguaaa cagggcuuac 1740
caacaaugcu cacuccaggu agcaaccagu uccucacguc ugaugauuuc caguccccau 1800
cagcaaugcc acaguuugau guaacgccgg agauugaaau ccccggugac gugaagaauu 1860
uaauggaaau ggcugaaguu gauucugugg ucccagugaa uaaucuggau gauaagguaa 1920

```
auucaauuga agcuuauaca auccccguca aaucaaugag ugguauugcg acacaagucg   1980
uuggguucca auuacaaccc ggggacgaua gugcguuuaa gaggacacug uuaggagaga   2040
uuuugaacua cuuugcaaau uggucgggaa uuaucaaacu gacauuccca uacugcggug   2100
cggcgaugac cacuggcaca uuccugaucg ccuacucccc uccuggugcu ggcuucccug   2160
cuaaccgcaa ggacucaaug uugggcacuc acauugucug ggacauagga uugcaaucga   2220
guugugugcu cugcgugcca uggaucaguc agacaaacua ccgcuucgug acgcaugacg   2280
cuuauacaga cgcuggguuu auuacaugcu gguaccaaac aaacauagug ucacccccag   2340
acaucccggc agacaguaca auccuauguu uuguuucagc uuguaaugau uucucggugc   2400
gcuuguuaag ggacacgcca uucauaucac aaaacgcacu ucuccaaaau gacccggcua   2460
cugccauugu uagaucagug gaacgggugg ccgauaccau agcaaguggc ccaaugaauu   2520
ccgagagagu cccagcauug acugccgucg agacggguca cacaucucaa guuguuccca   2580
gugauacuau gcaaaccagg cauguuguua accaucacau uagaucggaa ucuucaauag   2640
agaauuuucu gaguagaucg gcaugcguuu acauugaugu guauggcaca aaagagaaug   2700
gugacaucga acguuucacu aacuggaaga ucaacacacg ccagguuguu cagcugaggc   2760
gcaagcugga gauguucacu uacaucagau uugaugugga aauaacauuc guaauuacaa   2820
guacucaagg gacaucaacc caaacaagca cuggcacccc agugcucaca caucaaguga   2880
uguaugugcc acccggaggc cccauacccg cgucauauga ggauuauagc uggcaaacuu   2940
cgacaaaccc cagcguuuuc uggacagaag ggaaugcacc ggcucgcaug ucaauacccu   3000
uuaugagugu gggcaaugcc uauugcaacu uuuaugaugg cuggucacau uucucgcaau   3060
ccggcgugua ugguuucacu acccugaaca acaugggaca gcuguuuuuc agacauguga   3120
auaaggacac acuuggcccu uacaacagca cagugcgugu cuauuucaaa ccaaagcaca   3180
ucaaagcaug ggugcccaga ccaccgcguc uaugcgauua uguguaugca cauaaugucg   3240
auuucacccc cagaggaguc acggacauaa gggaaaagau cacacuggaa agagacgacc   3300
acacgccuuc gaugguaaac cacggugcuu uuggacagca gucuggcgcc auuuacgugg   3360
guaacuacag agugguaaau aggcaccugg ccaccuaugc cgauuggcag aauugcgugu   3420
gggaagauua uaauagagac cucuuaguga gcacaaccac agcgcacggg ugugacacca   3480
ucgcuaggug ucaaugcugc acgggugucu acuuuugugc cucaaggaac aagcacuacc   3540
caguuagcuu ugaagggcca ggccuagugg aaguucagga gagugaguau uacccaaaga   3600
gauaccaguc ccacgugcug uuagccgcag gguuuucuga accaggagac ugugguggaa   3660
uucucaggug cgagcauggu guuaucggac uaguuaccau ggguggcgaa ggcguagucg   3720
gcuuugcuga ugugcgcgac cugcuguggu uggaggauga ugcaauggaa caagggguca   3780
aggguuaugu agaacaauug ggcaaugccu ucgguuccgg guucaccaau caaaucugcg   3840
aacaagucaa ccuccucaaa gaaucacuag ugggccaaga uuccauacua gagaaguccc   3900
uuaaagcucu ugugaaaauc auuucagcac ugguaauagu agugaggaac caugaugacu   3960
uaauuacugu gacugccacc cucgcucuaa uuggcugcac cucaucgccg uggcgguggc   4020
uuaaacagaa ggugucacag uauuacggga uacccauggc ugagcgacaa aacaacgggu   4080
ggcucaaaaa guuuacagag augaccaaug ccugcaaagg gauggagugg auugccguca   4140
agauccaaaa guuuauagaa uggcucaaga uuaaaaucuu accagaggua aaggagaagc   4200
augaguuccu aaccagacuu aaacaacucc cccuucugga aagccaaauu gccaccauug   4260
aacaaagugc accgucccag agugaucagg aacaacucuu cucaaauguu caauacuucg   4320
```

```
cccacuacug cagaaaguac gcaccucugu augcuacuga ggccaaaaga guguucuccc   4380
uugagaagaa aaugaguaac uacauacagu ucaaguccaa augccguauu gaaccaguau   4440
guuugcuauu gcacgggagu ccuggagcug ggaaaucggu ugccaccaac uuaauugggc   4500
gaucucuagc ugagaaguug aacaguucag uguauucucu accaccagac ccugaccacu   4560
ucgauggcua uaaacaacaa gccguuguga uuauggacga ccuaugccaa aauccagaug   4620
ggaaggaugu gucauuauuu ugucagaugg ugucgagugu ugacuuuguc ccaccaaugg   4680
cugccuugga agaaaaagga auuuuguuua ccucucccuu ugucuuggcc ucaacuaaug   4740
cugguuccau caaugccccg acggugucag acagcagggc uuuggcuaga agauuccacu   4800
uugacaugaa caucgagguu auaucaaugu acagccagaa uggcaagauu aacaugccca   4860
ugucagucaa aacaugcgac gaagagugcu guccaguuaa cuucaaaaag uguugccccc   4920
uuguguguggg aaaagccaua caguuuauag auagaagaac ucaagugagg uacuccuugg   4980
acauguuggu cacugagaug uuuagggagu acaaccauag gcacagcguc ggggcaaccc   5040
uugaggcacu auuucaaggu ccaccaguau acagggagau caaaauuacu guugcaccug   5100
auaccccacc accaccagcu auugcauacc uacugaaauc auuggacagu gaagcaguua   5160
gggaguacug uaaagagaau ggauggcucg uuccugaaau uagcucuacc cuucauauug   5220
aaaaacaugu aagccgagcc uuuaucuguc uccaggcacu gacaacuuuu guauccgugg   5280
ccgguauuau cuacaucauu uauaaacuau uugcaggguu ucaaggcgcc uacacaggga   5340
ugcccaacca aaagccaaaa auacccacac uaaggcaagc caaggugcag ggaccugcuu   5400
gugaguuugc uguagccaug augaagagaa acuccaucac agugaagaca gaguauggug   5460
aguuuacaau guugggcauc uacgacaggu gggccguacu accacgccau gcaaaacccg   5520
ggccaaccau ccuuaugaau gaccaggaag uuggcguacu agaugcaaaa gaacuagugg   5580
auaaagaugg cacaaaccuu gaacugacgc uguugaagcu ugaccggaau gaaaaguuca   5640
gagacaucag agguuuccug gccaaggaag aaguggaggu caaugaagcu guucuagcaa   5700
uaaacaccag caaguucccg aacauguaca uaccaguugg gcaaguaaca gacuacgguu   5760
uccugaaccu gggggggcacu ccgacgaaaa gaaugcucau guacaauuuu ccuaccagag   5820
cuggccaaug ugguggguauu cuuaugucua cugguaaggu guuggggaua cacguuggug   5880
gaaauggcca ccagggcuuc ucagcagcuc uccuuaaaca cuacuucaau gaugaacaag   5940
gugagauuga auuuauugaa agcucaaagg aagcagguuu cccagucauu aauacuccaa   6000
gcaagacuaa auuggaacca agugucuucc accaaguguu ugaaggcaac aaggaaccug   6060
caguucucag gaauggugau ccacgacuca aagcaaauuu ugaggaggca aucuuuucca   6120
aauauauugg uaaugugaac acacacguag augaguacau gauggaagcc guggaucacu   6180
acgcaggaca auuggccaca cuggacauua auacggaacc uaugaaauug gaggaugcag   6240
uguauggcac agaggggguug gaggcacuug aucuaaccac cagugcaggg uacccguaug   6300
uagcacuggg caucaagaag agagacaucu ugucuaagaa gaccagagau cugacuaaau   6360
uaaaggagug uauggacaaa uauggucuaa accuuccgau ggugaccuau gugaaggaug   6420
agcucagauc agcagaaaaa guggcuaaag gcaagucuag acuuauugag gcauccagcc   6480
ugaacgacuc uguagcgaug agacaaacuu uuggcaaucu guacagaaca uuucauuuga   6540
acccagggau uguaacuggc agugcaguug ggugugaucc ugaccuuuuc uggagcaaaa   6600
uaccuguaau gcuagaugga caucucauag ccuuugauua cucuggauau gaugccaguu   6660
```

ugagccccgu gugguuugcu uguuugaagc uauugcuaga aaaacuagga uacucacaca 6720
aagaaacaaa uuacauugac uauuugugca auucccacca uuuguacaga gacaagcauu 6780
acuucgugcg uggcggcaug ccaucagguu gcuccgguac cagcaucuuc aacucaauga 6840
ucaacaacau cauaaucagg acgcuaaugu ugaaggugua caaaggaauu gaccuggauc 6900
gauucagaau gauugccuau ggcgaugaug uuauugcguc uuaccccugg ccaaucgaug 6960
ccucuuuacu ugcugaagcc ggcaaggggu augggcugau caugacacca gcagauaaag 7020
gggaguguuu uaaugaaguc accuggacua augucaccuu uuugaagaga uauuucagag 7080
cagaugagca auaccccuuu gugguccauc cuguuauccc aaugaaagac auccaugaau 7140
caauuagaug gacaaaagac ccaaagaaca cccaagacca ugugcgcucu uugugcuugu 7200
uggccuggca caauggggag cacgaauaug aggaauucau caagaagauc agaagcgucc 7260
cagucgggcg cugucuaacc cuuccugcgu uuuggacccu gcgcaggaaa ugguuggauu 7320
ccuuuuagau uagagacaca gcugguugaa ggggaccaac gauacagcug guugaagggg 7380
accaaaccgg uccacacacu uccuuacauu ccaucaccca cacacuuccu uacauuccaa 7440
auuuucugca auuugaauug gcuuaacccu accacacuca ccgaacuaga caacggugug 7500 guaggggaa auucuccgca uucggugcgg 7530

<210> SEQ ID NO 15
<211> LENGTH: 7905
<212> TYPE: RNA
<213> ORGANISM: Artificial Sequence
<220> FEATURE:
<223> OTHER INFORMATION: Genomic sequence of ECHO25-GM-CSF

<400> SEQUENCE: 15
uuaaaacagc cugugggguug uucccaccca uagggcccac ugggcgcuag cacacuggua 60
uugugguacc uuugugcgcc uguuuuaucu accccucccc caaacgugac uuagaagcuc 120
aacacaugug gucagcaggu ggcccaguau accaacuggg ucuugaucaa gcacuucugu 180
uaccccggac cgaguaucaa uaggcugcuc acgcggcuga aggagaaagu guucguuauc 240
cggccaauua cuacgagaaa ccuaguacca ccauggaagu ugcgcggcgu uucgcuccgc 300
acaaccccag uguagaucag gccgaugagu caccgcacuc cucacgggcg accguggcgg 360
uggcugcgcu ggcggccugc ccauggggca acccauggga cgcuucaaua ccgacauggu 420
gugaagaguc uauugugcua auugguaauc cuccggcccc ugaaugcggc uaaucccaac 480
ugcggagcag auacccacau gccagugggc agucugucgu aacggguaac ucugcagcgg 540
aaccgacuac uuuggguguc cguguuucuu uuuauucuuu auuggcugcu uauggugaca 600
auugagagau uguugccaua uagcuauugg auuggccauc cggugacaaa cagaacaaua 660
guuuaucuau uuguugguuu cauaccauua aauuuuaaag uauuaaagac uaucaacuug 720
aucauacuac uuaauacagc aaaaugggag cucauguguc aacgcagaaa accggagcgc 780
augagacugg uuugagcgcc aguggggaauu cgguuauuca uuacacaaca ucaauuauua 840
caaggaugca ucuucaaauu cagcaaacag gcaagacuuu ucacaagacc ccagcaaauu 900
uaccgaaccc uaugaaggau gucaugauua aaucacuccc ggcguuaaau ucacccacug 960
uggaggaaug uggcuacagu gaccgggugc gcuccauuac uuuggguaau ucaacaauca 1020
cuacgcagga aagugcaaau gugguaguug gcuauggugu cuggccggag uauuugaggg 1080
augaggaagc cacggcacaa gaccaaccca cucaaccaga uguugccacc uguagauucu 1140
acacccuaga aucuguuaug ugggagaagu ccucggcggg cugguggugg aaguuuccag 1200

```
augcucuugc agagaugggc cuauucgguc aaaauaugcu auaccauuau uugggaaggu 1260
caggcuacac aauacacgug caaugcaaug cgucaaaauu ccaccaaggg ugccuucuug 1320
uagucugugu gccagaagcc gagauggguu cugcacagcu ugauaggaca uugaaucaua 1380
ccaaacuuag caacacagaa cacgccagca cauucggguc caugaguucc aaugaagcug 1440
gggccgucca aaauguagug cacaaugccg ggaugggcgu uggagugggu aacuugacca 1500
ucuacccuca ucaguggauu aaucuuagaa ccaacaauug ugccaccaua guaaugccgu 1560
acauaaacag ugugccaaug gauaauaugu uuaggcauua caauuucacc cuuaugguga 1620
uuccauucgc acagcuugau uaugcaccca gcgcguccac ucacguucca auaaccguga 1680
caguugcccc caugugugcc gaauacaacg ggcuaagauu ggcagguaaa cagggcuuac 1740
caacaaugcu cacuccaggu agcaaccagu uccucacguc ugaugauuuc caguccccau 1800
cagcaaugcc acaguuugau guaacgccgg agauugaaau ccccggugac gugaagaauu 1860
uaauggaaau ggcugaaguu gauucugugg ucccagugaa uaaucuggau gauaagguaa 1920
auucaauuga agcuuauaca auccccguca aaucaaugag ugguauugcg acacaagucg 1980
uuggguucca auuacaaccc ggggacgaua gugcguuuaa gaggacacug uuaggagaga 2040
uuuugaacua cuuugcaaau uggucgggaa uuaucaaacu gacauuccca uacugcggug 2100
cggcgaugac cacuggcaca uuccugaucg ccuacucccc uccuggugcu ggcuucccug 2160
cuaaccgcaa ggacucaaug uugggcacuc acauugucug ggacauagga uugcaaucga 2220
guugugugcu cugcgugcca uggaucaguc agacaaacua ccgcuucgug acgcaugacg 2280
cuuauacaga cgcuggguuu auuacaugcu gguaccaaac aaacauagug ucaccccag 2340
acaucccggc agacaguaca auccuauguu uuguuucagc uuguaaugau uucucggugc 2400
gcuuguuaag ggacacgcca uucauaucac aaaacgcacu ucuccaaaau gacccggcua 2460
cugccauugu uagaucagug gaacgggugg ccgauaccau agcaaguggc ccaaugaauu 2520
ccgagagagu cccagcauug acugccgucg agacggguca cacaucucaa guuguuccca 2580
gugauacuau gcaaaccagg cauguuguua accaucacau uagaucggaa ucuucaauag 2640
agaauuuucu gaguagaucg gcaugcguuu acauugaugu guauggcaca aaagagaaug 2700
gugacaucga acguuucacu aacuggaaga ucaacacacg ccagguuguu cagcugaggc 2760
gcaagcugga gauguucacu uacaucagau uugaugugga aauaacauuc guaauuacaa 2820
guacucaagg gacaucaacc caaacaagca cuggcacccc agugcucaca caucaaguga 2880
uguaugugcc acccggaggc cccauacccg cgucauauga ggauuauagc uggcaaacuu 2940
cgacaaaccc cagcguuuuc uggacagaag ggaaugcacc ggcucgcaug ucaauacccu 3000
uuaugagugu gggcaaugcc uauugcaacu uuuaugaugg cuggucacau uucucgcaau 3060
ccggcgugua ugguuucacu acccugaaca acaugggaca gcuguuuuuc agacauguga 3120
auaaggacac acuuggcccu uacaacagca cagugcgugu cuauuucaaa ccaaagcaca 3180
ucaaagcaug ggugcccaga ccaccgcguc uaugcgauua uguguaugca cauaaugucg 3240
auuucacccc cagaggaguc acggacauaa gggaaaagau cacacuggaa agagacgacc 3300
acacgccuuc gaugguaaac cacggugcuu uggacagca guggcugcag agccugcugc 3360
ucuugggcac uguggccugc agcaucucug cacccgcccg cucgcccagc cccagcacgc 3420
agcccuggga gcaugugaau gccauccagg aggcccggcg ucuccugaac cugaguagag 3480
acacugcugc ugagaugaau gaaacaguag aagucaucuc agaaauguuu gaccuccagg 3540
```

```
agccgaccug ccuacagacc cgccuggagc uguacaagca gggccugcgg ggcagccuca   3600
ccaagcucaa gggccccuug accaugaugg ccagccacua caagcagcac ugcccuccaa   3660
ccccggaaac uuccugugca acccagauua ucaccuuuga aaguuucaaa gagaaccuga   3720
aggacuuucu gcuugucauc ccuuugacu gcugggagcc aguccaggag gacgaccaca   3780
cgccuucgau gguaaaccac ggugcuuuug gacagcaguc uggcgccauu uacgugggua   3840
acuacagagu gguaaauagg caccuggcca ccuaugccga uuggcagaau ugcguguggg   3900
aagauuauaa uagagaccuc uuagugagca caaccacagc gcacgggugu gacaccaucg   3960
cuaggugcua augcugcacg ggugucuacu uuugugccuc aaggaacaag cacuacccag   4020
uuagcuuuga agggccaggc cuaguggaag uucaggagag ugaguauuac ccaaagagau   4080
accagucccca cgugcuguua gccgcagggu uuucugaacc aggagacugu gguggaauuc   4140
ucaggugcga gcauggugu aucggacuag uuaccauggg uggcgaaggc guagucggcu   4200
uugcugaugu gcgcgaccug cugugguugg aggaugaugc aauggaacaa ggggucaagg   4260
guuauguaga acaauugggc aaugccuucg guuccggguu caccaaucaa aucugcgaac   4320
aagucaaccu ccucaaagaa ucacuagugg gccaagauuc cauacuagag aagucccuua   4380
aagcucuugu gaaaaucauu ucagcacugg uaauaguagu gaggaaccau gaugacuuaa   4440
uuacugugac ugccacccuc gcucuaauug gcugcaccuc aucgccgugg cgguggcuua   4500
aacagaaggu gucacaguau uacgggauac ccauggcuga gcgacaaaac aacgggugc   4560
ucaaaaaguu uacagagaug accaaugccu gcaaagggau ggaguggauu gccgucaaga   4620
uccaaaaguu uauagaaugg cucaagauua aaaucuuacc agagguaaag gagaagcaug   4680
aguuccuaac cagacuuaaa caacuccccc uucuggaaag ccaaauugcc accauugaac   4740
aaagugcacc gucccagagu gaucaggaac aacucuucuc aaauguucaa uacuucgccc   4800
acuacugcag aaaguacgca ccucuguaug cuacugaggc caaaagagug uucucccuug   4860
agaagaaaau gaguaacuac auacaguuca aguccaaaug ccguauugaa ccaguauguu   4920
ugcuauugca cgggaguccu ggagcuggga aaucgguugc caccaacuua auugggcgau   4980
cucuagcuga gaaguugaac aguucagugu auucucuacc accagacccu gaccacuucg   5040
auggcuauaa acaacaagcc guugugauua uggacgaccu augccaaaau ccagauggga   5100
aggauguguc auuauuuugu cagauggugu cgaguguuga cuuuguccca ccaauggcug   5160
ccuuggaaga aaaaggaauu uuguuuaccu cucccuuugu cuuggccuca acuaaugcug   5220
guuccaucaa ugccccgacg gugucagaca gcagggcuuu ggcuagaaga uuccacuuug   5280
acaugaacau cgagguuaua ucaauguaca gccagaaugg caagauuaac augcccaugu   5340
cagucaaaac augcgacgaa gagugcuguc caguuaacuu caaaaagugu ugcccccuug   5400
uguguggaaa agccauacag uuuauagaua gaagaacuca agugagguac uccuuggaca   5460
uguuggucac ugagauguuu agggaguaca accauaggca cagcgucggg gcaacccuug   5520
aggcacuauu ucaaggucca ccaguauaca gggagaucaa aauuacuguu gcaccugaua   5580
ccccaccacc accagcuauu gcauaccuac ugaaaucauu ggacagugaa gcaguuaggg   5640
aguacuguaa agagaaugga uggcucguuc cugaaauuag cucuacccuu cauauugaaa   5700
aacauguaag ccgagccuuu aucugucucc aggcacugac aacuuuugua uccguggccg   5760
guauuaucua caucauuuau aaacuauuug cagguuuca aggcgccuac acagggaugc   5820
ccaaccaaaa gccaaaaaua cccacacuaa ggcaagccaa ggugcaggga ccugcuugug   5880
aguuugcugu agccaugaug aagagaaacu ccaucacagu gaagacagag uauggugagu   5940
```

```
uuacaauguu gggcaucuac gacaggtuggg ccguacuacc acgccaugca aaacccgggc   6000
```

uuacaauguu gggcaucuac gacagguggg ccguacuacc acgccaugca aaacccgggc 6000
caaccauccu uaugaaugac caggaaguug gcguacuaga ugcaaaagaa cuaguggaua 6060
aagauggcac aaaccuugaa cugacgcugu ugaagcuuga ccggaaugaa aaguucagag 6120
acaucagagg uuuccuggcc aaggaagaag uggaggucaa ugaagcuguu cuagcaauaa 6180
acaccagcaa guucccgaac auguacauac caguugggca aguaacagac uacgguuucc 6240
ugaaccuggg gggcacuccg acgaaaagaa ugcucaugua caauuuuccu accagagcug 6300
gccaaugugg ugguauucuu augucuacug guaaggugu ggggauacac guugguggaa 6360
auggccacca gggcuucuca gcagcucucc uuaaacacua cuucaaugau gaacaaggug 6420
agauugaauu uauugaaagc ucaaaggaag cagguuuccc agucauuaau acuccaagca 6480
agacuaaauu ggaaccaagu gucuuccacc aaguguuuga aggcaacaag gaaccugcag 6540
uucucaggaa uggugaucca cgacucaaag caaauuuuga ggaggcaauc uuuuccaaau 6600
auauugguaa ugugaacaca cacguagaug aguacaugau ggaagccgug gaucacuacg 6660
caggacaauu ggccacacug gacauuaaua cggaaccuau gaaauuggag gaugcagugu 6720
auggcacaga gggguuggag gcacuugauc uaaccaccag ugcaggguac ccguauguag 6780
cacugggcau caagaagaga gacaucuugu cuaagaagac cagagaucug acuaaauuaa 6840
aggaguguau ggacaaauau ggucuaaacc uuccgauggu gaccuaugug aaggaugagc 6900
ucagaucagc agaaaaagug gcuaaaggca agucuagacu uauugaggca uccagccuga 6960
acgacucugu agcgaugaga caaacuuuug gcaaucugua cagaacauuu cauuugaacc 7020
cagggauugu aacuggcagu gcaguugggu gugauccuga ccuuuucugg agcaaaauac 7080
cuguaaugcu agauggacau cucauagccu uugauuacuc uggauaugau gccaguuuga 7140
gccccgugug guuugcuugu uugaagcuau ugcuagaaaa acuaggauac ucacacaaag 7200
aaacaaauua cauugacuau uugugcaauu cccaccauuu guacagagac aagcauuacu 7260
ucgugcgugg cggcaugcca ucagguugcu ccgguaccag caucuucaac ucaaugauca 7320
acaacaucau aaucaggacg cuaauguuga aggguguacaa aggaauugac cuggaucgau 7380
ucagaaugau ugccuauggc gaugauguua uugcgucuua ccccuggcca aucgaugccu 7440
cuuuacuugc ugaagccggc aaggggguaug ggcugaucau gacaccagca gauaaagggg 7500
aguguuuuaa ugaagucacc uggacuaaug ucaccuuuuu gaagagauau uucagagcag 7560
augagcaaua ccccuuugug guccauccug uuaucccaau gaaagacauc caugaaucaa 7620
uuagauggac aaaagaccca aagaacaccc aagaccaugu gcgcucuuug ugcuuguugg 7680
ccuggcacaa uggggagcac gaauaugagg aauucaucaa gaagaucaga agcgucccag 7740
ucgggcgcug ucuaacccuu ccugcguuuu ggacccugcg caggaaaugg uuggauuccu 7800
uuuagauuag agacaauuuu cugcaauuug aauuggcuua acccuaccac acucaccgaa 7860
cuagacaacg gugugguagg gguaaauucu ccgcauucgg ugcgg 7905

<210> SEQ ID NO 16
<211> LENGTH: 8271
<212> TYPE: RNA
<213> ORGANISM: Artificial Sequence
<220> FEATURE:
<223> OTHER INFORMATION: Genomic sequence of ECHO25-Anti-PD1

<400> SEQUENCE: 16
uuaaaacagc cugugggguug uucccaccca uagggcccac ugggcgcuag cacacuggua 60

-continued

```
uugugguacc uuugugcgcc uguuuuaucu accccucccc caaacgugac uuagaagcuc    120
aacacaugug gucagcaggu ggcccaguau accaacuggg ucuugaucaa gcacuucugu    180
uaccccggac cgaguaucaa uaggcugcuc acgcggcuga aggagaaagu guucguuauc    240
cggccaauua cuacgagaaa ccuaguacca ccauggaagu ugcgcggcgu uucgcuccgc    300
acaaccccag uguagaucag gccgaugagu caccgcacuc cucacgggcg accguggcgg    360
uggcugcgcu ggcggccugc ccauggggca acccauggga cgcuucaaua ccgacauggu    420
gugaagaguc uauugugcua auugguaauc cuccggcccc ugaaugcggc uaaucccaac    480
ugcggagcag auacccacau gccagugggc agucugucgu aacggguaac ucugcagcgg    540
aaccgacuac uuuggguguc cguguuucuu uuuauucuuu auuggcugcu uauggugaca    600
auugagagau uguugccaua uagcuauugg auuggccauc cggugacaaa cagaacaaua    660
guuuaucuau uuguugguuu cauaccauua aauuuuaaag uauuaaagac uaucaacuug    720
aucauacuac uuaauacagc aaaaugggag cucauguguc aacgcagaaa accggagcgc    780
augagacugg uuugagcgcc aguggaauu cgguuauuca uuacacaaca ucaauuauua    840
caaggaugca ucuucaaauu cagcaaacag gcaagacuuu ucacaagacc ccagcaaauu    900
uaccgaaccc uaugaaggau gucaugauua aaucacuccc ggcguuaaau ucacccacug    960
uggaggaaug uggcuacagu gaccgggugc gcuccauuac uuuggguaau ucaacaauca   1020
cuacgcagga aagugcaaau gugguaguug gcuauggugu cuggccggag uauuugaggg   1080
augaggaagc cacggcacaa gaccaaccca cucaaccaga uguugccacc uguagauucu   1140
acacccuaga aucuguuaug ugggagaagu ccucggcggg cugguggugg aaguuuccag   1200
augcucuugc agagaugggc cuauucgguc aaaauaugcu auaccauuau uugggaaggu   1260
caggcuacac aauacacgug caaugcaaug cgucaaaauu ccaccaaggg ugccuucuug   1320
uagucugugu gccagaagcc gagaugggu cugcacagcu ugauaggaca uugaaucaua   1380
ccaaacuuag caacacagaa cacgccagca cauucgggu caugaguucc aaugaagcug   1440
gggccgucca aaauguagug cacaaugccg ggaugggcgu uggagugggu aacuugacca   1500
ucuacccuca ucaguggauu aaucuuagaa ccaacaauug ugccaccaua guaaugccgu   1560
acauaaacag ugugccaaug gauaaauaugu uuaggcauua caauuucacc cuuauggua   1620
uuccauucgc acagcuugau uaugcaccca gcgcguccac ucacguucca auaaccguga   1680
caguugcccc caugugugcc gaauacaacg ggcuaagauu ggcagguaaa cagggcuuac   1740
caacaaugcu cacuccaggu agcaaccagu uccucacguc ugaugauuuc caguccccau   1800
cagcaaugcc acaguuugau guaacgccgg agauugaaau ccccggugac gugaagaauu   1860
uaauggaaau ggcugaaguu gauucugugg ucccagugaa uaaucuggau gauaagguaa   1920
auucaauuga agcuuauaca aucccccguca aaucaaugag ugguauugcg acacaagucg   1980
uuggguucca auuacaaccc ggggacgaua gugcguuuaa gaggacacug uuaggagaga   2040
uuuugaacua cuuugcaaau uggucgggaa uuaucaaacu gacauuccca uacugcggug   2100
cggcgaugac cacuggcaca uuccugaucg ccuacucccc uccuggugcu ggcuucccug   2160
cuaaccgcaa ggacucaaug uugggcacuc acauugucug ggacauagga uugcaaucga   2220
guugugugcu cugcgugcca uggaucaguc agacaaacua ccgcuucgug acgcaugacg   2280
cuuauacaga cgcuggguuu auuacaugcu gguaccaaac aaacauagug ucaccccccag   2340
acaucccggc agacaguaca auccuauguu uuguuucagc uuguaaugau uucucggugc   2400
gcuuguuaag ggacacgcca uucauaucac aaaacgcacu ucuccaaaau gacccggcua   2460
```

```
cugccauugu uagaucagug gaacgggugg ccgauaccau agcaaguggc ccaaugaauu   2520
ccgagagagu cccagcauug acugccgucg agacggguca cacaucucaa guuguuccca   2580
gugauacuau gcaaaccagg cauguuguua accaucacau uagaucggaa ucuucaauag   2640
agaauuuucu gaguagaucg gcaugcguuu acauugaugu guauggcaca aaagagaaug   2700
gugacaucga acguuucacu aacuggaaga ucaacacacg ccagguuguu cagcugaggc   2760
gcaagcugga gauguucacu uacaucagau uugaugugga aauaacauuc guaauuacaa   2820
guacucaagg gacaucaacc caaacaagca cuggcacccc agugcucaca caucaaguga   2880
uguaugugcc acccggaggc cccauacccg cgucauauga ggauuauagc uggcaaacuu   2940
cgacaaaccc cagcguuuuc uggacagaag ggaaugcacc ggcucgcaug ucaauacccu   3000
uuaugagugu gggcaaugcc uauugcaacu uuuaugaugg cuggucacau uucucgcaau   3060
ccggcgugua ugguuucacu acccugaaca acaugggaca gcuguuuuuc agacauguga   3120
auaaggacac acuuggcccu uacaacagca cagugcgugu cuauuucaaa ccaaagcaca   3180
ucaaagcaug ggugcccaga ccaccgcguc uaugcgauua uguguaugca cauaaugucg   3240
auuucacccc cagaggaguc acggacauaa gggaaaagau cacacuggaa agagacgacc   3300
acacgccuuc gaugguaaac cacggugcuu uuggacagca gaugaagcac cugugguucu   3360
uccugcugcu gguggccgcu ccuagguggg ugcuguccca ggugcagcug gugcagagcg   3420
gcguggaggu gaagaagccc ggcgcuuccg ugaaggugucc cugcaaggcc uccggcuaca   3480
ccuucaccaa cuacuacaug uacuggguga ggcaggcccc uggacaggga cuggagugga   3540
ugggcggcau caacccuucc aacggcggca ccaacuucaa cgagaaguuc aagaaccggg   3600
ugacccugac caccgacucc uccaccacca ccgccuacau ggagcugaag ucccugcagu   3660
uugacgacac cgccguguac uacugcgcca ggagggacua ccgguucgac augggcuucg   3720
acuacugggg ccagggcaca accgugaccg uguccagcgg agguggcgga ucuggagggg   3780
gugguagcgg uggaggcggg agugagaucg ugcugaccca guccccugcu acacuguccc   3840
ugucccccgg cgagagggcu acacugagcu gcagggccuc caagggcgug uccaccuccg   3900
gcuacuccua ccugcacugg uaccagcaga agccuggaca ggcucccagg cugcugaucu   3960
accuggccuc cuaccuggag uccggcgugc cugcuagguu uuccggcagc ggcagcggca   4020
ccgauuucac ccugaccauc uccucccugg agcccgagga cuucgccgug uacuacugcc   4080
agcacuccag ggaucugccu cugaccuucg gcggcggcac caagguggag aucaaggacg   4140
accacacgcc uucgauggua aaccacggug cuuuuggaca gcagucuggc gccauuuacg   4200
uggguaacua cagaguggua aauaggcacc uggccaccua ugccgauugg cagaauugcg   4260
ugugggaaga uuauaauaga gaccucuuag ugagcacaac cacagcgcac gggugugaca   4320
ccaucgcuag gugucaaugc ugcacgggug ucuacuuuug ugccucaagg aacaagcacu   4380
acccaguuag cuuugaaggg ccaggccuag uggaaguuca ggagagugag uauuacccaa   4440
agagauacca gucccacgug cuguuagccg cagggguuuuc ugaaccagga gacuguggug   4500
gaauucucag gugcgagcau ggguguuaucg gacuaguuac caugggguggc gaaggcguag   4560
ucggcuuugc ugaugugcgc gaccugcugu gguuggagga ugaugcaaug gaacaagggg   4620
ucaaggguua uguagaacaa uugggcaaug ccuucgguuc cgguucacc aaucaaaucu    4680
gcgaacaagu caaccuccuc aaagaaucac uagugggcca agauuccaua cuagagaagu   4740
cccuuaaagc ucuugugaaa aucauuucag cacugguaau aguagugagg aaccaugaug   4800
```

```
acuuaauuac ugugacugcc acccucgcuc uaauuggcug caccucaucg ccguggcggu   4860
ggcuuaaaca gaagguguca caguauuacg ggauacccau ggcugagcga caaaacaacg   4920
gguggcucaa aaaguuuaca gagaugacca augccugcaa agggauggag uggauugccg   4980
ucaagaucca aaaguuuaua gaauggcuca agauuaaaau cuuaccagag guaaaggaga   5040
agcaugaguu ccuaaccaga cuuaaacaac ucccccuucu ggaaagccaa auugccacca   5100
uugaacaaag ugcaccgucc cagagugauc aggaacaacu cuucucaaau guucaauacu   5160
ucgcccacua cugcagaaag uacgcacccu uguaugcuac ugaggccaaa agaguguucu   5220
cccuugagaa gaaaaugagu aacuacauac aguucaaguc caaaugccgu auugaaccag   5280
uauguuugcu auugcacggg aguccuggag cugggaaauc gguugccacc aacuuaauug   5340
ggcgaucucu agcugagaag uugaacaguu caguguauuc ucuaccacca gacccugacc   5400
acuucgaugg cuauaaacaa caagccguug ugauuaugga cgaccuaugc caaaauccag   5460
augggaagga ugugucauua uuuugucaga uggugucgag uguugacuuu gucccaccaa   5520
uggcugccuu ggaagaaaaa ggaauuuugu uuaccucucc cuuugucuug gccucaacua   5580
augcugguuc caucaaugcc ccgacggugu cagacagcag ggcuuuggcu agaagauucc   5640
acuuugacau gaacaucgag guuauaucaa uguacagcca gaauggcaag auuaacaugc   5700
ccaugucagu caaaacaugc gacgaagagu gcuguccagu uaacuucaaa aaguguugcc   5760
cccuugugug uggaaaagcc auacaguuua uagauagaag aacucaagug agguacuccu   5820
uggacauguu ggucacugag auguuuaggg aguacaacca uaggcacagc gucggggcaa   5880
cccuugaggc acuauuucaa gguccaccag uauacaggga gaucaaaauu acuguugcac   5940
cugauacccc accaccacca gcuauugcau accuacugaa aucauuggac agugaagcag   6000
uuagggagua cuguaaagag aauggauggc ucguuccuga aauuagcucu acccuucaua   6060
uugaaaaaca uguaagccga gccuuuaucu gucuccaggc acugacaacu uuuguauccg   6120
uggccgguau uaucuacauc auuuauaaac uauuugcagg guuucaaggc gccuacacag   6180
ggaugcccaa ccaaaagcca aaaauaccca cacuaaggca agccaaggug cagggaccug   6240
cuugugaguu ugcuguagcc augaugaaga gaaacuccau cacagugaag acagaguaug   6300
gugaguuuac aauguugggc aucuacgaca gguggggcgu acuaccacgc caugcaaaac   6360
ccgggccaac cauccuuaug aaugaccagg aaguuggcgu acuagaugca aaagaacuag   6420
uggauaaaga uggcacaaac cuugaacuga cgcuguugaa gcuugaccgg aaugaaaagu   6480
ucagagacau cagagguuuc cuggccaagg aagaagugga ggucaaugaa gcuguucuag   6540
caauaaacac cagcaaguuc ccgaacaugu acauaccagu ugggcaagua acagacuacg   6600
guuuccugaa ccugggggc acuccgacga aaagaaugcu cauguacaau uuuccuacca   6660
gagcuggcca augugguggu auucuuaugu cuacugguaa ggguguuggg auacacguug   6720
guggaaaugg ccaccagggc uucucagcag cucuccuuaa acacuacuuc aaugaugaac   6780
aaggugagau ugaauuuauu gaaagcucaa aggaagcagg uuucccaguc auuaauacuc   6840
caagcaagac uaaauuggaa ccaagugucu uccaccaagu guuugaaggc aacaaggaac   6900
cugcaguucu caggaauggu gauccacgac ucaaagcaaa uuuugaggag gcaaucuuuu   6960
ccaaauauau ugguaaugug aacacacacg uagaugagua caugauggaa gccguggauc   7020
acuacgcagg acaauuggcc acacuggaca uuaauacgga accuaugaaa uuggaggaug   7080
caguguaugg cacagagggg uuggaggcac uugaucuaac caccagugca ggguacccgu   7140
auguagcacu gggcaucaag aagagagaca ucuugucuaa gaagaccaga gaucugacua   7200
```

aauuaaagga guguauggac aaauaugguc uaaaccuucc gauggugacc uaugugaagg 7260
augagcucag aucagcagaa aaaguggcua aaggcaaguc uagacuuauu gaggcaucca 7320
gccugaacga cucuguagcg augagacaaa cuuuuggcaa ucuguacaga acauuucauu 7380
ugaacccagg gauuguaacu ggcagugcag uuggguguga uccugaccuu uucuggagca 7440
aaauaccugu aaugcuagau ggacaucuca uagccuuuga uuacucugga uaugaugcca 7500
guuugagccc cgugugguuu gcuuguuuga agcuauugcu agaaaaacua ggauacucac 7560
acaaagaaac aaauuacauu gacuauuugu gcaauuccca ccauuuguac agagacaagc 7620
auuacuucgu gcguggcggc augccaucag guugcuccgg uaccagcauc uucaacucaa 7680
ugaucaacaa caucauaauc aggacgcuaa uguugaaggu guacaaagga auugaccugg 7740
aucgauucag aaugauugcc uauggcgaug auguuauugc gucuuacccc uggccaaucg 7800
augccucuuu acuugcugaa gccggcaagg gguaugggcu gaucaugaca ccagcagaua 7860
aaggggagug uuuuaaugaa gucaccugga cuaaugucac cuuuuugaag agauauuuca 7920
gagcagauga gcaauacccc uuugugguccc auccuguuau cccaaugaaa gacauccaug 7980
aaucaauuag auggacaaaa gacccaaaga acacccaaga ccaugugcgc ucuuugugcu 8040
uguuggccug gcacaauggg gagcacgaau augaggaauu caucaagaag aucagaagcg 8100
ucccagucgg gcgcugucua acccuuccug cguuuuggac ccugcgcagg aaaugguugg 8160
auuccuuuua gauuagagac aauuuucugc aauuugaauu ggcuuaaccc uaccacacuc 8220
accgaacuag acaacggugu gguaggggua aauucuccgc auucggugcg g 8271

<210> SEQ ID NO 17
<211> LENGTH: 22
<212> TYPE: DNA
<213> ORGANISM: Artificial Sequence
<220> FEATURE:
<223> OTHER INFORMATION: DNA sequence of miR-133 target sequence

<400> SEQUENCE: 17
acagctggtt gaaggggacc aa 22

<210> SEQ ID NO 18
<211> LENGTH: 22
<212> TYPE: DNA
<213> ORGANISM: Artificial Sequence
<220> FEATURE:
<223> OTHER INFORMATION: DNA sequence of miR-206 target sequence

<400> SEQUENCE: 18
ccacacactt ccttacattc ca 22

<210> SEQ ID NO 19
<211> LENGTH: 102
<212> TYPE: DNA
<213> ORGANISM: Artificial Sequence
<220> FEATURE:
<223> OTHER INFORMATION: DNA sequence of tandem sequence of miR-133
target sequence and miR-206 target sequence

<400> SEQUENCE: 19
acagctggtt gaaggggacc aacgatacag ctggttgaag gggaccaaac cggtccacac 60
acttccttac attccatcac ccacacactt ccttacattc ca 102

<210> SEQ ID NO 20
<211> LENGTH: 507

-continued

```
<212> TYPE: DNA
<213> ORGANISM: Artificial Sequence
<220> FEATURE:
<223> OTHER INFORMATION: DNA sequence of the internal ribosome entry
      site sequence of HRV2

<400> SEQUENCE: 20

aacttagaag tttttcacaa agaccaatag ccggtaatca gccagattac tgaaggtcaa      60

gcacttctgt ttccccggtc aatgttgata tgctccaaca gggcaaaaac aactgcgatc     120

gttaaccgca aagcgcctac gcaaagctta gtagcatctt tgaaatcgtt tggctggtcg     180

atccgccatt tcccctggta gacctggcag atgaggctag aaatacccca ctggcgacag     240

tgttctagcc tgcgtggctg cctgcacacc ctatgggtgt gaagccaaac aatggacaag     300

gtgtgaagag ccccgtgtgc tcgctttgag tcctccggcc cctgaatgtg gctaacctta     360

accctgcagc tagagcacgt aacccaatgt gtatctagtc gtaatgagca attgcgggat     420

gggaccaact actttgggtg tccgtgtttc actttttcct ttatatttgc ttatggtgac     480

aatatataca atatatatat tggcacc                                         507
```